US010696995B2

(12) United States Patent  (10) Patent No.: US 10,696,995 B2
Andre et al.  (45) Date of Patent: Jun. 30, 2020

(54) ENZYMATIC PRODUCTION OF GLYCOSYLATED SYNTHONS

(71) Applicants: Institut National de la Recherche Agronomique (INRA), Paris (FR); Institut National des Sciences Appliquees de Toulouse (INSAT), Toulouse (FR); Centre National de la Recherche Scientifique, Paris (FR); Universite de Bordeaux, Bordeaux (FR); Institut Polytechnique de Bordeaux, Talence (FR)

(72) Inventors: Isabelle Andre, Toulouse (FR); Stephane Grelier, Parentis-en-born (FR); David Guieysse, Pechabou (FR); Alvaro Lafraya, Toulouse (FR); Pierre Monsan, Mondonville (FR); Claire Moulis, Vieillevigne (FR); Frederic Peruch, Gradignan (FR); Magali Remaud-Simeon, Ramonville St Agne (FR); Marlene Vuillemin, Ramonville St Agne (FR)

(73) Assignees: INSTITUT NATIONAL DE RECHERCHE POUR L'AGRICULTURE, L'ALIMENTATION ET L'ENVIRONNEMENT, Paris (FR); INSTITUT NATIONAL DES SCIENCES APPIQUEES DE TOULOUSE (INSAT), Toulouse (FR); CENTRE NATIONAL DE LA RECHERCHE SCIENTIFIQUE, Paris (FR); UNIVERSITE DE BORDEAUX, Bordeaux (FR); INSTITUT POLYTECHNIQUE DE BORDEAUX, Talence (FR)

( * ) Notice: Subject to any disclaimer, the term of this patent is extended or adjusted under 35 U.S.C. 154(b) by 92 days.

(21) Appl. No.: 15/559,193

(22) PCT Filed: Mar. 17, 2016

(86) PCT No.: PCT/EP2016/055843
§ 371 (c)(1),
(2) Date: Sep. 18, 2017

(87) PCT Pub. No.: WO2016/146764
PCT Pub. Date: Sep. 22, 2016

(65) Prior Publication Data
US 2018/0258456 A1  Sep. 13, 2018

(30) Foreign Application Priority Data
Mar. 19, 2015  (FR) ...................................... 15 52254

(51) Int. Cl.
C12P 19/60 (2006.01)
C08F 20/28 (2006.01)
C08F 20/58 (2006.01)
C12P 19/44 (2006.01)
C12P 19/58 (2006.01)
C08L 5/00 (2006.01)
C12N 9/24 (2006.01)

(52) U.S. Cl.
CPC .............. *C12P 19/60* (2013.01); *C08F 20/28* (2013.01); *C08F 20/58* (2013.01); *C08L 5/00* (2013.01); *C12N 9/24* (2013.01); *C12P 19/44* (2013.01); *C12P 19/58* (2013.01)

(58) Field of Classification Search
None
See application file for complete search history.

(56) References Cited

PUBLICATIONS

Stam et al., "Dividing the large glycoside hydrolase family 13 into subfamilies: towards improved functional annotations of a-amylase-related proteins", Protein Engineering, Design & Selection vol. 19 No. 12 pp. 555-562, 2006. doi:10.1093/protein/gzl044.*

* cited by examiner

*Primary Examiner* — Suzanne M Noakes
(74) *Attorney, Agent, or Firm* — W&C IP

(57) ABSTRACT

The present invention relates to a method for producing a glycosylated synthon or a monomer. Said method includes at least one step of placing at least one glycan-saccharase in the presence of at least one hydroxylated synthon and at least one saccharose. The invention also relates to a method for producing a glyco(co)polymer, including polymerizing at least two monomers separately obtained from the enzymatic glycosylation method according to the invention, and to a method for producing a glyco(co)polymer, preferably a block glyco(co)polymer, including coupling at least two monomers separately obtained from the enzymatic glycosylation method according to the invention.

11 Claims, No Drawings
Specification includes a Sequence Listing.

SEQUENCE LISTING

<160> NUMBER OF SEQ ID NOS: 18

<210> SEQ ID NO 1
<211> LENGTH: 628
<212> TYPE: PRT
<213> ORGANISM: Neisseria polysaccharea

<400> SEQUENCE: 1

```
Ser Pro Asn Ser Gln Tyr Leu Lys Thr Arg Ile Leu Asp Ile Tyr Thr
1               5                   10                  15

Pro Glu Gln Arg Ala Gly Ile Glu Lys Ser Glu Asp Trp Arg Gln Phe
            20                  25                  30

Ser Arg Arg Met Asp Thr His Phe Pro Lys Leu Met Asn Glu Leu Asp
        35                  40                  45

Ser Val Tyr Gly Asn Asn Glu Ala Leu Leu Pro Met Leu Glu Met Leu
    50                  55                  60

Leu Ala Gln Ala Trp Gln Ser Tyr Ser Gln Arg Asn Ser Ser Leu Lys
65                  70                  75                  80
```

```
Asp Ile Asp Ile Ala Arg Glu Asn Asn Pro Asp Trp Ile Leu Ser Asn
                85                  90                  95
Lys Gln Val Gly Gly Val Cys Tyr Val Asp Leu Phe Ala Gly Asp Leu
            100                 105                 110
Lys Gly Leu Lys Asp Lys Ile Pro Tyr Phe Gln Glu Leu Gly Leu Thr
        115                 120                 125
Tyr Leu His Leu Met Pro Leu Phe Lys Cys Pro Glu Gly Lys Ser Asp
    130                 135                 140
Gly Gly Tyr Ala Val Ser Ser Tyr Arg Asp Val Asn Pro Ala Leu Gly
145                 150                 155                 160
Thr Ile Gly Asp Leu Arg Glu Val Ile Ala Ala Leu His Glu Ala Gly
                165                 170                 175
Ile Ser Ala Val Val Asp Phe Ile Phe Asn His Thr Ser Asn Glu His
            180                 185                 190
Glu Trp Ala Gln Arg Cys Ala Ala Gly Asp Pro Leu Phe Asp Asn Phe
        195                 200                 205
Tyr Tyr Ile Phe Pro Asp Arg Arg Met Pro Asp Gln Tyr Asp Arg Thr
    210                 215                 220
Leu Arg Glu Ile Phe Pro Asp Gln His Pro Gly Gly Phe Ser Gln Leu
225                 230                 235                 240
Glu Asp Gly Arg Trp Val Trp Thr Thr Phe Asn Ser Phe Gln Trp Asp
                245                 250                 255
Leu Asn Tyr Ser Asn Pro Trp Val Phe Arg Ala Met Ala Gly Glu Met
            260                 265                 270
Leu Phe Leu Ala Asn Leu Gly Val Asp Ile Leu Arg Met Asp Ala Val
        275                 280                 285
Ala Phe Ile Trp Lys Gln Met Gly Thr Ser Cys Glu Asn Leu Pro Gln
    290                 295                 300
Ala His Ala Leu Ile Arg Ala Phe Asn Ala Val Met Arg Ile Ala Ala
305                 310                 315                 320
Pro Ala Val Phe Phe Lys Ser Glu Ala Ile Val His Pro Asp Gln Val
                325                 330                 335
Val Gln Tyr Ile Gly Gln Asp Glu Cys Gln Ile Gly Tyr Asn Pro Leu
            340                 345                 350
Gln Met Ala Leu Leu Trp Asn Thr Leu Ala Thr Arg Glu Val Asn Leu
        355                 360                 365
Leu His Gln Ala Leu Thr Tyr Arg His Asn Leu Pro Glu His Thr Ala
    370                 375                 380
Trp Val Asn Tyr Val Arg Ser His Asp Asp Ile Gly Trp Thr Phe Ala
385                 390                 395                 400
Asp Glu Asp Ala Ala Tyr Leu Gly Ile Ser Gly Tyr Asp His Arg Gln
                405                 410                 415
Phe Leu Asn Arg Phe Phe Val Asn Arg Phe Asp Gly Ser Phe Ala Arg
            420                 425                 430
Gly Val Pro Phe Gln Tyr Asn Pro Ser Thr Gly Asp Cys Arg Val Ser
        435                 440                 445
Gly Thr Ala Ala Ala Leu Val Gly Leu Ala Gln Asp Asp Pro His Ala
    450                 455                 460
Val Asp Arg Ile Lys Leu Leu Tyr Ser Ile Ala Leu Ser Thr Gly Gly
465                 470                 475                 480
Leu Pro Leu Ile Tyr Leu Gly Asp Glu Val Gly Thr Leu Asn Asp Asp
                485                 490                 495
```

```
Asp Trp Ser Gln Asp Ser Asn Lys Ser Asp Asp Ser Arg Trp Ala His
            500                 505                 510

Arg Pro Arg Tyr Asn Glu Ala Leu Tyr Ala Gln Arg Asn Asp Pro Ser
            515                 520                 525

Thr Ala Ala Gly Gln Ile Tyr Gln Asp Leu Arg His Met Ile Ala Val
            530                 535                 540

Arg Gln Ser Asn Pro Arg Phe Asp Gly Gly Arg Leu Val Thr Phe Asn
545                 550                 555                 560

Thr Asn Asn Lys His Ile Ile Gly Tyr Ile Arg Asn Asn Ala Leu Leu
                565                 570                 575

Ala Phe Gly Asn Phe Ser Glu Tyr Pro Gln Thr Val Thr Ala His Thr
            580                 585                 590

Leu Gln Ala Met Pro Phe Lys Ala His Asp Leu Ile Gly Gly Lys Thr
            595                 600                 605

Val Ser Leu Asn Gln Asp Leu Thr Leu Gln Pro Tyr Gln Val Met Trp
            610                 615                 620

Leu Glu Ile Ala
625

<210> SEQ ID NO 2
<211> LENGTH: 628
<212> TYPE: PRT
<213> ORGANISM: Neisseria polysaccharea
<220> FEATURE:
<221> NAME/KEY: VARIANT
<222> LOCATION: 226
<223> OTHER INFORMATION: Xaa est choisi parmi A, C, D, E, F, G, H, I, K,
      L, M, N, P, Q, S, T, V, W et Y

<400> SEQUENCE: 2

Ser Pro Asn Ser Gln Tyr Leu Lys Thr Arg Ile Leu Asp Ile Tyr Thr
1               5                   10                  15

Pro Glu Gln Arg Ala Gly Ile Glu Lys Ser Glu Asp Trp Arg Gln Phe
            20                  25                  30

Ser Arg Arg Met Asp Thr His Phe Pro Lys Leu Met Asn Glu Leu Asp
            35                  40                  45

Ser Val Tyr Gly Asn Asn Glu Ala Leu Leu Pro Met Leu Glu Met Leu
50                  55                  60

Leu Ala Gln Ala Trp Gln Ser Tyr Ser Gln Arg Asn Ser Ser Leu Lys
65                  70                  75                  80

Asp Ile Asp Ile Ala Arg Glu Asn Asn Pro Asp Trp Ile Leu Ser Asn
                85                  90                  95

Lys Gln Val Gly Val Cys Tyr Val Asp Leu Phe Ala Gly Asp Leu
            100                 105                 110

Lys Gly Leu Lys Asp Lys Ile Pro Tyr Phe Gln Glu Leu Gly Leu Thr
            115                 120                 125

Tyr Leu His Leu Met Pro Leu Phe Lys Cys Pro Glu Gly Lys Ser Asp
            130                 135                 140

Gly Gly Tyr Ala Val Ser Ser Tyr Arg Asp Val Asn Pro Ala Leu Gly
145                 150                 155                 160

Thr Ile Gly Asp Leu Arg Glu Val Ile Ala Ala Leu His Glu Ala Gly
                165                 170                 175

Ile Ser Ala Val Val Asp Phe Ile Phe Asn His Thr Ser Asn Glu His
            180                 185                 190

Glu Trp Ala Gln Arg Cys Ala Ala Gly Asp Pro Leu Phe Asp Asn Phe
            195                 200                 205
```

```
Tyr Tyr Ile Phe Pro Asp Arg Arg Met Pro Asp Gln Tyr Asp Arg Thr
210                 215                 220
Leu Xaa Glu Ile Phe Pro Asp Gln His Pro Gly Gly Phe Ser Gln Leu
225                 230                 235                 240
Glu Asp Gly Arg Trp Val Trp Thr Thr Phe Asn Ser Phe Gln Trp Asp
            245                 250                 255
Leu Asn Tyr Ser Asn Pro Trp Val Phe Arg Ala Met Ala Gly Glu Met
            260                 265                 270
Leu Phe Leu Ala Asn Leu Gly Val Asp Ile Leu Arg Met Asp Ala Val
        275                 280                 285
Ala Phe Ile Trp Lys Gln Met Gly Thr Ser Cys Glu Asn Leu Pro Gln
290                 295                 300
Ala His Ala Leu Ile Arg Ala Phe Asn Ala Val Met Arg Ile Ala Ala
305                 310                 315                 320
Pro Ala Val Phe Phe Lys Ser Glu Ala Ile Val His Pro Asp Gln Val
                325                 330                 335
Val Gln Tyr Ile Gly Gln Asp Glu Cys Gln Ile Gly Tyr Asn Pro Leu
            340                 345                 350
Gln Met Ala Leu Leu Trp Asn Thr Leu Ala Thr Arg Glu Val Asn Leu
        355                 360                 365
Leu His Gln Ala Leu Thr Tyr Arg His Asn Leu Pro Glu His Thr Ala
370                 375                 380
Trp Val Asn Tyr Val Arg Ser His Asp Asp Ile Gly Trp Thr Phe Ala
385                 390                 395                 400
Asp Glu Asp Ala Ala Tyr Leu Gly Ile Ser Gly Tyr Asp His Arg Gln
                405                 410                 415
Phe Leu Asn Arg Phe Phe Val Asn Arg Phe Asp Gly Ser Phe Ala Arg
            420                 425                 430
Gly Val Pro Phe Gln Tyr Asn Pro Ser Thr Gly Asp Cys Arg Val Ser
        435                 440                 445
Gly Thr Ala Ala Ala Leu Val Gly Leu Ala Gln Asp Asp Pro His Ala
450                 455                 460
Val Asp Arg Ile Lys Leu Leu Tyr Ser Ile Ala Leu Ser Thr Gly Gly
465                 470                 475                 480
Leu Pro Leu Ile Tyr Leu Gly Asp Glu Val Gly Thr Leu Asn Asp Asp
                485                 490                 495
Asp Trp Ser Gln Asp Ser Asn Lys Ser Asp Asp Ser Arg Trp Ala His
            500                 505                 510
Arg Pro Arg Tyr Asn Glu Ala Leu Tyr Ala Gln Arg Asn Asp Pro Ser
        515                 520                 525
Thr Ala Ala Gly Gln Ile Tyr Gln Asp Leu Arg His Met Ile Ala Val
530                 535                 540
Arg Gln Ser Asn Pro Arg Phe Asp Gly Gly Arg Leu Val Thr Phe Asn
545                 550                 555                 560
Thr Asn Asn Lys His Ile Ile Gly Tyr Ile Arg Asn Asn Ala Leu Leu
                565                 570                 575
Ala Phe Gly Asn Phe Ser Glu Tyr Pro Gln Thr Val Thr Ala His Thr
            580                 585                 590
Leu Gln Ala Met Pro Phe Lys Ala His Asp Leu Ile Gly Gly Lys Thr
        595                 600                 605
Val Ser Leu Asn Gln Asp Leu Thr Leu Gln Pro Tyr Gln Val Met Trp
610                 615                 620
Leu Glu Ile Ala
```

<210> SEQ ID NO 3
<211> LENGTH: 628
<212> TYPE: PRT
<213> ORGANISM: Neisseria polysaccharea
<220> FEATURE:
<221> NAME/KEY: VARIANT
<222> LOCATION: 228
<223> OTHER INFORMATION: Xaa est choisi parmi A, C, D, E, F, G, H, L, M, N, P, Q, R, S, T, V, W et Y

<400> SEQUENCE: 3

```
Ser Pro Asn Ser Gln Tyr Leu Lys Thr Arg Ile Leu Asp Ile Tyr Thr
1               5                   10                  15

Pro Glu Gln Arg Ala Gly Ile Glu Lys Ser Glu Asp Trp Arg Gln Phe
            20                  25                  30

Ser Arg Arg Met Asp Thr His Phe Pro Lys Leu Met Asn Glu Leu Asp
        35                  40                  45

Ser Val Tyr Gly Asn Asn Glu Ala Leu Leu Pro Met Leu Glu Met Leu
    50                  55                  60

Leu Ala Gln Ala Trp Gln Ser Tyr Ser Gln Arg Asn Ser Ser Leu Lys
65                  70                  75                  80

Asp Ile Asp Ile Ala Arg Glu Asn Asn Pro Asp Trp Ile Leu Ser Asn
                85                  90                  95

Lys Gln Val Gly Gly Val Cys Tyr Val Asp Leu Phe Ala Gly Asp Leu
            100                 105                 110

Lys Gly Leu Lys Asp Lys Ile Pro Tyr Phe Gln Glu Leu Gly Leu Thr
        115                 120                 125

Tyr Leu His Leu Met Pro Leu Phe Lys Cys Pro Glu Gly Lys Ser Asp
    130                 135                 140

Gly Gly Tyr Ala Val Ser Ser Tyr Arg Asp Val Asn Pro Ala Leu Gly
145                 150                 155                 160

Thr Ile Gly Asp Leu Arg Glu Val Ile Ala Ala Leu His Glu Ala Gly
                165                 170                 175

Ile Ser Ala Val Val Asp Phe Ile Phe Asn His Thr Ser Asn Glu His
            180                 185                 190

Glu Trp Ala Gln Arg Cys Ala Ala Gly Asp Pro Leu Phe Asp Asn Phe
        195                 200                 205

Tyr Tyr Ile Phe Pro Asp Arg Arg Met Pro Asp Gln Tyr Asp Arg Thr
    210                 215                 220

Leu Arg Glu Xaa Phe Pro Asp Gln His Pro Gly Gly Phe Ser Gln Leu
225                 230                 235                 240

Glu Asp Gly Arg Trp Val Trp Thr Thr Phe Asn Ser Phe Gln Trp Asp
                245                 250                 255

Leu Asn Tyr Ser Asn Pro Trp Val Phe Arg Ala Met Ala Gly Glu Met
            260                 265                 270

Leu Phe Leu Ala Asn Leu Gly Val Asp Ile Leu Arg Met Asp Ala Val
        275                 280                 285

Ala Phe Ile Trp Lys Gln Met Gly Thr Ser Cys Glu Asn Leu Pro Gln
    290                 295                 300

Ala His Ala Leu Ile Arg Ala Phe Asn Ala Val Met Arg Ile Ala Ala
305                 310                 315                 320

Pro Ala Val Phe Phe Lys Ser Glu Ala Ile Val His Pro Asp Gln Val
                325                 330                 335

Val Gln Tyr Ile Gly Gln Asp Glu Cys Gln Ile Gly Tyr Asn Pro Leu
```

```
                   340                 345                 350
Gln Met Ala Leu Leu Trp Asn Thr Leu Ala Thr Arg Glu Val Asn Leu
            355                 360                 365
Leu His Gln Ala Leu Thr Tyr Arg His Asn Leu Pro Glu His Thr Ala
        370                 375                 380
Trp Val Asn Tyr Val Arg Ser His Asp Asp Ile Gly Trp Thr Phe Ala
385                 390                 395                 400
Asp Glu Asp Ala Ala Tyr Leu Gly Ile Ser Gly Tyr Asp His Arg Gln
                405                 410                 415
Phe Leu Asn Arg Phe Phe Val Asn Arg Phe Asp Gly Ser Phe Ala Arg
            420                 425                 430
Gly Val Pro Phe Gln Tyr Asn Pro Ser Thr Gly Asp Cys Arg Val Ser
        435                 440                 445
Gly Thr Ala Ala Ala Leu Val Gly Leu Ala Gln Asp Asp Pro His Ala
    450                 455                 460
Val Asp Arg Ile Lys Leu Leu Tyr Ser Ile Ala Leu Ser Thr Gly Gly
465                 470                 475                 480
Leu Pro Leu Ile Tyr Leu Gly Asp Glu Val Gly Thr Leu Asn Asp Asp
                485                 490                 495
Asp Trp Ser Gln Asp Ser Asn Lys Ser Asp Asp Ser Arg Trp Ala His
            500                 505                 510
Arg Pro Arg Tyr Asn Glu Ala Leu Tyr Ala Gln Arg Asn Asp Pro Ser
        515                 520                 525
Thr Ala Ala Gly Gln Ile Tyr Gln Asp Leu Arg His Met Ile Ala Val
    530                 535                 540
Arg Gln Ser Asn Pro Arg Phe Asp Gly Gly Arg Leu Val Thr Phe Asn
545                 550                 555                 560
Thr Asn Asn Lys His Ile Ile Gly Tyr Ile Arg Asn Asn Ala Leu Leu
                565                 570                 575
Ala Phe Gly Asn Phe Ser Glu Tyr Pro Gln Thr Val Thr Ala His Thr
            580                 585                 590
Leu Gln Ala Met Pro Phe Lys Ala His Asp Leu Ile Gly Gly Lys Thr
        595                 600                 605
Val Ser Leu Asn Gln Asp Leu Thr Leu Gln Pro Tyr Gln Val Met Trp
    610                 615                 620
Leu Glu Ile Ala
625

<210> SEQ ID NO 4
<211> LENGTH: 628
<212> TYPE: PRT
<213> ORGANISM: Neisseria polysaccharea
<220> FEATURE:
<221> NAME/KEY: VARIANT
<222> LOCATION: 229
<223> OTHER INFORMATION: Xaa est choisi parmi A, C, D, E, G, H, I, K, L,
      M, N, P, Q, R, S, T, V, W et Y

<400> SEQUENCE: 4

Ser Pro Asn Ser Gln Tyr Leu Lys Thr Arg Ile Leu Asp Ile Tyr Thr
1               5                   10                  15
Pro Glu Gln Arg Ala Gly Ile Glu Lys Ser Glu Asp Trp Arg Gln Phe
                20                  25                  30
Ser Arg Arg Met Asp Thr His Phe Pro Lys Leu Met Asn Glu Leu Asp
            35                  40                  45
Ser Val Tyr Gly Asn Asn Glu Ala Leu Leu Pro Met Leu Glu Met Leu
```

```
            50                  55                  60
Leu Ala Gln Ala Trp Gln Ser Tyr Ser Gln Arg Asn Ser Ser Leu Lys
65                  70                  75                  80

Asp Ile Asp Ile Ala Arg Glu Asn Asn Pro Asp Trp Ile Leu Ser Asn
                    85                  90                  95

Lys Gln Val Gly Gly Val Cys Tyr Val Asp Leu Phe Ala Gly Asp Leu
                100                 105                 110

Lys Gly Leu Lys Asp Lys Ile Pro Tyr Phe Gln Glu Leu Gly Leu Thr
                115                 120                 125

Tyr Leu His Leu Met Pro Leu Phe Lys Cys Pro Glu Gly Lys Ser Asp
130                 135                 140

Gly Gly Tyr Ala Val Ser Ser Tyr Arg Asp Val Asn Pro Ala Leu Gly
145                 150                 155                 160

Thr Ile Gly Asp Leu Arg Glu Val Ile Ala Ala Leu His Glu Ala Gly
                165                 170                 175

Ile Ser Ala Val Val Asp Phe Ile Phe Asn His Thr Ser Asn Glu His
                180                 185                 190

Glu Trp Ala Gln Arg Cys Ala Ala Gly Asp Pro Leu Phe Asp Asn Phe
            195                 200                 205

Tyr Tyr Ile Phe Pro Asp Arg Arg Met Pro Asp Gln Tyr Asp Arg Thr
210                 215                 220

Leu Arg Glu Ile Xaa Pro Asp Gln His Pro Gly Gly Phe Ser Gln Leu
225                 230                 235                 240

Glu Asp Gly Arg Trp Val Trp Thr Thr Phe Asn Ser Phe Gln Trp Asp
                245                 250                 255

Leu Asn Tyr Ser Asn Pro Trp Val Phe Arg Ala Met Ala Gly Glu Met
                260                 265                 270

Leu Phe Leu Ala Asn Leu Gly Val Asp Ile Leu Arg Met Asp Ala Val
            275                 280                 285

Ala Phe Ile Trp Lys Gln Met Gly Thr Ser Cys Glu Asn Leu Pro Gln
290                 295                 300

Ala His Ala Leu Ile Arg Ala Phe Asn Ala Val Met Arg Ile Ala Ala
305                 310                 315                 320

Pro Ala Val Phe Phe Lys Ser Glu Ala Ile Val His Pro Asp Gln Val
                325                 330                 335

Val Gln Tyr Ile Gly Gln Asp Glu Cys Gln Ile Gly Tyr Asn Pro Leu
                340                 345                 350

Gln Met Ala Leu Leu Trp Asn Thr Leu Ala Thr Arg Glu Val Asn Leu
            355                 360                 365

Leu His Gln Ala Leu Thr Tyr Arg His Asn Leu Pro Glu His Thr Ala
370                 375                 380

Trp Val Asn Tyr Val Arg Ser His Asp Asp Ile Gly Trp Thr Phe Ala
385                 390                 395                 400

Asp Glu Asp Ala Ala Tyr Leu Gly Ile Ser Gly Tyr Asp His Arg Gln
                405                 410                 415

Phe Leu Asn Arg Phe Phe Val Asn Arg Phe Asp Gly Ser Phe Ala Arg
            420                 425                 430

Gly Val Pro Phe Gln Tyr Asn Pro Ser Thr Gly Asp Cys Arg Val Ser
                435                 440                 445

Gly Thr Ala Ala Leu Val Gly Leu Ala Gln Asp Asp Pro His Ala
                450                 455                 460

Val Asp Arg Ile Lys Leu Leu Tyr Ser Ile Ala Leu Ser Thr Gly Gly
465                 470                 475                 480
```

```
Leu Pro Leu Ile Tyr Leu Gly Asp Glu Val Gly Thr Leu Asn Asp Asp
                485                 490                 495

Asp Trp Ser Gln Asp Ser Asn Lys Ser Asp Asp Ser Arg Trp Ala His
            500                 505                 510

Arg Pro Arg Tyr Asn Glu Ala Leu Tyr Ala Gln Arg Asn Asp Pro Ser
        515                 520                 525

Thr Ala Ala Gly Gln Ile Tyr Gln Asp Leu Arg His Met Ile Ala Val
    530                 535                 540

Arg Gln Ser Asn Pro Arg Phe Asp Gly Gly Arg Leu Val Thr Phe Asn
545                 550                 555                 560

Thr Asn Asn Lys His Ile Ile Gly Tyr Ile Arg Asn Asn Ala Leu Leu
                565                 570                 575

Ala Phe Gly Asn Phe Ser Glu Tyr Pro Gln Thr Val Thr Ala His Thr
            580                 585                 590

Leu Gln Ala Met Pro Phe Lys Ala His Asp Leu Ile Gly Gly Lys Thr
        595                 600                 605

Val Ser Leu Asn Gln Asp Leu Thr Leu Gln Pro Tyr Gln Val Met Trp
    610                 615                 620

Leu Glu Ile Ala
625

<210> SEQ ID NO 5
<211> LENGTH: 628
<212> TYPE: PRT
<213> ORGANISM: Neisseria polysaccharea
<220> FEATURE:
<221> NAME/KEY: VARIANT
<222> LOCATION: 289
<223> OTHER INFORMATION: Xaa est choisi parmi C, D, E, F, G, H, I, K, L,
      M, N, P, Q, R, S, T, V, W et Y

<400> SEQUENCE: 5

Ser Pro Asn Ser Gln Tyr Leu Lys Thr Arg Ile Leu Asp Ile Tyr Thr
1               5                   10                  15

Pro Glu Gln Arg Ala Gly Ile Glu Lys Ser Glu Asp Trp Arg Gln Phe
            20                  25                  30

Ser Arg Arg Met Asp Thr His Phe Pro Lys Leu Met Asn Glu Leu Asp
        35                  40                  45

Ser Val Tyr Gly Asn Asn Glu Ala Leu Leu Pro Met Leu Glu Met Leu
    50                  55                  60

Leu Ala Gln Ala Trp Gln Ser Tyr Ser Gln Arg Asn Ser Ser Leu Lys
65                  70                  75                  80

Asp Ile Asp Ile Ala Arg Glu Asn Asn Pro Asp Trp Ile Leu Ser Asn
                85                  90                  95

Lys Gln Val Gly Gly Val Cys Tyr Val Asp Leu Phe Ala Gly Asp Leu
            100                 105                 110

Lys Gly Leu Lys Asp Lys Ile Pro Tyr Phe Gln Glu Leu Gly Leu Thr
        115                 120                 125

Tyr Leu His Leu Met Pro Leu Phe Lys Cys Pro Glu Gly Lys Ser Asp
    130                 135                 140

Gly Gly Tyr Ala Val Ser Ser Tyr Arg Asp Val Asn Pro Ala Leu Gly
145                 150                 155                 160

Thr Ile Gly Asp Leu Arg Glu Val Ile Ala Ala Leu His Glu Ala Gly
                165                 170                 175

Ile Ser Ala Val Val Asp Phe Ile Phe Asn His Thr Ser Asn Glu His
            180                 185                 190
```

```
Glu Trp Ala Gln Arg Cys Ala Ala Gly Asp Pro Leu Phe Asp Asn Phe
        195                 200                 205

Tyr Tyr Ile Phe Pro Asp Arg Met Pro Asp Gln Tyr Asp Arg Thr
    210                 215                 220

Leu Arg Glu Ile Phe Pro Asp Gln His Pro Gly Gly Phe Ser Gln Leu
225                 230                 235                 240

Glu Asp Gly Arg Trp Val Trp Thr Thr Phe Asn Ser Phe Gln Trp Asp
                245                 250                 255

Leu Asn Tyr Ser Asn Pro Trp Val Phe Arg Ala Met Ala Gly Glu Met
                260                 265                 270

Leu Phe Leu Ala Asn Leu Gly Val Asp Ile Leu Arg Met Asp Ala Val
            275                 280                 285

Xaa Phe Ile Trp Lys Gln Met Gly Thr Ser Cys Glu Asn Leu Pro Gln
    290                 295                 300

Ala His Ala Leu Ile Arg Ala Phe Asn Ala Val Met Arg Ile Ala Ala
305                 310                 315                 320

Pro Ala Val Phe Phe Lys Ser Glu Ala Ile Val His Pro Asp Gln Val
                325                 330                 335

Val Gln Tyr Ile Gly Gln Asp Glu Cys Gln Ile Gly Tyr Asn Pro Leu
                340                 345                 350

Gln Met Ala Leu Leu Trp Asn Thr Leu Ala Thr Arg Glu Val Asn Leu
            355                 360                 365

Leu His Gln Ala Leu Thr Tyr Arg His Asn Leu Pro Glu His Thr Ala
    370                 375                 380

Trp Val Asn Tyr Val Arg Ser His Asp Asp Ile Gly Trp Thr Phe Ala
385                 390                 395                 400

Asp Glu Asp Ala Ala Tyr Leu Gly Ile Ser Gly Tyr Asp His Arg Gln
                405                 410                 415

Phe Leu Asn Arg Phe Phe Val Asn Arg Phe Asp Gly Ser Phe Ala Arg
                420                 425                 430

Gly Val Pro Phe Gln Tyr Asn Pro Ser Thr Gly Asp Cys Arg Val Ser
            435                 440                 445

Gly Thr Ala Ala Ala Leu Val Gly Leu Ala Gln Asp Asp Pro His Ala
    450                 455                 460

Val Asp Arg Ile Lys Leu Leu Tyr Ser Ile Ala Leu Ser Thr Gly Gly
465                 470                 475                 480

Leu Pro Leu Ile Tyr Leu Gly Asp Glu Val Gly Thr Leu Asn Asp Asp
                485                 490                 495

Asp Trp Ser Gln Asp Ser Asn Lys Ser Asp Ser Arg Trp Ala His
                500                 505                 510

Arg Pro Arg Tyr Asn Glu Ala Leu Tyr Ala Gln Arg Asn Asp Pro Ser
    515                 520                 525

Thr Ala Ala Gly Gln Ile Tyr Gln Asp Leu Arg His Met Ile Ala Val
530                 535                 540

Arg Gln Ser Asn Pro Arg Phe Asp Gly Gly Arg Leu Val Thr Phe Asn
545                 550                 555                 560

Thr Asn Asn Lys His Ile Ile Gly Tyr Ile Arg Asn Asn Ala Leu Leu
                565                 570                 575

Ala Phe Gly Asn Phe Ser Glu Tyr Pro Gln Thr Val Thr Ala His Thr
            580                 585                 590

Leu Gln Ala Met Pro Phe Lys Ala His Asp Leu Ile Gly Gly Lys Thr
    595                 600                 605
```

```
Val Ser Leu Asn Gln Asp Leu Thr Leu Gln Pro Tyr Gln Val Met Trp
    610                 615                 620

Leu Glu Ile Ala
625

<210> SEQ ID NO 6
<211> LENGTH: 628
<212> TYPE: PRT
<213> ORGANISM: Neisseria polysaccharea
<220> FEATURE:
<221> NAME/KEY: VARIANT
<222> LOCATION: 290
<223> OTHER INFORMATION: Xaa est choisi parmi A, C, D, E, G, H, I, K, L,
      M, N, P, Q, R, S, T, V, W et Y

<400> SEQUENCE: 6

Ser Pro Asn Ser Gln Tyr Leu Lys Thr Arg Ile Leu Asp Ile Tyr Thr
1               5                   10                  15

Pro Glu Gln Arg Ala Gly Ile Glu Lys Ser Glu Asp Trp Arg Gln Phe
            20                  25                  30

Ser Arg Arg Met Asp Thr His Phe Pro Lys Leu Met Asn Glu Leu Asp
        35                  40                  45

Ser Val Tyr Gly Asn Asn Glu Ala Leu Leu Pro Met Leu Glu Met Leu
    50                  55                  60

Leu Ala Gln Ala Trp Gln Ser Tyr Ser Gln Arg Asn Ser Ser Leu Lys
65                  70                  75                  80

Asp Ile Asp Ile Ala Arg Glu Asn Asn Pro Asp Trp Ile Leu Ser Asn
                85                  90                  95

Lys Gln Val Gly Gly Val Cys Tyr Val Asp Leu Phe Ala Gly Asp Leu
            100                 105                 110

Lys Gly Leu Lys Asp Lys Ile Pro Tyr Phe Gln Glu Leu Gly Leu Thr
        115                 120                 125

Tyr Leu His Leu Met Pro Leu Phe Lys Cys Pro Glu Gly Lys Ser Asp
    130                 135                 140

Gly Gly Tyr Ala Val Ser Ser Tyr Arg Asp Val Asn Pro Ala Leu Gly
145                 150                 155                 160

Thr Ile Gly Asp Leu Arg Glu Val Ile Ala Ala Leu His Glu Ala Gly
                165                 170                 175

Ile Ser Ala Val Val Asp Phe Ile Phe Asn His Thr Ser Asn Glu His
            180                 185                 190

Glu Trp Ala Gln Arg Cys Ala Ala Gly Asp Pro Leu Phe Asp Asn Phe
        195                 200                 205

Tyr Tyr Ile Phe Pro Asp Arg Arg Met Pro Asp Gln Tyr Asp Arg Thr
    210                 215                 220

Leu Arg Glu Ile Phe Pro Asp Gln His Pro Gly Gly Phe Ser Gln Leu
225                 230                 235                 240

Glu Asp Gly Arg Trp Val Trp Thr Thr Phe Asn Ser Phe Gln Trp Asp
                245                 250                 255

Leu Asn Tyr Ser Asn Pro Trp Val Phe Arg Ala Met Ala Gly Glu Met
            260                 265                 270

Leu Phe Leu Ala Asn Leu Gly Val Asp Ile Leu Arg Met Asp Ala Val
        275                 280                 285

Ala Xaa Ile Trp Lys Gln Met Gly Thr Ser Cys Glu Asn Leu Pro Gln
    290                 295                 300

Ala His Ala Leu Ile Arg Ala Phe Asn Ala Val Met Arg Ile Ala Ala
305                 310                 315                 320
```

-continued

Pro Ala Val Phe Phe Lys Ser Glu Ala Ile Val His Pro Asp Gln Val
                325                 330                 335

Val Gln Tyr Ile Gly Gln Asp Glu Cys Gln Ile Gly Tyr Asn Pro Leu
            340                 345                 350

Gln Met Ala Leu Leu Trp Asn Thr Leu Ala Thr Arg Glu Val Asn Leu
        355                 360                 365

Leu His Gln Ala Leu Thr Tyr Arg His Asn Leu Pro Glu His Thr Ala
    370                 375                 380

Trp Val Asn Tyr Val Arg Ser His Asp Asp Ile Gly Trp Thr Phe Ala
385                 390                 395                 400

Asp Glu Asp Ala Ala Tyr Leu Gly Ile Ser Gly Tyr Asp His Arg Gln
                405                 410                 415

Phe Leu Asn Arg Phe Phe Val Asn Arg Phe Asp Gly Ser Phe Ala Arg
            420                 425                 430

Gly Val Pro Phe Gln Tyr Asn Pro Ser Thr Gly Asp Cys Arg Val Ser
        435                 440                 445

Gly Thr Ala Ala Ala Leu Val Gly Leu Ala Gln Asp Asp Pro His Ala
    450                 455                 460

Val Asp Arg Ile Lys Leu Leu Tyr Ser Ile Ala Leu Ser Thr Gly Gly
465                 470                 475                 480

Leu Pro Leu Ile Tyr Leu Gly Asp Glu Val Gly Thr Leu Asn Asp Asp
                485                 490                 495

Asp Trp Ser Gln Asp Ser Asn Lys Ser Asp Asp Ser Arg Trp Ala His
            500                 505                 510

Arg Pro Arg Tyr Asn Glu Ala Leu Tyr Ala Gln Arg Asn Asp Pro Ser
        515                 520                 525

Thr Ala Ala Gly Gln Ile Tyr Gln Asp Leu Arg His Met Ile Ala Val
    530                 535                 540

Arg Gln Ser Asn Pro Arg Phe Asp Gly Gly Arg Leu Val Thr Phe Asn
545                 550                 555                 560

Thr Asn Asn Lys His Ile Ile Gly Tyr Ile Arg Asn Asn Ala Leu Leu
                565                 570                 575

Ala Phe Gly Asn Phe Ser Glu Tyr Pro Gln Thr Val Thr Ala His Thr
            580                 585                 590

Leu Gln Ala Met Pro Phe Lys Ala His Asp Leu Ile Gly Gly Lys Thr
        595                 600                 605

Val Ser Leu Asn Gln Asp Leu Thr Leu Gln Pro Tyr Gln Val Met Trp
    610                 615                 620

Leu Glu Ile Ala
625

<210> SEQ ID NO 7
<211> LENGTH: 628
<212> TYPE: PRT
<213> ORGANISM: Neisseria polysaccharea
<220> FEATURE:
<221> NAME/KEY: VARIANT
<222> LOCATION: 330
<223> OTHER INFORMATION: Xaa est choisi parmi A, C, D, E, F, G, H, K, L,
      M, N, P, Q, R, S, T, V, W et Y

<400> SEQUENCE: 7

Ser Pro Asn Ser Gln Tyr Leu Lys Thr Arg Ile Leu Asp Ile Tyr Thr
1               5                   10                  15

Pro Glu Gln Arg Ala Gly Ile Glu Lys Ser Glu Asp Trp Arg Gln Phe
            20                  25                  30

```
Ser Arg Arg Met Asp Thr His Phe Pro Lys Leu Met Asn Glu Leu Asp
        35                  40                  45
Ser Val Tyr Gly Asn Asn Glu Ala Leu Leu Pro Met Leu Glu Met Leu
 50                  55                  60
Leu Ala Gln Ala Trp Gln Ser Tyr Ser Gln Arg Asn Ser Ser Leu Lys
 65                  70                  75                  80
Asp Ile Asp Ile Ala Arg Glu Asn Asn Pro Asp Trp Ile Leu Ser Asn
                 85                  90                  95
Lys Gln Val Gly Val Cys Tyr Val Asp Leu Phe Ala Gly Asp Leu
                100                 105                 110
Lys Gly Leu Lys Asp Lys Ile Pro Tyr Phe Gln Glu Leu Gly Leu Thr
            115                 120                 125
Tyr Leu His Leu Met Pro Leu Phe Lys Cys Pro Glu Gly Lys Ser Asp
130                 135                 140
Gly Gly Tyr Ala Val Ser Ser Tyr Arg Asp Val Asn Pro Ala Leu Gly
145                 150                 155                 160
Thr Ile Gly Asp Leu Arg Glu Val Ile Ala Ala Leu His Glu Ala Gly
                165                 170                 175
Ile Ser Ala Val Val Asp Phe Ile Phe Asn His Thr Ser Asn Glu His
            180                 185                 190
Glu Trp Ala Gln Arg Cys Ala Ala Gly Asp Pro Leu Phe Asp Asn Phe
        195                 200                 205
Tyr Tyr Ile Phe Pro Asp Arg Met Pro Asp Gln Tyr Asp Arg Thr
    210                 215                 220
Leu Arg Glu Ile Phe Pro Asp Gln His Pro Gly Gly Phe Ser Gln Leu
225                 230                 235                 240
Glu Asp Gly Arg Trp Val Trp Thr Thr Phe Asn Ser Phe Gln Trp Asp
                245                 250                 255
Leu Asn Tyr Ser Asn Pro Trp Val Phe Arg Ala Met Ala Gly Glu Met
            260                 265                 270
Leu Phe Leu Ala Asn Leu Gly Val Asp Ile Leu Arg Met Asp Ala Val
        275                 280                 285
Ala Phe Ile Trp Lys Gln Met Gly Thr Ser Cys Glu Asn Leu Pro Gln
    290                 295                 300
Ala His Ala Leu Ile Arg Ala Phe Asn Ala Val Met Arg Ile Ala Ala
305                 310                 315                 320
Pro Ala Val Phe Phe Lys Ser Glu Ala Xaa Val His Pro Asp Gln Val
                325                 330                 335
Val Gln Tyr Ile Gly Gln Asp Glu Cys Gln Ile Gly Tyr Asn Pro Leu
            340                 345                 350
Gln Met Ala Leu Leu Trp Asn Thr Leu Ala Thr Arg Glu Val Asn Leu
        355                 360                 365
Leu His Gln Ala Leu Thr Tyr Arg His Asn Leu Pro Glu His Thr Ala
    370                 375                 380
Trp Val Asn Tyr Val Arg Ser His Asp Asp Ile Gly Trp Thr Phe Ala
385                 390                 395                 400
Asp Glu Asp Ala Ala Tyr Leu Gly Ile Ser Gly Tyr Asp His Arg Gln
                405                 410                 415
Phe Leu Asn Arg Phe Val Asn Arg Phe Asp Gly Ser Phe Ala Arg
            420                 425                 430
Gly Val Pro Phe Gln Tyr Asn Pro Ser Thr Gly Asp Cys Arg Val Ser
        435                 440                 445
Gly Thr Ala Ala Ala Leu Val Gly Leu Ala Gln Asp Asp Pro His Ala
```

-continued

```
                450                 455                 460
Val Asp Arg Ile Lys Leu Leu Tyr Ser Ile Ala Leu Ser Thr Gly Gly
465                 470                 475                 480

Leu Pro Leu Ile Tyr Leu Gly Asp Glu Val Gly Thr Leu Asn Asp Asp
                485                 490                 495

Asp Trp Ser Gln Asp Ser Asn Lys Ser Asp Asp Ser Arg Trp Ala His
                500                 505                 510

Arg Pro Arg Tyr Asn Glu Ala Leu Tyr Ala Gln Arg Asn Asp Pro Ser
                515                 520                 525

Thr Ala Ala Gly Gln Ile Tyr Gln Asp Leu Arg His Met Ile Ala Val
                530                 535                 540

Arg Gln Ser Asn Pro Arg Phe Asp Gly Gly Arg Leu Val Thr Phe Asn
545                 550                 555                 560

Thr Asn Asn Lys His Ile Ile Gly Tyr Ile Arg Asn Asn Ala Leu Leu
                565                 570                 575

Ala Phe Gly Asn Phe Ser Glu Tyr Pro Gln Thr Val Thr Ala His Thr
                580                 585                 590

Leu Gln Ala Met Pro Phe Lys Ala His Asp Leu Ile Gly Gly Lys Thr
                595                 600                 605

Val Ser Leu Asn Gln Asp Leu Thr Leu Gln Pro Tyr Gln Val Met Trp
610                 615                 620

Leu Glu Ile Ala
625

<210> SEQ ID NO 8
<211> LENGTH: 628
<212> TYPE: PRT
<213> ORGANISM: Neisseria polysaccharea
<220> FEATURE:
<221> NAME/KEY: VARIANT
<222> LOCATION: 331
<223> OTHER INFORMATION: Xaa est choisi parmi A, C, D, E, F, G, H, I, K,
      L, M, N, P, Q, R, S, T, W et Y

<400> SEQUENCE: 8

Ser Pro Asn Ser Gln Tyr Leu Lys Thr Arg Ile Leu Asp Ile Tyr Thr
1               5                   10                  15

Pro Glu Gln Arg Ala Gly Ile Glu Lys Ser Glu Asp Trp Arg Gln Phe
                20                  25                  30

Ser Arg Arg Met Asp Thr His Phe Pro Lys Leu Met Asn Glu Leu Asp
                35                  40                  45

Ser Val Tyr Gly Asn Asn Glu Ala Leu Leu Pro Met Leu Glu Met Leu
                50                  55                  60

Leu Ala Gln Ala Trp Gln Ser Tyr Ser Gln Arg Asn Ser Ser Leu Lys
65                  70                  75                  80

Asp Ile Asp Ile Ala Arg Glu Asn Asn Pro Asp Trp Ile Leu Ser Asn
                85                  90                  95

Lys Gln Val Gly Gly Val Cys Tyr Val Asp Leu Phe Ala Gly Asp Leu
                100                 105                 110

Lys Gly Leu Lys Asp Lys Ile Pro Tyr Phe Gln Glu Leu Gly Leu Thr
                115                 120                 125

Tyr Leu His Leu Met Pro Leu Phe Lys Cys Pro Glu Gly Lys Ser Asp
                130                 135                 140

Gly Gly Tyr Ala Val Ser Ser Tyr Arg Asp Val Asn Pro Ala Leu Gly
145                 150                 155                 160

Thr Ile Gly Asp Leu Arg Glu Val Ile Ala Ala Leu His Glu Ala Gly
```

```
            165                 170                 175
Ile Ser Ala Val Val Asp Phe Ile Phe Asn His Thr Ser Asn Glu His
            180                 185                 190

Glu Trp Ala Gln Arg Cys Ala Ala Gly Asp Pro Leu Phe Asp Asn Phe
            195                 200                 205

Tyr Tyr Ile Phe Pro Asp Arg Arg Met Pro Asp Gln Tyr Asp Arg Thr
            210                 215                 220

Leu Arg Glu Ile Phe Pro Asp Gln His Pro Gly Gly Phe Ser Gln Leu
225                 230                 235                 240

Glu Asp Gly Arg Trp Val Trp Thr Thr Phe Asn Ser Phe Gln Trp Asp
                245                 250                 255

Leu Asn Tyr Ser Asn Pro Trp Val Phe Arg Ala Met Ala Gly Glu Met
                260                 265                 270

Leu Phe Leu Ala Asn Leu Gly Val Asp Ile Leu Arg Met Asp Ala Val
                275                 280                 285

Ala Phe Ile Trp Lys Gln Met Gly Thr Ser Cys Glu Asn Leu Pro Gln
        290                 295                 300

Ala His Ala Leu Ile Arg Ala Phe Asn Ala Val Met Arg Ile Ala Ala
305                 310                 315                 320

Pro Ala Val Phe Phe Lys Ser Glu Ala Ile Xaa His Pro Asp Gln Val
                325                 330                 335

Val Gln Tyr Ile Gly Gln Asp Glu Cys Gln Ile Gly Tyr Asn Pro Leu
                340                 345                 350

Gln Met Ala Leu Leu Trp Asn Thr Leu Ala Thr Arg Glu Val Asn Leu
                355                 360                 365

Leu His Gln Ala Leu Thr Tyr Arg His Asn Leu Pro Glu His Thr Ala
        370                 375                 380

Trp Val Asn Tyr Val Arg Ser His Asp Asp Ile Gly Trp Thr Phe Ala
385                 390                 395                 400

Asp Glu Asp Ala Ala Tyr Leu Gly Ile Ser Gly Tyr Asp His Arg Gln
                405                 410                 415

Phe Leu Asn Arg Phe Phe Val Asn Arg Phe Asp Gly Ser Phe Ala Arg
                420                 425                 430

Gly Val Pro Phe Gln Tyr Asn Pro Ser Thr Gly Asp Cys Arg Val Ser
                435                 440                 445

Gly Thr Ala Ala Ala Leu Val Gly Leu Ala Gln Asp Asp Pro His Ala
        450                 455                 460

Val Asp Arg Ile Lys Leu Leu Tyr Ser Ile Ala Leu Ser Thr Gly Gly
465                 470                 475                 480

Leu Pro Leu Ile Tyr Leu Gly Asp Glu Val Gly Thr Leu Asn Asp Asp
                485                 490                 495

Asp Trp Ser Gln Asp Ser Asn Lys Ser Asp Asp Ser Arg Trp Ala His
                500                 505                 510

Arg Pro Arg Tyr Asn Glu Ala Leu Tyr Ala Gln Arg Asn Asp Pro Ser
        515                 520                 525

Thr Ala Ala Gly Gln Ile Tyr Gln Asp Leu Arg His Met Ile Ala Val
        530                 535                 540

Arg Gln Ser Asn Pro Arg Phe Asp Gly Arg Leu Val Thr Phe Asn
545                 550                 555                 560

Thr Asn Asn Lys His Ile Ile Gly Tyr Ile Arg Asn Asn Ala Leu Leu
                565                 570                 575

Ala Phe Gly Asn Phe Ser Glu Tyr Pro Gln Thr Val Thr Ala His Thr
                580                 585                 590
```

```
Leu Gln Ala Met Pro Phe Lys Ala His Asp Leu Ile Gly Gly Lys Thr
            595                 600                 605

Val Ser Leu Asn Gln Asp Leu Thr Leu Gln Pro Tyr Gln Val Met Trp
        610                 615                 620

Leu Glu Ile Ala
625

<210> SEQ ID NO 9
<211> LENGTH: 628
<212> TYPE: PRT
<213> ORGANISM: Neisseria polysaccharea
<220> FEATURE:
<221> NAME/KEY: VARIANT
<222> LOCATION: 394
<223> OTHER INFORMATION: Xaa est choisi parmi A, C, E, F, G, H, I, K, L,
      M, N, P, Q, R, S, T, V, W et Y

<400> SEQUENCE: 9

Ser Pro Asn Ser Gln Tyr Leu Lys Thr Arg Ile Leu Asp Ile Tyr Thr
1               5                   10                  15

Pro Glu Gln Arg Ala Gly Ile Glu Lys Ser Glu Asp Trp Arg Gln Phe
            20                  25                  30

Ser Arg Arg Met Asp Thr His Phe Pro Lys Leu Met Asn Glu Leu Asp
        35                  40                  45

Ser Val Tyr Gly Asn Asn Glu Ala Leu Leu Pro Met Leu Glu Met Leu
    50                  55                  60

Leu Ala Gln Ala Trp Gln Ser Tyr Ser Gln Arg Asn Ser Ser Leu Lys
65                  70                  75                  80

Asp Ile Asp Ile Ala Arg Glu Asn Asn Pro Asp Trp Ile Leu Ser Asn
                85                  90                  95

Lys Gln Val Gly Gly Val Cys Tyr Val Asp Leu Phe Ala Gly Asp Leu
            100                 105                 110

Lys Gly Leu Lys Asp Lys Ile Pro Tyr Phe Gln Glu Leu Gly Leu Thr
        115                 120                 125

Tyr Leu His Leu Met Pro Leu Phe Lys Cys Pro Glu Gly Lys Ser Asp
    130                 135                 140

Gly Gly Tyr Ala Val Ser Ser Tyr Arg Asp Val Asn Pro Ala Leu Gly
145                 150                 155                 160

Thr Ile Gly Asp Leu Arg Glu Val Ile Ala Ala Leu His Glu Ala Gly
                165                 170                 175

Ile Ser Ala Val Val Asp Phe Ile Phe Asn His Thr Ser Asn Glu His
            180                 185                 190

Glu Trp Ala Gln Arg Cys Ala Ala Gly Asp Pro Leu Phe Asp Asn Phe
        195                 200                 205

Tyr Tyr Ile Phe Pro Asp Arg Arg Met Pro Asp Gln Tyr Asp Arg Thr
    210                 215                 220

Leu Arg Glu Ile Phe Pro Asp Gln His Pro Gly Gly Phe Ser Gln Leu
225                 230                 235                 240

Glu Asp Gly Arg Trp Val Trp Thr Thr Phe Asn Ser Phe Gln Trp Asp
                245                 250                 255

Leu Asn Tyr Ser Asn Pro Trp Val Phe Arg Ala Met Ala Gly Glu Met
            260                 265                 270

Leu Phe Leu Ala Asn Leu Gly Val Asp Ile Leu Arg Met Asp Ala Val
        275                 280                 285

Ala Phe Ile Trp Lys Gln Met Gly Thr Ser Cys Glu Asn Leu Pro Gln
    290                 295                 300
```

Ala His Ala Leu Ile Arg Ala Phe Asn Ala Val Met Arg Ile Ala Ala
305                 310                 315                 320

Pro Ala Val Phe Phe Lys Ser Glu Ala Ile Val His Pro Asp Gln Val
            325                 330                 335

Val Gln Tyr Ile Gly Gln Asp Glu Cys Gln Ile Gly Tyr Asn Pro Leu
        340                 345                 350

Gln Met Ala Leu Leu Trp Asn Thr Leu Ala Thr Arg Glu Val Asn Leu
            355                 360                 365

Leu His Gln Ala Leu Thr Tyr Arg His Asn Leu Pro Glu His Thr Ala
    370                 375                 380

Trp Val Asn Tyr Val Arg Ser His Asp Xaa Ile Gly Trp Thr Phe Ala
385                 390                 395                 400

Asp Glu Asp Ala Ala Tyr Leu Gly Ile Ser Gly Tyr Asp His Arg Gln
                405                 410                 415

Phe Leu Asn Arg Phe Phe Val Asn Arg Phe Asp Gly Ser Phe Ala Arg
            420                 425                 430

Gly Val Pro Phe Gln Tyr Asn Pro Ser Thr Gly Asp Cys Arg Val Ser
        435                 440                 445

Gly Thr Ala Ala Ala Leu Val Gly Leu Ala Gln Asp Asp Pro His Ala
    450                 455                 460

Val Asp Arg Ile Lys Leu Leu Tyr Ser Ile Ala Leu Ser Thr Gly Gly
465                 470                 475                 480

Leu Pro Leu Ile Tyr Leu Gly Asp Glu Val Gly Thr Leu Asn Asp Asp
                485                 490                 495

Asp Trp Ser Gln Asp Ser Asn Lys Ser Asp Asp Ser Arg Trp Ala His
            500                 505                 510

Arg Pro Arg Tyr Asn Glu Ala Leu Tyr Ala Gln Arg Asn Asp Pro Ser
        515                 520                 525

Thr Ala Ala Gly Gln Ile Tyr Gln Asp Leu Arg His Met Ile Ala Val
    530                 535                 540

Arg Gln Ser Asn Pro Arg Phe Asp Gly Gly Arg Leu Val Thr Phe Asn
545                 550                 555                 560

Thr Asn Asn Lys His Ile Ile Gly Tyr Ile Arg Asn Asn Ala Leu Leu
                565                 570                 575

Ala Phe Gly Asn Phe Ser Glu Tyr Pro Gln Thr Val Thr Ala His Thr
            580                 585                 590

Leu Gln Ala Met Pro Phe Lys Ala His Asp Leu Ile Gly Gly Lys Thr
        595                 600                 605

Val Ser Leu Asn Gln Asp Leu Thr Leu Gln Pro Tyr Gln Val Met Trp
    610                 615                 620

Leu Glu Ile Ala
625

<210> SEQ ID NO 10
<211> LENGTH: 628
<212> TYPE: PRT
<213> ORGANISM: Neisseria polysaccharea
<220> FEATURE:
<221> NAME/KEY: VARIANT
<222> LOCATION: 446
<223> OTHER INFORMATION: Xaa est choisi parmi A, C, D, E, F, G, H, I, K,
      L, M, N, Q, S, T, V, W et Y

<400> SEQUENCE: 10

Ser Pro Asn Ser Gln Tyr Leu Lys Thr Arg Ile Leu Asp Ile Tyr Thr
1               5                   10                  15

```
Pro Glu Gln Arg Ala Gly Ile Glu Lys Ser Glu Asp Trp Arg Gln Phe
            20                  25                  30

Ser Arg Arg Met Asp Thr His Phe Pro Lys Leu Met Asn Glu Leu Asp
        35                  40                  45

Ser Val Tyr Gly Asn Asn Glu Ala Leu Leu Pro Met Leu Glu Met Leu
    50                  55                  60

Leu Ala Gln Ala Trp Gln Ser Tyr Ser Gln Arg Asn Ser Ser Leu Lys
65                  70                  75                  80

Asp Ile Asp Ile Ala Arg Glu Asn Asn Pro Asp Trp Ile Leu Ser Asn
                85                  90                  95

Lys Gln Val Gly Gly Val Cys Tyr Val Asp Leu Phe Ala Gly Asp Leu
            100                 105                 110

Lys Gly Leu Lys Asp Lys Ile Pro Tyr Phe Gln Glu Leu Gly Leu Thr
        115                 120                 125

Tyr Leu His Leu Met Pro Leu Phe Lys Cys Pro Glu Gly Lys Ser Asp
    130                 135                 140

Gly Gly Tyr Ala Val Ser Ser Tyr Arg Asp Val Asn Pro Ala Leu Gly
145                 150                 155                 160

Thr Ile Gly Asp Leu Arg Glu Val Ile Ala Ala Leu His Glu Ala Gly
                165                 170                 175

Ile Ser Ala Val Val Asp Phe Ile Phe Asn His Thr Ser Asn Glu His
            180                 185                 190

Glu Trp Ala Gln Arg Cys Ala Ala Gly Asp Pro Leu Phe Asp Asn Phe
        195                 200                 205

Tyr Tyr Ile Phe Pro Asp Arg Arg Met Pro Asp Gln Tyr Asp Arg Thr
    210                 215                 220

Leu Arg Glu Ile Phe Pro Asp Gln His Pro Gly Gly Phe Ser Gln Leu
225                 230                 235                 240

Glu Asp Gly Arg Trp Val Trp Thr Thr Phe Asn Ser Phe Gln Trp Asp
                245                 250                 255

Leu Asn Tyr Ser Asn Pro Trp Val Phe Arg Ala Met Ala Gly Glu Met
            260                 265                 270

Leu Phe Leu Ala Asn Leu Gly Val Asp Ile Leu Arg Met Asp Ala Val
        275                 280                 285

Ala Phe Ile Trp Lys Gln Met Gly Thr Ser Cys Glu Asn Leu Pro Gln
    290                 295                 300

Ala His Ala Leu Ile Arg Ala Phe Asn Ala Val Met Arg Ile Ala Ala
305                 310                 315                 320

Pro Ala Val Phe Phe Lys Ser Glu Ala Ile Val His Pro Asp Gln Val
                325                 330                 335

Val Gln Tyr Ile Gly Gln Asp Gly Cys Gln Ile Gly Tyr Asn Pro Leu
            340                 345                 350

Gln Met Ala Leu Leu Trp Asn Thr Leu Ala Thr Arg Glu Val Asn Leu
        355                 360                 365

Leu His Gln Ala Leu Thr Tyr Arg His Asn Leu Pro Glu His Thr Ala
    370                 375                 380

Trp Val Asn Tyr Val Arg Ser His Asp Asp Ile Gly Trp Thr Phe Ala
385                 390                 395                 400

Asp Glu Asp Ala Ala Tyr Leu Gly Ile Ser Gly Tyr Asp His Arg Gln
                405                 410                 415

Phe Leu Asn Arg Phe Phe Val Asn Arg Phe Asp Gly Ser Phe Ala Arg
            420                 425                 430
```

-continued

```
Gly Val Pro Phe Gln Tyr Asn Pro Ser Thr Gly Asp Cys Xaa Val Ser
            435                 440                 445

Gly Thr Ala Ala Ala Leu Val Gly Leu Ala Gln Asp Asp Pro His Ala
        450                 455                 460

Val Asp Arg Ile Lys Leu Leu Tyr Ser Ile Ala Leu Ser Thr Gly Gly
465                 470                 475                 480

Leu Pro Leu Ile Tyr Leu Gly Asp Glu Val Gly Thr Leu Asn Asp Asp
                485                 490                 495

Asp Trp Ser Gln Asp Ser Asn Lys Ser Asp Asp Ser Arg Trp Ala His
            500                 505                 510

Arg Pro Arg Tyr Asn Glu Ala Leu Tyr Ala Gln Arg Asn Asp Pro Ser
        515                 520                 525

Thr Ala Ala Gly Gln Ile Tyr Gln Asp Leu Arg His Met Ile Ala Val
        530                 535                 540

Arg Gln Ser Asn Pro Arg Phe Asp Gly Gly Arg Leu Val Thr Phe Asn
545                 550                 555                 560

Thr Asn Asn Lys His Ile Ile Gly Tyr Ile Arg Asn Asn Ala Leu Leu
                565                 570                 575

Ala Phe Gly Asn Phe Ser Glu Tyr Pro Gln Thr Val Thr Ala His Thr
            580                 585                 590

Leu Gln Ala Met Pro Phe Lys Ala His Asp Leu Ile Gly Gly Lys Thr
        595                 600                 605

Val Ser Leu Asn Gln Asp Leu Thr Leu Gln Pro Tyr Gln Val Met Trp
610                 615                 620

Leu Glu Ile Ala
625

<210> SEQ ID NO 11
<211> LENGTH: 1299
<212> TYPE: PRT
<213> ORGANISM: Leuconostoc mesenteroides B-512F

<400> SEQUENCE: 11

Thr Gln Gln Val Ser Gly Lys Tyr Val Glu Lys Asp Gly Ser Trp Tyr
1               5                   10                  15

Tyr Tyr Phe Asp Asp Gly Lys Asn Ala Lys Gly Leu Ser Thr Ile Asp
                20                  25                  30

Asn Asn Ile Gln Tyr Phe Tyr Glu Ser Gly Lys Gln Ala Lys Gly Gln
            35                  40                  45

Tyr Val Thr Ile Asp Asn Gln Thr Tyr Tyr Phe Asp Lys Gly Ser Gly
        50                  55                  60

Asp Glu Leu Thr Gly Leu Gln Ser Ile Asp Gly Asn Ile Val Ala Phe
65                  70                  75                  80

Asn Asp Glu Gly Gln Gln Ile Phe Asn Gln Tyr Gln Ser Glu Asn
                85                  90                  95

Gly Thr Thr Tyr Tyr Phe Asp Asp Lys Gly His Ala Ala Thr Gly Ile
            100                 105                 110

Lys Asn Ile Glu Gly Lys Asn Tyr Tyr Phe Asp Asn Leu Gly Gln Leu
        115                 120                 125

Lys Lys Gly Phe Ser Gly Val Ile Asp Gly Gln Ile Met Thr Phe Asp
    130                 135                 140

Gln Glu Thr Gly Gln Glu Val Ser Asn Thr Thr Ser Glu Ile Lys Glu
145                 150                 155                 160

Gly Leu Thr Thr Gln Asn Thr Asp Tyr Ser Glu His Asn Ala Ala His
                165                 170                 175
```

-continued

Gly Thr Asp Ala Glu Asp Phe Glu Asn Ile Asp Gly Tyr Leu Thr Ala
            180                 185                 190

Ser Ser Trp Tyr Arg Pro Thr Gly Ile Leu Arg Asn Gly Thr Asp Trp
        195                 200                 205

Glu Pro Ser Thr Asp Thr Asp Phe Arg Pro Ile Leu Ser Val Trp Trp
    210                 215                 220

Pro Asp Lys Asn Thr Gln Val Asn Tyr Leu Asn Tyr Met Ala Asp Leu
225                 230                 235                 240

Gly Phe Ile Ser Asn Ala Asp Ser Phe Glu Thr Gly Asp Ser Gln Ser
                245                 250                 255

Leu Leu Asn Glu Ala Ser Asn Tyr Val Gln Lys Ser Ile Glu Met Lys
            260                 265                 270

Ile Ser Ala Gln Gln Ser Thr Glu Trp Leu Lys Asp Ala Met Ala Ala
        275                 280                 285

Phe Ile Val Ala Gln Pro Gln Trp Asn Glu Thr Ser Glu Asp Met Ser
    290                 295                 300

Asn Asp His Leu Gln Asn Gly Ala Leu Thr Tyr Val Asn Ser Pro Leu
305                 310                 315                 320

Thr Pro Asp Ala Asn Ser Asn Phe Arg Leu Leu Asn Arg Thr Pro Thr
                325                 330                 335

Asn Gln Thr Gly Glu Gln Ala Tyr Asn Leu Asp Asn Ser Lys Gly Gly
            340                 345                 350

Phe Glu Leu Leu Leu Ala Asn Gln Glu Asp Asn Ser Asn Val Val Val
        355                 360                 365

Glu Ala Glu Gln Leu Asn Trp Leu Tyr Tyr Leu Met Asn Phe Gly Thr
    370                 375                 380

Ile Thr Ala Asn Asp Ala Asp Ala Asn Phe Asp Gly Ile Arg Val Asp
385                 390                 395                 400

Ala Val Asp Asn Val Asp Ala Asp Leu Leu Gln Ile Ala Ala Asp Tyr
                405                 410                 415

Phe Lys Leu Ala Tyr Gly Val Asp Gln Asn Asp Ala Thr Ala Asn Gln
            420                 425                 430

His Leu Ser Ile Leu Glu Asp Trp Ser His Asn Asp Pro Leu Tyr Val
        435                 440                 445

Thr Asp Gln Gly Ser Asn Gln Leu Thr Met Asp Asp Tyr Val His Thr
    450                 455                 460

Gln Leu Ile Trp Ser Leu Thr Lys Ser Ser Asp Ile Arg Gly Thr Met
465                 470                 475                 480

Gln Arg Phe Val Asp Tyr Tyr Met Val Asp Arg Ser Asn Asp Ser Thr
                485                 490                 495

Glu Asn Glu Ala Ile Pro Asn Tyr Ser Phe Val Arg Ala His Asp Ser
            500                 505                 510

Glu Val Gln Thr Val Ile Ala Gln Ile Val Ser Asp Leu Tyr Pro Asp
        515                 520                 525

Val Glu Asn Ser Leu Ala Pro Thr Thr Glu Gln Leu Ala Ala Ala Phe
    530                 535                 540

Lys Val Tyr Asn Glu Asp Glu Lys Leu Ala Asp Lys Lys Tyr Thr Gln
545                 550                 555                 560

Tyr Asn Met Ala Ser Ala Tyr Ala Met Leu Leu Thr Asn Lys Asp Thr
                565                 570                 575

Val Pro Arg Val Tyr Tyr Gly Asp Leu Tyr Thr Asp Asp Gly Gln Tyr
            580                 585                 590

```
Met Ala Thr Lys Ser Pro Tyr Tyr Asp Ala Ile Asn Thr Leu Leu Lys
            595                 600                 605
Ala Arg Val Gln Tyr Val Ala Gly Gly Gln Ser Met Ser Val Asp Ser
    610                 615                 620
Asn Asp Val Leu Thr Ser Val Arg Tyr Gly Lys Asp Ala Met Thr Ala
625                 630                 635                 640
Ser Asp Thr Gly Thr Ser Glu Thr Arg Thr Glu Gly Ile Gly Val Ile
                645                 650                 655
Val Ser Asn Asn Ala Glu Leu Gln Leu Glu Asp Gly His Thr Val Thr
            660                 665                 670
Leu His Met Gly Ala Ala His Lys Asn Gln Ala Tyr Arg Ala Leu Leu
        675                 680                 685
Ser Thr Thr Ala Asp Gly Leu Ala Tyr Tyr Asp Thr Asp Glu Asn Ala
    690                 695                 700
Pro Val Ala Tyr Thr Asp Ala Asn Gly Asp Leu Ile Phe Thr Asn Glu
705                 710                 715                 720
Ser Ile Tyr Gly Val Gln Asn Pro Gln Val Ser Gly Tyr Leu Ala Val
                725                 730                 735
Trp Val Pro Val Gly Ala Gln Gln Asp Gln Asp Ala Arg Thr Ala Ser
            740                 745                 750
Asp Thr Thr Thr Asn Thr Ser Asp Lys Val Phe His Ser Asn Ala Ala
        755                 760                 765
Leu Asp Ser Gln Val Ile Tyr Glu Gly Phe Ser Asn Phe Gln Ala Phe
    770                 775                 780
Ala Thr Asp Ser Ser Glu Tyr Thr Asn Val Val Ile Ala Gln Asn Ala
785                 790                 795                 800
Asp Gln Phe Lys Gln Trp Gly Val Thr Ser Phe Gln Leu Ala Pro Gln
                805                 810                 815
Tyr Arg Ser Ser Thr Asp Thr Ser Phe Leu Asp Ser Ile Ile Gln Asn
            820                 825                 830
Gly Tyr Ala Phe Thr Asp Arg Tyr Asp Leu Gly Tyr Gly Thr Pro Thr
        835                 840                 845
Lys Tyr Gly Thr Ala Asp Gln Leu Arg Asp Ala Ile Lys Ala Leu His
    850                 855                 860
Ala Ser Gly Ile Gln Ala Ile Ala Asp Trp Val Pro Asp Gln Ile Tyr
865                 870                 875                 880
Asn Leu Pro Glu Gln Glu Leu Ala Thr Val Thr Arg Thr Asn Ser Phe
                885                 890                 895
Gly Asp Asp Asp Thr Asp Ser Asp Ile Asp Asn Ala Leu Tyr Val Val
            900                 905                 910
Gln Ser Arg Gly Gly Gly Gln Tyr Gln Glu Met Tyr Gly Gly Ala Phe
        915                 920                 925
Leu Glu Glu Leu Gln Ala Leu Tyr Pro Ser Leu Phe Lys Val Asn Gln
    930                 935                 940
Ile Ser Thr Gly Val Pro Ile Asp Gly Ser Val Lys Ile Thr Glu Trp
945                 950                 955                 960
Ala Ala Lys Tyr Phe Asn Gly Ser Asn Ile Gln Gly Lys Gly Ala Gly
                965                 970                 975
Tyr Val Leu Lys Asp Met Gly Ser Asn Lys Tyr Phe Lys Val Val Ser
            980                 985                 990
Asn Thr Glu Asp Gly Asp Tyr Leu Pro Lys Gln Leu Thr Asn Asp Leu
        995                 1000                1005
Ser Glu Thr Gly Phe Thr His Asp Asp Lys Gly Ile Ile Tyr Tyr Thr
```

```
                 1010                1015                1020

Leu Ser Gly Tyr Arg Ala Gln Asn Ala Phe Ile Gln Asp Asp Asn
1025                1030                1035                1040

Asn Tyr Tyr Tyr Phe Asp Lys Thr Gly His Leu Val Thr Gly Leu Gln
                    1045                1050                1055

Lys Ile Asn Asn His Thr Tyr Phe Phe Leu Pro Asn Gly Ile Glu Leu
                1060                1065                1070

Val Lys Ser Phe Leu Gln Asn Glu Asp Gly Thr Ile Val Tyr Phe Asp
            1075                1080                1085

Lys Lys Gly His Gln Val Phe Asp Gln Tyr Ile Thr Asp Gln Asn Gly
            1090                1095                1100

Asn Ala Tyr Tyr Phe Asp Asp Ala Gly Val Met Leu Lys Ser Gly Leu
1105                1110                1115                1120

Ala Thr Ile Asp Gly His Gln Gln Tyr Phe Asp Gln Asn Gly Val Gln
                1125                1130                1135

Val Lys Asp Lys Phe Val Ile Gly Thr Asp Gly Tyr Lys Tyr Tyr Phe
                1140                1145                1150

Glu Pro Gly Ser Gly Asn Leu Ala Ile Leu Arg Tyr Val Gln Asn Ser
            1155                1160                1165

Lys Asn Gln Trp Phe Tyr Phe Asp Gly Asn Gly His Ala Val Thr Gly
            1170                1175                1180

Phe Gln Thr Ile Asn Gly Lys Lys Gln Tyr Phe Tyr Asn Asp Gly His
1185                1190                1195                1200

Gln Ser Lys Gly Glu Phe Ile Asp Ala Asp Gly Asp Thr Phe Tyr Thr
                1205                1210                1215

Ser Ala Thr Asp Gly Arg Leu Val Thr Gly Val Gln Lys Ile Asn Gly
                1220                1225                1230

Ile Thr Tyr Ala Phe Asp Asn Thr Gly Asn Leu Ile Thr Asn Gln Tyr
            1235                1240                1245

Tyr Gln Leu Ala Asp Gly Lys Tyr Met Leu Leu Asp Asp Ser Gly Arg
            1250                1255                1260

Ala Lys Thr Gly Phe Val Leu Gln Asp Gly Val Leu Arg Tyr Phe Asp
1265                1270                1275                1280

Gln Asn Gly Glu Gln Val Lys Asp Ala Ile Ile Val Asp Pro Asp Thr
                1285                1290                1295

Asn Leu Ser

<210> SEQ ID NO 12
<211> LENGTH: 1877
<212> TYPE: PRT
<213> ORGANISM: Leuconostoc citreum NRRL B-1299

<400> SEQUENCE: 12

Met Arg Gln Lys Glu Thr Ile Thr Arg Lys Lys Leu Tyr Lys Ser Gly
1               5                   10                  15

Lys Ser Trp Val Ala Ala Thr Ala Phe Ala Val Met Gly Val Ser
                20                  25                  30

Ala Val Thr Thr Val Ser Ala Asp Thr Gln Thr Pro Val Gly Thr Thr
            35                  40                  45

Gln Ser Gln Gln Asp Leu Thr Gly Gln Arg Gly Gln Asp Lys Pro Thr
        50                  55                  60

Thr Lys Glu Val Ile Asp Lys Lys Glu Pro Val Pro Gln Val Ser Ala
65                  70                  75                  80

Gln Asn Ala Gly Asp Leu Ser Ala Asp Ala Lys Thr Thr Lys Ala Asp
```

```
                    85                  90                  95
Asp Lys Gln Asp Thr Gln Pro Thr Asn Ala Gln Leu Pro Asp Gln Gly
            100                 105                 110

Asn Lys Gln Thr Asn Ser Asn Ser Asp Lys Gly Val Lys Glu Ser Thr
        115                 120                 125

Thr Ala Pro Val Lys Thr Thr Asp Val Pro Ser Lys Ser Val Thr Pro
    130                 135                 140

Glu Thr Asn Thr Ser Ile Asn Gly Gly Gln Tyr Val Glu Lys Asp Gly
145                 150                 155                 160

Gln Phe Val Tyr Ile Asp Gln Ser Gly Lys Gln Val Ser Gly Leu Gln
                165                 170                 175

Asn Ile Glu Gly His Thr Gln Tyr Phe Asp Pro Lys Thr Gly Tyr Gln
            180                 185                 190

Thr Lys Gly Glu Leu Lys Asn Ile Asp Asp Asn Ala Tyr Tyr Phe Asp
        195                 200                 205

Lys Asn Ser Gly Asn Gly Arg Thr Phe Thr Lys Ile Ser Asn Gly Ser
    210                 215                 220

Tyr Ser Glu Lys Asp Gly Met Trp Gln Tyr Val Asp Ser His Asp Lys
225                 230                 235                 240

Gln Pro Val Lys Gly Leu Tyr Asp Val Glu Gly Asn Leu Gln Tyr Phe
                245                 250                 255

Asp Leu Ser Thr Gly Asn Gln Ala Lys His Gln Ile Arg Ser Val Asp
            260                 265                 270

Gly Val Thr Tyr Tyr Phe Asp Ala Asp Ser Gly Asn Ala Thr Ala Phe
        275                 280                 285

Lys Ala Val Thr Asn Gly Arg Tyr Ala Glu Gln Thr Thr Lys Asp Lys
    290                 295                 300

Asp Gly Asn Glu Thr Ser Tyr Trp Ala Tyr Leu Asp Asn Gln Gly Asn
305                 310                 315                 320

Ala Ile Lys Gly Leu Asn Asp Val Asn Gly Glu Ile Gln Tyr Phe Asp
                325                 330                 335

Glu His Thr Gly Glu Gln Leu Lys Gly His Thr Ala Thr Leu Asp Gly
            340                 345                 350

Thr Thr Tyr Tyr Phe Glu Gly Asn Lys Gly Asn Leu Val Ser Val Val
        355                 360                 365

Asn Thr Ala Pro Thr Gly Gln Tyr Lys Ile Asn Gly Asp Asn Val Tyr
    370                 375                 380

Tyr Leu Asp Asn Asn Asn Glu Ala Ile Lys Gly Leu Tyr Gly Ile Asn
385                 390                 395                 400

Gly Asn Leu Asn Tyr Phe Asp Leu Ala Thr Gly Ile Gln Leu Lys Gly
                405                 410                 415

Gln Ala Lys Asn Ile Asp Gly Ile Gly Tyr Tyr Phe Lys Asp Lys Thr
            420                 425                 430

Gly Asn Gly Ser Tyr Gln Tyr Thr Leu Met Ala Pro Ser Asn Lys Asn
        435                 440                 445

Asp Tyr Thr Gln His Asn Val Val Asn Asn Leu Ser Glu Ser Asn Phe
    450                 455                 460

Lys Asn Leu Val Asp Gly Phe Leu Thr Ala Glu Thr Trp Tyr Arg Pro
465                 470                 475                 480

Ala Gln Ile Leu Ser His Gly Thr Asp Trp Val Ala Ser Thr Asp Lys
                485                 490                 495

Asp Phe Arg Pro Leu Ile Thr Val Trp Trp Pro Asn Lys Asp Ile Gln
            500                 505                 510
```

-continued

Val Asn Tyr Leu Arg Leu Met Gln Asn Glu Gly Val Leu Asn Gln Ser
        515                 520                 525

Ala Val Tyr Asp Leu Asn Thr Asp Gln Leu Leu Asn Glu Ala Ala
530                 535                 540

Gln Gln Ala Gln Ile Gly Ile Glu Lys Lys Ile Ser Gln Thr Gly Asn
545                 550                 555                 560

Thr Asp Trp Leu Asn Asn Val Leu Phe Thr Thr His Asp Gly Gln Pro
                565                 570                 575

Ser Phe Ile Lys Gln Gln Tyr Leu Trp Asn Ser Asp Ser Glu Tyr His
                580                 585                 590

Thr Gly Pro Phe Gln Gly Gly Tyr Leu Lys Tyr Gln Asn Ser Asp Leu
            595                 600                 605

Thr Pro Asn Val Asn Ser Lys Tyr Arg Asn Ala Asp Asn Ser Leu Asp
            610                 615                 620

Phe Leu Leu Ala Asn Asp Val Asp Asn Ser Asn Pro Ile Val Gln Ala
625                 630                 635                 640

Glu Asp Leu Asn Trp Leu Tyr Tyr Leu Leu Asn Phe Gly Ser Ile Thr
                645                 650                 655

Thr Gln Gly Lys Glu Asn Asn Ser Asn Phe Asp Ser Ile Arg Ile Asp
            660                 665                 670

Ala Val Asp Phe Val Ser Asn Asp Leu Ile Gln Arg Thr Tyr Asp Tyr
            675                 680                 685

Leu Arg Ala Ala Tyr Gly Val Asp Lys Asn Asp Lys Glu Ala Asn Ala
        690                 695                 700

His Leu Ser Leu Val Glu Ala Gly Leu Asp Ala Gly Thr Thr Thr Ile
705                 710                 715                 720

His Gln Asp Ala Leu Ile Glu Ser Asp Ile Arg Glu Ala Met Lys Lys
                725                 730                 735

Ser Leu Thr Asn Gly Pro Gly Ser Asn Ile Ser Leu Ser Asn Leu Ile
                740                 745                 750

Gln Asp Lys Glu Gly Asp Lys Leu Ile Ala Asp Arg Ala Asn Asn Ser
        755                 760                 765

Thr Glu Asn Val Ala Ile Pro Asn Tyr Ser Ile Ile His Ala His Asp
    770                 775                 780

Lys Asp Ile Gln Asp Lys Val Gly Ala Ala Ile Thr Asp Ala Thr Gly
785                 790                 795                 800

Ala Asp Trp Thr Asn Phe Thr Pro Glu Gln Leu Gln Lys Gly Leu Ser
                805                 810                 815

Leu Tyr Tyr Glu Asp Gln Arg Lys Ile Glu Lys Lys Tyr Asn Gln Tyr
                820                 825                 830

Asn Ile Pro Ser Ala Tyr Ala Leu Leu Leu Thr Asn Lys Asp Thr Val
            835                 840                 845

Pro Arg Val Tyr Tyr Gly Asp Met Tyr Gln Asp Asp Gly Gln Tyr Met
    850                 855                 860

Gln Lys Gln Ser Leu Tyr Phe Asp Thr Ile Thr Ala Leu Met Glu Ala
865                 870                 875                 880

Arg Lys Gln Phe Val Ala Gly Gly Gln Thr Ile Asn Val Asp Asp Asn
                885                 890                 895

Gly Val Leu Thr Ser Val Arg Phe Gly Lys Gly Ala Met Thr Ala Asn
            900                 905                 910

Asp Ile Gly Thr Asn Glu Thr Arg Thr Gln Gly Ile Gly Val Val Ile
        915                 920                 925

```
Ala Asn Asp Pro Ser Leu Lys Leu Ser Lys Asp Ser Lys Val Thr Leu
    930                 935                 940

His Met Gly Ala Ala His Arg Asn Gln Asn Tyr Arg Ala Leu Leu Leu
945                 950                 955                 960

Thr Thr Asp Asn Gly Ile Asp Ser Tyr Ser Ser Lys Asn Ala Pro
                965                 970                 975

Val Ile Lys Thr Asp Asp Asn Gly Asp Leu Val Phe Ser Asn Gln Asp
            980                 985                 990

Ile Asn Asp Gln Leu Asn Thr Lys Val His Gly Phe Leu Asn Ser Glu
        995                 1000                1005

Val Ser Gly Tyr Leu Ser Ala Trp Val Pro Leu Asp Ala Thr Glu Gln
    1010                1015                1020

Gln Asp Ala Arg Thr Leu Pro Ser Glu Lys Ser Val Asn Asp Gly Lys
1025                1030                1035                1040

Val Leu His Ser Asn Ala Ala Leu Asp Ser Asn Leu Ile Tyr Glu Ala
                1045                1050                1055

Phe Ser Asn Phe Gln Pro Met Pro Thr Asn Arg Asn Glu Tyr Thr Asn
            1060                1065                1070

Val Val Ile Ala Asp Lys Ala Asp Thr Phe Lys Ser Trp Gly Ile Thr
        1075                1080                1085

Ser Phe Glu Met Ala Pro Gln Tyr Arg Ser Ser Gln Asp Lys Thr Phe
    1090                1095                1100

Leu Asp Ser Thr Ile Asp Asn Gly Tyr Ala Phe Thr Asp Arg Tyr Asp
1105                1110                1115                1120

Leu Gly Phe Glu Lys Pro Thr Lys Tyr Gly Asn Asp Glu Asp Leu Arg
                1125                1130                1135

Gln Ala Ile Lys Gln Leu His Ser Ser Gly Met Gln Val Met Ala Asp
            1140                1145                1150

Val Val Ala Asn Gln Ile Tyr Asn Leu Pro Gly Lys Glu Val Ala Ser
        1155                1160                1165

Thr Asn Arg Val Asp Trp Asn Gly Asn Asn Leu Ser Thr Pro Phe Gly
    1170                1175                1180

Thr Gln Met Tyr Val Val Asn Thr Val Gly Gly Gly Lys Tyr Gln Asn
1185                1190                1195                1200

Lys Tyr Gly Gly Glu Phe Leu Asp Lys Leu Lys Ala Ala Tyr Pro Asp
                1205                1210                1215

Ile Phe Arg Ser Lys Asn Tyr Glu Tyr Asp Val Lys Asn Tyr Gly Gly
            1220                1225                1230

Asn Gly Thr Gly Ser Val Tyr Tyr Thr Val Asp Ser Lys Thr Arg Ala
        1235                1240                1245

Glu Leu Asp Thr Asp Thr Lys Ile Lys Glu Trp Ser Ala Lys Tyr Met
    1250                1255                1260

Asn Gly Thr Asn Val Leu Gly Leu Gly Met Gly Tyr Val Leu Lys Asp
1265                1270                1275                1280

Trp Gln Thr Gly Gln Tyr Phe Asn Val Ser Asn Gln Asn Met Lys Phe
                1285                1290                1295

Leu Leu Pro Ser Asp Leu Ile Ser Asn Asp Ile Thr Val Gln Leu Gly
            1300                1305                1310

Val Pro Val Thr Asp Lys Lys Ile Ile Phe Asp Pro Ala Ser Ala Tyr
        1315                1320                1325

Asn Met Tyr Ser Asn Leu Pro Glu Asp Met Gln Val Met Asp Tyr Gln
    1330                1335                1340

Asp Asp Lys Lys Ser Thr Pro Ser Ile Lys Pro Leu Ser Ser Tyr Asn
```

```
                                        1345                1350                1355                1360
Asn Lys Gln Val Gln Val Thr Arg Gln Tyr Thr Asp Ser Lys Gly Val
            1365                1370                1375

Ser Trp Asn Leu Ile Thr Phe Ala Gly Gly Asp Leu Gln Gly Gln Lys
            1380                1385                1390

Leu Trp Val Asp Ser Arg Ala Leu Thr Met Thr Pro Phe Lys Thr Met
            1395                1400                1405

Asn Gln Ile Ser Phe Ile Ser Tyr Ala Asn Arg Asn Asp Gly Leu Phe
            1410                1415                1420

Leu Asn Ala Pro Tyr Gln Val Lys Gly Tyr Gln Leu Ala Gly Met Ser
1425                1430                1435                1440

Asn Gln Tyr Lys Gly Gln Gln Val Thr Ile Ala Gly Val Ala Asn Val
            1445                1450                1455

Ser Gly Lys Asp Trp Ser Leu Ile Ser Phe Asn Gly Thr Gln Tyr Trp
            1460                1465                1470

Ile Asp Ser Gln Ala Leu Asn Thr Asn Phe Thr His Asp Met Asn Gln
            1475                1480                1485

Lys Val Phe Val Asn Thr Thr Ser Asn Leu Asp Gly Leu Phe Leu Asn
            1490                1495                1500

Ala Pro Tyr Arg Gln Pro Gly Tyr Lys Leu Ala Gly Leu Ala Lys Asn
1505                1510                1515                1520

Tyr Asn Asn Gln Thr Val Thr Val Ser Gln Gln Tyr Phe Asp Asp Gln
            1525                1530                1535

Gly Thr Val Trp Ser Gln Val Val Leu Gly Gly Gln Thr Val Trp Val
            1540                1545                1550

Asp Asn His Ala Leu Ala Gln Met Gln Val Arg Asp Thr Asn Gln Gln
            1555                1560                1565

Leu Tyr Val Asn Ser Asn Gly Arg Asn Asp Gly Leu Phe Leu Asn Ala
            1570                1575                1580

Pro Tyr Arg Gly Gln Gly Ser Gln Leu Ile Gly Met Thr Ala Asp Tyr
1585                1590                1595                1600

Asn Gly Gln His Val Gln Val Thr Lys Gln Gly Gln Asp Ala Tyr Gly
            1605                1610                1615

Ala Gln Trp Arg Leu Ile Thr Leu Asn Asn Gln Gln Val Trp Val Asp
            1620                1625                1630

Ser Arg Ala Leu Ser Thr Thr Ile Met Gln Ala Met Asn Asp Asp Met
            1635                1640                1645

Tyr Val Asn Ser Ser Gln Arg Thr Asp Gly Leu Trp Leu Asn Ala Pro
            1650                1655                1660

Tyr Thr Met Ser Gly Ala Lys Trp Ala Gly Asp Thr Arg Ser Ala Asn
1665                1670                1675                1680

Gly Arg Tyr Val His Ile Ser Lys Ala Tyr Ser Asn Glu Val Gly Asn
            1685                1690                1695

Thr Tyr Tyr Leu Thr Asn Leu Asn Gly Gln Ser Thr Trp Ile Asp Lys
            1700                1705                1710

Arg Ala Phe Thr Ala Thr Phe Asp Gln Val Val Ala Leu Asn Ala Thr
            1715                1720                1725

Ile Val Ala Arg Gln Arg Pro Asp Gly Met Phe Lys Thr Ala Pro Tyr
            1730                1735                1740

Gly Glu Ala Gly Ala Gln Phe Val Asp Tyr Val Thr Asn Tyr Asn Gln
1745                1750                1755                1760

Gln Thr Val Pro Val Thr Lys Gln His Ser Asp Ala Gln Gly Asn Gln
            1765                1770                1775
```

-continued

```
Trp Tyr Leu Ala Thr Val Asn Gly Thr Gln Tyr Trp Ile Asp Gln Arg
            1780                1785                1790

Ser Phe Ser Pro Val Val Thr Lys Val Val Asp Tyr Gln Ala Lys Ile
        1795                1800                1805

Val Pro Arg Thr Thr Arg Asp Gly Val Phe Ser Gly Ala Pro Tyr Gly
    1810                1815                1820

Glu Val Asn Ala Lys Leu Val Asn Met Ala Thr Ala Tyr Gln Asn Gln
1825                1830                1835                1840

Val Val His Ala Thr Gly Glu Tyr Thr Asn Ala Ser Gly Ile Thr Trp
                1845                1850                1855

Ser Gln Phe Ala Leu Ser Gly Gln Glu Asp Lys Leu Trp Ile Asp Lys
            1860                1865                1870

Arg Ala Leu Gln Ala
        1875

<210> SEQ ID NO 13
<211> LENGTH: 1125
<212> TYPE: PRT
<213> ORGANISM: Leuconostoc mesenteroides NRRL B-1299

<400> SEQUENCE: 13

Met Ala His His His His His His Val Thr Ser Leu Tyr Lys Lys Ala
1               5                   10                  15

Gly Ser Ala Ala Ala Pro Phe Thr Met Ala Gln Ala Gly His Tyr Ile
            20                  25                  30

Thr Lys Asn Gly Asn Asp Trp Gln Tyr Asp Thr Asn Gly Glu Leu Ala
        35                  40                  45

Lys Gly Leu Arg Gln Asp Ser Asn Gly Lys Leu Arg Tyr Phe Asp Leu
    50                  55                  60

Thr Thr Gly Ile Gln Ala Lys Gly Gln Phe Val Thr Ile Gly Gln Glu
65                  70                  75                  80

Thr Tyr Tyr Phe Ser Lys Asp His Gly Asp Ala Gln Leu Leu Pro Met
                85                  90                  95

Val Thr Glu Gly His Tyr Gly Thr Ile Thr Leu Lys Gln Gly Gln Asp
            100                 105                 110

Thr Lys Thr Ala Trp Val Tyr Arg Asp Gln Asn Asn Thr Ile Leu Lys
        115                 120                 125

Gly Leu Gln Asn Ile Asn Gly Thr Leu Gln Phe Phe Asp Pro Tyr Thr
    130                 135                 140

Gly Glu Gln Leu Lys Gly Gly Val Ala Lys Tyr Asp Asp Lys Leu Phe
145                 150                 155                 160

Tyr Phe Glu Ser Gly Lys Gly Asn Leu Val Ser Thr Val Ala Gly Asp
                165                 170                 175

Tyr Gln Asp Gly His Tyr Ile Ser Gln Asp Gly Gln Thr Arg Tyr Ala
            180                 185                 190

Asp Lys Gln Asn Gln Leu Val Lys Gly Leu Val Thr Val Asn Gly Ala
        195                 200                 205

Leu Gln Tyr Phe Asp Asn Ala Thr Gly Asn Gln Ile Lys Asn Gln Gln
    210                 215                 220

Val Ile Val Asp Gly Lys Thr Tyr Tyr Phe Asp Asp Lys Gly Asn Gly
225                 230                 235                 240

Glu Tyr Leu Phe Thr Asn Thr Leu Asp Met Ser Thr Asn Ala Phe Ser
                245                 250                 255

Thr Lys Asn Val Ala Phe Asn His Asp Ser Ser Ser Phe Asp His Thr
```

-continued

```
            260                 265                 270
Val Asp Gly Phe Leu Thr Ala Asp Thr Trp Tyr Arg Pro Lys Ser Ile
            275                 280                 285
Leu Ala Asn Gly Thr Thr Trp Arg Asp Ser Thr Asp Lys Asp Met Arg
            290                 295                 300
Pro Leu Ile Thr Val Trp Trp Pro Asn Lys Asn Val Gln Val Asn Tyr
305                 310                 315                 320
Leu Asn Phe Met Lys Ala Asn Gly Leu Leu Thr Thr Ala Ala Gln Tyr
                325                 330                 335
Thr Leu His Ser Asp Gln Tyr Asp Leu Asn Gln Ala Ala Gln Asp Val
                340                 345                 350
Gln Val Ala Ile Glu Arg Arg Ile Ala Ser Glu His Gly Thr Asp Trp
                355                 360                 365
Leu Gln Lys Leu Leu Phe Glu Ser Gln Asn Asn Pro Ser Phe Val
            370                 375                 380
Lys Gln Gln Phe Ile Trp Asn Lys Asp Ser Glu Tyr His Gly Gly
385                 390                 395                 400
Asp Ala Trp Phe Gln Gly Gly Tyr Leu Lys Tyr Gly Asn Asn Pro Leu
                405                 410                 415
Thr Pro Thr Thr Asn Ser Asp Tyr Arg Gln Pro Gly Asn Ala Phe Asp
                420                 425                 430
Phe Leu Leu Ala Asn Asp Val Asp Asn Ser Asn Pro Val Val Gln Ala
                435                 440                 445
Glu Asn Leu Asn Trp Leu His Tyr Leu Met Asn Phe Gly Thr Ile Thr
450                 455                 460
Ala Gly Gln Asp Asp Ala Asn Phe Asp Ser Ile Arg Ile Asp Ala Val
465                 470                 475                 480
Asp Phe Ile His Asn Asp Thr Ile Gln Arg Thr Tyr Asp Tyr Leu Arg
                485                 490                 495
Asp Ala Tyr Gln Val Gln Gln Ser Glu Ala Lys Ala Asn Gln His Ile
                500                 505                 510
Ser Leu Val Glu Ala Gly Leu Asp Ala Gly Thr Ser Thr Ile His Asn
            515                 520                 525
Asp Ala Leu Ile Glu Ser Asn Leu Arg Glu Ala Ala Thr Leu Ser Leu
            530                 535                 540
Thr Asn Glu Pro Gly Lys Asn Lys Pro Leu Thr Asn Met Leu Gln Asp
545                 550                 555                 560
Val Asp Gly Gly Thr Leu Ile Thr Asp His Thr Gln Asn Ser Thr Glu
                565                 570                 575
Asn Gln Ala Thr Pro Asn Tyr Ser Ile Ile His Ala His Asp Lys Gly
                580                 585                 590
Val Gln Glu Lys Val Gly Ala Ala Ile Thr Asp Ala Thr Gly Ala Asp
            595                 600                 605
Trp Thr Asn Phe Thr Asp Glu Gln Leu Lys Ala Gly Leu Glu Leu Phe
            610                 615                 620
Tyr Lys Asp Gln Arg Ala Thr Asn Lys Lys Tyr Asn Ser Tyr Asn Ile
625                 630                 635                 640
Pro Ser Ile Tyr Ala Leu Met Leu Thr Asn Lys Asp Thr Val Pro Arg
                645                 650                 655
Met Tyr Tyr Gly Asp Met Tyr Gln Asp Asp Gly Gln Tyr Met Ala Asn
                660                 665                 670
Lys Ser Ile Tyr Tyr Asp Ala Leu Val Ser Leu Met Thr Ala Arg Lys
            675                 680                 685
```

-continued

Ser Tyr Val Ser Gly Gly Gln Thr Met Ser Val Asp Asn His Gly Leu
690                     695                 700

Leu Lys Ser Val Arg Phe Gly Lys Asp Ala Met Thr Ala Asn Asp Leu
705                     710                 715                 720

Gly Thr Ser Ala Thr Arg Thr Glu Gly Leu Gly Val Ile Ile Gly Asn
            725                 730                 735

Asp Pro Lys Leu Gln Leu Asn Asp Ser Asp Lys Val Thr Leu Asp Met
            740                 745                 750

Gly Ala Ala His Lys Asn Gln Lys Tyr Arg Ala Val Ile Leu Thr Thr
            755                 760                 765

Arg Asp Gly Leu Ala Thr Phe Asn Ser Asp Gln Ala Pro Thr Ala Trp
770                     775                 780

Thr Asn Asp Gln Gly Thr Leu Thr Phe Ser Asn Gln Glu Ile Asn Gly
785                     790                 795                 800

Gln Asp Asn Thr Gln Ile Arg Gly Val Ala Asn Pro Gln Val Ser Gly
            805                 810                 815

Tyr Leu Ala Val Trp Val Pro Val Gly Ala Ser Asp Asn Gln Asp Ala
            820                 825                 830

Arg Thr Ala Ala Thr Thr Thr Glu Asn His Asp Gly Lys Val Leu His
            835                 840                 845

Ser Asn Ala Ala Leu Asp Ser Asn Leu Ile Tyr Glu Gly Phe Ser Asn
850                     855                 860

Phe Gln Pro Lys Ala Thr Thr His Asp Glu Leu Thr Asn Val Val Ile
865                     870                 875                 880

Ala Lys Asn Ala Asp Val Phe Asn Asn Trp Gly Ile Thr Ser Phe Glu
            885                 890                 895

Met Ala Pro Gln Tyr Arg Ser Ser Gly Asp His Thr Phe Leu Asp Ser
            900                 905                 910

Thr Ile Asp Asn Gly Tyr Ala Phe Thr Asp Arg Tyr Asp Leu Gly Phe
            915                 920                 925

Asn Thr Pro Thr Lys Tyr Gly Thr Asp Gly Asp Leu Arg Ala Thr Ile
            930                 935                 940

Gln Ala Leu His His Ala Asn Met Gln Val Met Ala Asp Val Val Asp
945                     950                 955                 960

Asn Gln Val Tyr Asn Leu Pro Gly Lys Glu Val Val Ser Ala Thr Arg
            965                 970                 975

Ala Gly Val Tyr Gly Asn Asp Asp Ala Thr Gly Phe Gly Thr Gln Leu
            980                 985                 990

Tyr Val Thr Asn Ser Val Gly Gly Gln Tyr Gln Glu Lys Tyr Ala
            995                 1000                1005

Gly Gln Tyr Leu Glu Ala Leu Lys Ala Lys Tyr Pro Asp Leu Phe Glu
    1010                1015                1020

Gly Lys Ala Tyr Asp Tyr Trp Tyr Lys Asn Tyr Ala Asn Asp Gly Ser
1025                    1030                1035                1040

Asn Pro Tyr Tyr Thr Leu Ser His Gly Asp Arg Glu Ser Ile Pro Ala
            1045                1050                1055

Asp Val Ala Ile Lys Gln Trp Ser Ala Lys Tyr Met Asn Gly Thr Asn
            1060                1065                1070

Val Leu Gly Asn Gly Met Gly Tyr Val Leu Lys Asp Trp His Asn Gly
            1075                1080                1085

Gln Tyr Phe Lys Leu Asp Gly Asp Lys Ser Thr Leu Pro Lys Gly Gly
    1090                1095                1100

Arg Ala Asp Pro Ala Phe Leu Tyr Lys Val Val Ser Ala Trp Ser His
1105                1110                1115                1120

Pro Gln Phe Glu Lys
                1125

<210> SEQ ID NO 14
<211> LENGTH: 650
<212> TYPE: PRT
<213> ORGANISM: Deinococcus geothermalis

<400> SEQUENCE: 14

Met Leu Lys Asp Val Leu Thr Ser Glu Leu Ala Ala Gln Val Arg Asp
1               5                   10                  15

Ala Phe Asp Asp Arg Asp Ala Glu Thr Phe Leu Leu Arg Leu Glu
            20                  25                  30

Arg Tyr Gly Glu Asp Leu Trp Glu Ser Leu Arg Ala Val Tyr Gly Asp
        35                  40                  45

Gln Val Arg Ala Leu Pro Gly Arg Leu Leu Glu Val Met Leu His Ala
    50                  55                  60

Tyr His Ala Arg Pro Ala Glu Leu Arg Arg Leu Asp Glu Ala Arg Leu
65                  70                  75                  80

Leu Arg Pro Asp Trp Leu Gln Arg Pro Glu Met Val Gly Tyr Val Ala
                85                  90                  95

Tyr Thr Asp Arg Phe Ala Gly Thr Leu Lys Gly Val Glu Glu Arg Leu
            100                 105                 110

Asp Tyr Leu Glu Gly Leu Gly Val Lys Tyr Leu His Leu Met Pro Leu
        115                 120                 125

Leu Arg Pro Arg Glu Gly Glu Asn Asp Gly Gly Tyr Ala Val Gln Asp
    130                 135                 140

Tyr Arg Ala Val Arg Pro Asp Leu Gly Thr Met Asp Asp Leu Ser Ala
145                 150                 155                 160

Leu Ala Arg Ala Leu Arg Gly Arg Gly Ile Ser Leu Val Leu Asp Leu
                165                 170                 175

Val Leu Asn His Val Ala Arg Glu His Ala Trp Ala Gln Lys Ala Arg
            180                 185                 190

Ala Gly Asp Pro Lys Tyr Arg Ala Tyr Phe His Leu Phe Pro Asp Arg
        195                 200                 205

Arg Gly Pro Asp Ala Phe Glu Ala Thr Leu Pro Glu Ile Phe Pro Asp
    210                 215                 220

Phe Ala Pro Gly Asn Phe Ser Trp Asp Glu Glu Ile Gly Glu Gly Glu
225                 230                 235                 240

Gly Gly Trp Val Trp Thr Thr Phe Asn Ser Tyr Gln Trp Asp Leu Asn
                245                 250                 255

Trp Ala Asn Pro Asp Val Phe Leu Glu Phe Val Asp Ile Ile Leu Tyr
            260                 265                 270

Leu Ala Asn Arg Gly Val Glu Val Phe Arg Leu Asp Ala Ile Ala Phe
        275                 280                 285

Ile Trp Lys Arg Leu Gly Thr Asp Cys Gln Asn Gln Pro Glu Val His
    290                 295                 300

His Leu Thr Arg Ala Leu Arg Ala Ala Arg Ile Val Ala Pro Ala
305                 310                 315                 320

Val Ala Phe Lys Ala Glu Ala Ile Val Ala Pro Ala Asp Leu Ile His
                325                 330                 335

Tyr Leu Gly Thr Arg Ala His His Gly Lys Val Ser Asp Met Ala Tyr
            340                 345                 350

His Asn Ser Leu Met Val Gln Leu Trp Ser Ser Leu Ala Ser Arg Asn
            355                 360                 365

Thr Arg Leu Phe Glu Glu Ala Leu Arg Ala Phe Pro Pro Lys Pro Thr
370                 375                 380

Ser Thr Thr Trp Gly Leu Tyr Val Arg Cys His Asp Ile Gly Trp
385                 390                 395                 400

Ala Ile Ser Asp Glu Asp Ala Ala Arg Ala Gly Leu Asn Gly Ala Ala
                405                 410                 415

His Arg His Phe Leu Ser Asp Phe Tyr Ser Gly Gln Phe Pro Gly Ser
            420                 425                 430

Phe Ala Arg Gly Leu Val Phe Gln Tyr Asn Pro Val Asn Gly Asp Arg
        435                 440                 445

Arg Ile Ser Gly Ser Ala Ala Ser Leu Ala Gly Leu Glu Ala Ala Leu
    450                 455                 460

Glu Thr Gly Asp Pro Gly Arg Ile Glu Asp Ala Val Arg Arg Leu Leu
465                 470                 475                 480

Leu Leu His Thr Val Ile Leu Gly Phe Gly Val Pro Leu Leu Tyr
                485                 490                 495

Met Gly Asp Glu Leu Ala Leu Leu Asn Asp Tyr Ala Phe Glu Asp Val
            500                 505                 510

Pro Glu His Ala Pro Asp Asn Arg Trp Val His Arg Pro Gln Met Asp
        515                 520                 525

Trp Ala Leu Ala Glu Arg Val Arg Gln Glu Pro Ser Ser Pro Ala Gly
530                 535                 540

Arg Val Asn Thr Gly Leu Arg His Leu Leu Val Arg Arg Asp Thr
545                 550                 555                 560

Pro Gln Leu His Ala Ser Ile Glu Ser Gln Val Leu Pro Ser Pro Asp
                565                 570                 575

Ser Arg Ala Leu Leu Leu Arg Arg Asp His Pro Leu Gly Gly Met Val
            580                 585                 590

Gln Val Tyr Asn Phe Ser Glu Glu Thr Val Met Leu Pro Ser His Val
        595                 600                 605

Leu Arg Asp Val Leu Gly Asp His Val Gln Asp Arg Leu Ser Gly Ser
    610                 615                 620

Ala Phe Arg Leu Asp Arg Pro Thr Val Arg Leu Glu Gly Tyr Arg Ala
625                 630                 635                 640

Leu Trp Leu Thr Ala Gly Glu Ala Pro Ala
                645                 650

<210> SEQ ID NO 15
<211> LENGTH: 1484
<212> TYPE: PRT
<213> ORGANISM: Oenococcus kitaharae DSM17330

<400> SEQUENCE: 15

Met Met Ala Thr Gly Ser Asn Leu Ile Thr Ala Gln Ala Asp Asp Leu
1               5                   10                  15

Asn Gln Glu Gly Thr Ala Ala Gln Ser Val Ser Pro Ser Thr Ala Ala
            20                  25                  30

Ala Asn Gln Ser Glu Ser Ser Ala Gln Ser Thr Glu Gln Ser Ala Thr
        35                  40                  45

Gln Ala Ala Thr Asp Gly Glu Ala Ser Thr Val Ser Thr Ala Val Thr
    50                  55                  60

Thr Ile Thr Pro His Tyr Val Gln Gln Ala Gly Lys Trp Leu Tyr Met

-continued

```
                65                  70                  75                  80
Gly Ser Asp Gly Glu Phe Val Lys Gly Pro Gln Thr Ile Asp Gly Asn
                    85                  90                  95
Leu Gln Phe Phe Asp Glu Gln Gly Ile Gln Ile Lys Gly Ser Phe Glu
                    100                 105                 110
Thr Val Asp Gly Ser Ser Tyr Tyr Phe Asp Ser Gln Ser Gly Asn Ala
                    115                 120                 125
Val Thr Gly Phe Lys Ile Ile Asn Asn Asp Leu His Tyr Phe Glu Glu
                    130                 135                 140
Asp Gly Lys Glu Thr Val Asn Asn Tyr Ala Thr Asp Lys Gln Gly Asn
145                 150                 155                 160
Ile Phe Tyr Phe Asp Glu Asn Gly Gln Met Ala Thr Gly Val Lys Thr
                    165                 170                 175
Ile Gln Gly Gln Ser Tyr Tyr Phe Asp Gln Asp Gly His Met Arg Lys
                    180                 185                 190
Gly Tyr Ser Gly Val Phe Asp Asn Gln Val Leu Tyr Phe Asp Lys Thr
                    195                 200                 205
Thr Gly Ala Leu Ala Asn Thr Asn Val Ser Ser Ile Lys Glu Gly Leu
                    210                 215                 220
Thr Ala Gln Asn Asp Asp Phe Thr Ala His Asn Ala Val Tyr Ser Thr
225                 230                 235                 240
Lys Ser Glu Ser Phe Thr Asn Ile Asp Gly Tyr Leu Thr Ala Glu Ala
                    245                 250                 255
Trp Tyr Arg Pro Ala Asp Ile Leu Glu Asn Gly Thr Asp Trp Arg Ala
                    260                 265                 270
Ser Arg Ala Asp Glu Phe Arg Pro Ile Leu Thr Thr Trp Trp Pro Asp
                    275                 280                 285
Lys Gln Thr Glu Val Asn Tyr Leu Asn Tyr Met Lys Thr Gln Gly Phe
                    290                 295                 300
Ile Thr Asn Asp Gln Asp Phe Lys Leu Ser Asp Asp Gln Leu Leu Leu
305                 310                 315                 320
Asn His Ala Ala Gln Ser Val Gln Gly Glu Ile Glu Lys Lys Ile Ser
                    325                 330                 335
Gln Gln Gly Ser Thr Asp Trp Leu Lys Thr Leu Leu Gln Thr Phe Ile
                    340                 345                 350
Asn Gln Gln Pro Ser Trp Asn Gly Glu Ser Glu Asp Pro Gly Ser Asp
                    355                 360                 365
His Leu Gln Gly Gly Ala Leu Thr Phe Val Asn Ser Pro Leu Thr Pro
                    370                 375                 380
Asp Ser Asn Ser Asn Phe Arg Leu Leu Asn Arg Thr Pro Thr Asn Gln
385                 390                 395                 400
Thr Gly Thr Pro Gln Tyr Asp Thr Asp Ala Ser Leu Gly Gly Phe Glu
                    405                 410                 415
Leu Leu Leu Ala Asn Asp Val Asp Asn Ser Asn Pro Val Val Gln Ala
                    420                 425                 430
Glu Gln Leu Asn Trp Leu Tyr Tyr Leu Leu Asn Phe Gly Ser Ile Thr
                    435                 440                 445
Ala Asp Asp Pro Asn Ala Asn Phe Asp Gly Ile Arg Ile Asp Ala Val
                    450                 455                 460
Asp Asn Val Asp Ala Asp Leu Leu Gln Ile Ala Ala Ala Tyr Phe Lys
465                 470                 475                 480
Asp Ala Phe Lys Ser Gly Ser Asn Asp Gln Thr Thr Asn Gln His Leu
                    485                 490                 495
```

-continued

Ser Ile Leu Glu Asp Trp Ser His Asn Asp Pro Glu Tyr Met Lys Ala
        500                 505                 510

Gln Gly Tyr Pro Gln Leu Thr Met Asp Asp Tyr Met His Thr Gln Leu
        515                 520                 525

Ile Trp Ser Leu Thr Lys Pro Asp Asn Ile Arg Gly Thr Met Gln Arg
530                 535                 540

Phe Met Asp Tyr Tyr Leu Val Asn Arg Ala Asn Asp Ser Thr Asn Asn
545                 550                 555                 560

Glu Ala Val Ala Asn Tyr Ser Phe Val Arg Ala His Asp Ser Glu Val
                565                 570                 575

Gln Thr Val Ile Ala Gln Ile Ile Ser Asp Leu Tyr Pro Asn Ser Gly
        580                 585                 590

Ser Gly Leu Ile Pro Thr Thr Asp Gln Leu Gln Ala Ala Phe Glu Val
        595                 600                 605

Tyr Asn Ala Asp Met Lys Ser Asp Val Lys Lys Tyr Thr Gln Tyr Asn
        610                 615                 620

Ile Pro Ser Ala Tyr Ala Met Leu Leu Thr Asn Lys Asp Thr Val Pro
625                 630                 635                 640

Arg Val Tyr Tyr Gly Asp Met Tyr Thr Asp Asp Gly Asp Tyr Met Ala
                645                 650                 655

Asn Lys Ser Pro Tyr Phe Asp Ala Ile Ser Thr Leu Leu Lys Ala Arg
                660                 665                 670

Val Lys Tyr Ala Ala Gly Gly Gln Ser Met Ala Val Asp Lys Asn Asp
        675                 680                 685

Ile Leu Thr Ser Val Arg Phe Gly Gln Asn Ala Met Leu Ala Ser Asp
        690                 695                 700

Ser Gly Asp Asn Gln Thr Arg Gln Glu Gly Ile Gly Val Ile Val Ser
705                 710                 715                 720

Asn Asn Ser His Leu Lys Leu Ala Glu Asn Asp Gln Val Val Leu His
                725                 730                 735

Met Gly Ala Ala His Lys Asn Gln Ala Phe Arg Ala Leu Leu Leu Thr
                740                 745                 750

Ile Glu Ser Gly Leu Glu Asn Phe Asp Thr Asp Leu Gln Ala Pro Val
        755                 760                 765

Lys Tyr Thr Asp Ala Asn Gly Asp Leu Ile Phe Thr Ala Ala Glu Leu
        770                 775                 780

Ala Gly Tyr Leu Asn Pro Glu Val Ser Gly Tyr Leu Ser Ala Trp Val
785                 790                 795                 800

Pro Val Gly Ala Ala Asp Asn Gln Asp Ala Arg Thr Ala Ala Asp Ser
                805                 810                 815

Ala Thr Ser Thr Asp Gly Asn Val Phe His Ser Asn Ala Ala Leu Asp
                820                 825                 830

Ser Asn Val Ile Phe Glu Gly Phe Ser Asn Phe Gln Ser Ile Pro Thr
        835                 840                 845

Ala Glu Gln His Asp Asp Phe Thr Asn Val Lys Ile Ala Glu Asn Ala
        850                 855                 860

Gly Leu Phe Lys Asp Trp Gly Ile Thr Ser Phe Gln Leu Ala Pro Gln
865                 870                 875                 880

Tyr Arg Ser Ser Thr Asp Ser Thr Phe Leu Asp Ser Ile Ile Gln Asn
                885                 890                 895

Gly Tyr Ala Phe Thr Asp Arg Tyr Asp Leu Gly Phe Asp Thr Pro Thr
                900                 905                 910

-continued

```
Lys Tyr Gly Asp Val Asp Asp Leu Arg Ala Ala Ile Lys Ala Leu His
            915                 920                 925
Ala Asn Asn Ile Gln Val Met Ala Asp Trp Val Pro Asp Gln Ile Tyr
        930                 935                 940
Asn Leu Gln Asn Pro Glu Ile Ile Thr Val Asn Arg Thr Asp Ser Tyr
945                 950                 955                 960
Gly Gln Pro Ile Ala Gly Ser Asp Leu Gln Asn Asp Leu Tyr Leu Ala
                965                 970                 975
Tyr Thr Asn Gly Gly Gln Tyr Gln Thr Lys Phe Gly Gly Ala Phe
            980                 985                 990
Leu Glu Lys Leu Gln Gln Leu Tyr Pro Asp Leu Phe Thr Lys Thr Gln
        995                 1000                1005
Ile Ser Thr Gly Gln Thr Ile Asp Pro Ser Gln Lys Ile Thr Glu Trp
    1010                1015                1020
Ser Ala Lys Tyr Phe Asn Gly Ser Asn Ile Gln Gly Arg Gly Ala Tyr
1025                1030                1035                1040
Tyr Val Leu Arg Asp Ser Gly Thr Asp Gln Tyr Phe Lys Val Ile Ser
                1045                1050                1055
Asn Asp Glu Asn Glu Ala Phe Leu Pro Lys Gln Leu Thr Asn Gln Pro
            1060                1065                1070
Gly Glu Thr Gly Phe Ser Gln Asp Gln Gly Ile Ile Phe Phe Ser
        1075                1080                1085
Thr Ser Gly Tyr Gln Ala Lys Asn Ala Phe Val Gln Gly Asp Asp Gly
    1090                1095                1100
Asn Tyr Tyr Tyr Phe Asp Asn Thr Gly His Met Val Thr Gly Pro Gln
1105                1110                1115                1120
Thr Ile Asn Gly Arg His Tyr Leu Phe Phe Pro Asn Gly Val Glu Ala
                1125                1130                1135
Gln Asn Val Phe Val Gln Asn Asp Arg Gly Glu Thr Tyr Tyr Tyr Asp
            1140                1145                1150
Gln Arg Gly Arg Gln Val Ala Asn Gln Tyr Val Thr Asp Thr Asn Gly
        1155                1160                1165
Asn Ser Phe Arg Phe Asp Glu Asn Gly Ile Met Leu Ala Asn Gln Leu
    1170                1175                1180
Ala Gln Val Asp Gly His Trp Gln Phe Phe Lys Ser Ser Gly Val Gln
1185                1190                1195                1200
Ala Lys Asp Ala Phe Ile Leu Gly Ser Asp Gly Lys Leu Arg Tyr Phe
                1205                1210                1215
Glu Ser Gly Asn Gly Asn Met Ala Val Asn Glu Phe Lys Gly Ser Glu
            1220                1225                1230
Asn Gly Arg Tyr Tyr Tyr Phe Gly Ala Asp Gly Gln Ala Val Ser Gly
        1235                1240                1245
Leu Gln Thr Ile Asn Gly Arg Gln Leu Tyr Phe Asp Asp His Gly Gln
    1250                1255                1260
Gln Met Lys Asp Ala Phe Tyr Thr Asn Gln Ser Gly Gln Arg Phe Tyr
1265                1270                1275                1280
Phe Asn Ala Leu Thr Gly Asp Leu Val Lys Gly Asn Phe Ile Tyr Thr
                1285                1290                1295
Ser Ala Ser Ser Ser Phe Thr Pro Asp Asn Asp Ser Asp Ser Tyr
            1300                1305                1310
Gln Gly Asp Ser His Leu Trp Tyr Tyr Ala Asp Ser Gln Gly Gln Ile
        1315                1320                1325
Val Thr Gly Phe Gln Thr Ile Asn Gly His Leu Gln Tyr Phe Asp Asp
```

-continued

```
                1330                1335                1340
Ile Ser Gly Gln Met Ile Thr Asn Arg Phe Met Arg Ala Asp Gly
1345                1350                1355                1360

Asn Trp Ile Tyr Leu Asp Glu Asn Gly Glu Ala Val Arg Gly Met Arg
                1365                1370                1375

Val Ile Asn Gly Leu Thr Asn Tyr Phe Arg Asp Asp Phe Thr Gln Val
                1380                1385                1390

Lys Asp Gly Phe Ala Gln Asp Pro Asn Ser Gly Glu Arg His Tyr Phe
                1395                1400                1405

Asn Gly Thr Asn Gly Ala Met Val Thr Asn Asp Tyr Phe Ser Pro Asp
                1410                1415                1420

Gln Ile His Trp Tyr Tyr Ala Asp Asp Ser Gly Gln Pro Val Thr Gly
1425                1430                1435                1440

Phe Gln Thr Ile Lys Gly Gln Val Gln Tyr Phe Asp Gln Asp Gly Ile
                1445                1450                1455

Gln Leu Lys Gly Gly Ser Gln Thr Asp Pro Val Thr Lys Gln Thr Tyr
                1460                1465                1470

Tyr Phe Asp Asp Lys Phe Gly Asn Gly Gln Ile Leu
                1475                1480
```

<210> SEQ ID NO 16
<211> LENGTH: 1888
<212> TYPE: PRT
<213> ORGANISM: Leuconostoc citreum NRRL B-742

<400> SEQUENCE: 16

```
Met Glu Met Lys Glu Thr Ile Thr Arg Lys Lys Leu Tyr Lys Ser Gly
1               5                   10                  15

Lys Ser Trp Val Ala Ala Ala Thr Ala Phe Ala Val Met Gly Val Ser
                20                  25                  30

Ala Val Thr Thr Val Ser Ala Asp Thr Gln Thr Pro Val Gly Thr Thr
                35                  40                  45

Gln Ser Gln Gln Asp Leu Thr Gly Gln Thr Gly Gln Asp Lys Pro Thr
        50                  55                  60

Thr Lys Glu Val Ile Asp Lys Lys Glu Pro Val Pro Gln Val Ser Ala
65                  70                  75                  80

Gln Asn Val Gly Asp Leu Ser Ala Asp Ala Lys Thr Pro Lys Ala Asp
                85                  90                  95

Asp Lys Gln Asp Thr Gln Pro Thr Asn Ala Gln Leu Pro Asp Gln Gly
                100                 105                 110

Asn Lys Gln Thr Asn Ser Asn Ser Asp Lys Gly Val Lys Glu Ser Thr
        115                 120                 125

Thr Ala Pro Val Lys Thr Thr Asp Val Pro Ser Lys Ser Val Ala Pro
        130                 135                 140

Glu Thr Asn Thr Ser Ile Asn Gly Gly Gln Tyr Val Glu Lys Asp Gly
145                 150                 155                 160

Gln Phe Val Tyr Ile Asp Gln Ser Gly Lys Gln Val Ser Gly Leu Gln
                165                 170                 175

Asn Ile Glu Gly His Thr Gln Tyr Phe Asp Pro Lys Thr Gly Tyr Gln
                180                 185                 190

Thr Lys Gly Glu Leu Lys Asn Ile Asp Asp Asn Ala Tyr Tyr Phe Asp
        195                 200                 205

Lys Asn Ser Gly Asn Gly Arg Thr Phe Thr Lys Ile Ser Asn Gly Ser
210                 215                 220
```

-continued

Tyr Ser Glu Lys Asp Gly Met Trp Gln Tyr Val Asp Ser His Asp Lys
225                 230                 235                 240

Gln Pro Val Lys Gly Leu Tyr Asp Val Glu Gly Asn Leu Gln Tyr Phe
            245                 250                 255

Asp Leu Ser Thr Gly Asn Gln Ala Lys His Gln Ile Arg Ser Val Asp
        260                 265                 270

Gly Val Thr Tyr Tyr Phe Asp Ala Asp Ser Gly Asn Ala Thr Ala Phe
    275                 280                 285

Lys Ala Val Thr Asn Gly Arg Tyr Ala Glu Gln Thr Thr Lys Asp Lys
290                 295                 300

Asp Gly Asn Glu Thr Ser Tyr Trp Ala Tyr Leu Asp Asn Gln Gly Asn
305                 310                 315                 320

Ala Ile Lys Gly Leu Asn Asp Val Asn Gly Glu Ile Gln Tyr Phe Asp
            325                 330                 335

Glu His Thr Gly Glu Gln Leu Lys Gly His Thr Ala Thr Val Asp Gly
        340                 345                 350

Thr Thr Tyr Tyr Phe Glu Gly Asn Lys Gly Asn Leu Val Ser Val Val
    355                 360                 365

Asn Thr Ala Pro Thr Gly Gln Tyr Lys Ile Asn Gly Asp Asn Val Tyr
370                 375                 380

Tyr Leu Asp Asn Asn Glu Ala Ile Lys Gly Leu Tyr Gly Ile Asn
385                 390                 395                 400

Gly Asn Leu Asn Tyr Phe Asp Leu Ala Thr Gly Ile Gln Leu Lys Gly
            405                 410                 415

Gln Ala Lys Asn Ile Asp Gly Ile Gly Tyr Tyr Phe Asp Gln Asn Asn
        420                 425                 430

Gly Asn Gly Glu Tyr Arg Tyr Ser Leu Thr Gly Pro Val Val Lys Asp
    435                 440                 445

Val Tyr Ser Gln His Asn Ala Val Asn Asn Leu Ser Ala Asn Asn Phe
450                 455                 460

Lys Asn Leu Val Asp Gly Phe Leu Thr Ala Glu Thr Trp Tyr Arg Pro
465                 470                 475                 480

Ala Gln Ile Leu Ser His Gly Thr Asp Trp Val Ala Ser Thr Asp Lys
            485                 490                 495

Asp Phe Arg Pro Leu Ile Thr Val Trp Trp Pro Asn Lys Asp Ile Gln
        500                 505                 510

Val Asn Tyr Leu Lys Leu Met Gln Gln Ile Gly Ile Leu Asp Asn Ser
    515                 520                 525

Val Val Phe Asp Thr Asn Asn Asp Gln Leu Val Leu Asn Lys Gly Ala
530                 535                 540

Glu Ser Ala Gln Ile Gly Ile Glu Lys Lys Val Ser Glu Thr Gly Asn
545                 550                 555                 560

Thr Asp Trp Leu Asn Glu Leu Leu Phe Ala Pro Asn Gly Asn Gln Pro
            565                 570                 575

Ser Phe Ile Lys Gln Gln Tyr Leu Trp Asn Val Asp Ser Glu Tyr Pro
        580                 585                 590

Gly Gly Trp Phe Gln Gly Gly Tyr Leu Ala Tyr Gln Asn Ser Asp Leu
    595                 600                 605

Thr Pro Tyr Ala Asn Thr Pro Asp Tyr Arg Thr His Asn Gly Leu
610                 615                 620

Glu Phe Leu Leu Ala Asn Asp Val Asp Asn Ser Asn Pro Val Val Gln
625                 630                 635                 640

Ala Glu Gln Leu Asn Trp Leu Tyr Tyr Leu Met Asn Phe Gly Gln Ile

-continued

```
                645                 650                 655
Thr Ala Asn Asp Ser Asn Ala Asn Phe Asp Ser Met Arg Ile Asp Ala
                    660                 665                 670
Ile Ser Phe Val Asp Pro Gln Ile Ala Lys Lys Ala Tyr Asp Leu Leu
                675                 680                 685
Asp Lys Met Tyr Gly Leu Thr Asp Asn Glu Ala Val Ala Asn Gln His
    690                 695                 700
Ile Ser Ile Val Glu Ala Pro Lys Gly Glu Thr Pro Ile Thr Val Glu
705                 710                 715                 720
Lys Gln Ser Ala Leu Val Glu Ser Asn Trp Arg Asp Arg Met Lys Gln
                725                 730                 735
Ser Leu Ser Lys Asn Ala Thr Leu Asp Lys Leu Asp Pro Asp Pro Ala
                740                 745                 750
Ile Asn Ser Leu Glu Lys Leu Val Ala Asp Leu Val Asn Arg Ser
                755                 760                 765
Gln Ser Ser Asp Lys Asp Ser Ser Thr Ile Pro Asn Tyr Ser Ile Val
    770                 775                 780
His Ala His Asp Lys Asp Ile Gln Asp Thr Val Ile His Ile Met Lys
785                 790                 795                 800
Ile Val Asn Asn Pro Asn Ile Ser Met Ser Asp Phe Thr Met Gln
                805                 810                 815
Gln Leu Gln Asn Gly Leu Lys Ala Phe Tyr Glu Asp Gln His Gln Ser
                820                 825                 830
Val Lys Lys Tyr Asn Gln Tyr Asn Ile Pro Ser Ala Tyr Ala Leu Leu
                835                 840                 845
Leu Thr Asn Lys Asp Thr Val Pro Arg Val Phe Tyr Gly Asp Met Tyr
850                 855                 860
Gln Asp Tyr Gly Asp Asp Leu Asp Gly Gln Tyr Met Ala Thr Lys
865                 870                 875                 880
Ser Ile Tyr Tyr Asn Ala Ile Glu Gln Met Met Lys Ala Arg Leu Lys
                885                 890                 895
Tyr Val Ala Gly Gly Gln Ile Met Ala Val Thr Lys Ile Lys Asn Asp
                900                 905                 910
Gly Ile Asn Lys Asp Gly Thr Asn Lys Ser Gly Glu Val Leu Thr Ser
                915                 920                 925
Val Arg Phe Gly Lys Asp Ile Met Asp Ala Gln Gly Gln Gly Thr Ala
                930                 935                 940
Glu Ser Arg Asn Gln Gly Ile Gly Val Ile Val Ser Asn Ser Ser Gly
945                 950                 955                 960
Leu Glu Leu Lys Asn Ser Asp Ser Ile Thr Leu His Met Gly Ile Ala
                965                 970                 975
His Lys Asn Gln Ala Tyr Arg Ala Leu Met Leu Thr Asn Asp Lys Gly
                980                 985                 990
Ile Val Asn Tyr Asp Gln Asp Asn Asn Ala Pro Ile Ala Trp Thr Asn
                995                 1000                1005
Asp His Gly Asp Leu Ile Phe Thr Asn Gln Met Ile Asn Gly Gln Ser
    1010                1015                1020
Asp Thr Ala Val Lys Gly Tyr Leu Asn Pro Glu Val Ala Gly Tyr Leu
1025                1030                1035                1040
Ala Val Trp Val Pro Val Gly Ala Asn Asp Asn Gln Asp Ala Arg Thr
                1045                1050                1055
Val Thr Thr Asn Gln Lys Asn Thr Asp Gly Lys Val Leu His Thr Asn
                1060                1065                1070
```

```
Ala Ala Leu Asp Ser Lys Leu Met Tyr Glu Gly Phe Ser Asn Phe Gln
        1075                1080                1085

Lys Met Pro Thr Arg Gly Asn Gln Tyr Ala Asn Val Val Ile Thr Lys
    1090                1095                1100

Asn Ile Asp Leu Phe Lys Ser Trp Gly Ile Thr Asp Phe Glu Leu Ala
1105                1110                1115                1120

Pro Gln Tyr Arg Ser Ser Asp Gly Lys Asp Ile Thr Asp Arg Phe Leu
            1125                1130                1135

Asp Ser Ile Val Gln Asn Gly Tyr Gly Leu Ser Asp Arg Tyr Asp Leu
        1140                1145                1150

Gly Phe Lys Thr Pro Thr Lys Tyr Gly Thr Gln Asp Leu Arg Lys
    1155                1160                1165

Ala Ile Glu Arg Leu His Gln Ala Gly Met Ser Val Met Ala Asp Phe
    1170                1175                1180

Val Ala Asn Gln Ile Tyr Gly Leu His Ala Asp Lys Glu Val Val Ser
1185                1190                1195                1200

Ala Gln His Val Asn Ile Asn Gly Asp Thr Lys Leu Val Val Asp Pro
            1205                1210                1215

Arg Tyr Gly Thr Gln Met Thr Val Val Asn Ser Val Gly Gly Gly Asp
        1220                1225                1230

Tyr Gln Ala Lys Tyr Gly Gly Glu Tyr Leu Asp Thr Ile Ser Lys Leu
    1235                1240                1245

Tyr Pro Gly Leu Leu Leu Asp Ser Asn Gly Gln Lys Ile Asp Leu Ser
1250                1255                1260

Thr Lys Ile Lys Glu Trp Ser Ala Lys Tyr Leu Asn Gly Ser Asn Ile
1265                1270                1275                1280

Pro Gln Val Gly Met Gly Tyr Val Leu Lys Asp Trp Asn Asn Gly Gln
            1285                1290                1295

Tyr Phe His Ile Leu Asp Lys Glu Gly Gln Tyr Ser Leu Pro Thr Gln
        1300                1305                1310

Leu Val Ser Asn Asp Pro Glu Thr Gln Ile Gly Glu Ser Val Asn Tyr
    1315                1320                1325

Lys Tyr Phe Ile Gly Asn Ser Asp Ala Thr Tyr Asn Met Tyr His Asn
    1330                1335                1340

Leu Pro Asn Thr Val Ser Leu Ile Asn Ser Gln Glu Gly Gln Ile Lys
1345                1350                1355                1360

Thr Gln Gln Ser Gly Val Thr Ser Asp Tyr Glu Gly Gln Gln Val Gln
            1365                1370                1375

Val Thr Arg Gln Tyr Thr Asp Ser Lys Gly Val Ser Trp Asn Leu Ile
        1380                1385                1390

Thr Phe Ala Gly Gly Asp Leu Gln Gly Gln Lys Leu Trp Val Asp Ser
    1395                1400                1405

Arg Ala Leu Thr Met Thr Pro Phe Lys Thr Met Asn Gln Ile Ser Phe
    1410                1415                1420

Ile Ser Tyr Ala Asn Arg Asn Asp Gly Leu Phe Leu Asn Ala Pro Tyr
1425                1430                1435                1440

Gln Val Lys Gly Tyr Gln Leu Ala Gly Met Ser Asn Gln Tyr Lys Gly
            1445                1450                1455

Gln Gln Val Thr Ile Ala Gly Val Ala Asn Val Ser Gly Lys Asp Trp
        1460                1465                1470

Ser Leu Ile Ser Phe Asn Gly Thr Gln Tyr Trp Ile Asp Ser Gln Ala
    1475                1480                1485
```

-continued

```
Leu Asn Thr Asn Phe Thr His Asp Met Asn Gln Lys Val Phe Val Asn
    1490                1495                1500

Thr Thr Ser Asn Leu Asp Gly Leu Phe Leu Asn Ala Pro Tyr Arg Gln
1505                1510                1515                1520

Pro Gly Tyr Lys Leu Ala Gly Leu Ala Lys Asn Tyr Asn Asn Gln Thr
            1525                1530                1535

Val Thr Val Ser Gln Gln Tyr Phe Asp Asp Gln Gly Thr Val Trp Ser
        1540                1545                1550

Glu Val Val Leu Gly Gly Gln Thr Val Trp Val Asp Asn His Ala Leu
            1555                1560                1565

Ala Gln Met Gln Val Ser Asp Thr Ser Gln Gln Leu Tyr Val Asn Ser
    1570                1575                1580

Asn Gly Arg Asn Asp Gly Leu Phe Leu Asn Ala Pro Tyr Arg Gly Gln
1585                1590                1595                1600

Gly Ser Gln Leu Ile Gly Met Thr Ala Asp Tyr Asn Gly Gln His Val
            1605                1610                1615

Gln Val Thr Lys Gln Gly Gln Asp Ala Tyr Gly Ala Gln Trp Arg Leu
        1620                1625                1630

Ile Thr Leu Asn Asn Gln Gln Val Trp Val Asp Ser Arg Ala Leu Ser
            1635                1640                1645

Thr Thr Ile Val Gln Ala Met Asn Asp Asp Met Tyr Val Asn Ser Asn
1650                1655                1660

Gln Arg Thr Asp Gly Leu Trp Leu Asn Ala Pro Tyr Thr Met Ser Gly
1665                1670                1675                1680

Ala Lys Trp Ala Gly Asp Thr Arg Ser Ala Asn Gly Arg Tyr Val His
            1685                1690                1695

Ile Ser Lys Ala Tyr Ser Asn Glu Val Gly Asn Thr Tyr Tyr Leu Thr
        1700                1705                1710

Asn Leu Asn Gly Gln Ser Thr Trp Ile Asp Lys Arg Ala Phe Thr Ala
            1715                1720                1725

Thr Phe Asp Gln Val Val Ala Leu Asn Ala Thr Ile Val Ala Arg Gln
    1730                1735                1740

Arg Pro Asp Gly Met Phe Lys Thr Ala Pro Tyr Gly Glu Ala Gly Ala
1745                1750                1755                1760

Gln Phe Val Asp Tyr Val Thr Asn Tyr Asn Gln Gln Thr Val Pro Val
            1765                1770                1775

Thr Lys Gln His Ser Asp Ala Gln Gly Asn Gln Trp Tyr Leu Ala Thr
        1780                1785                1790

Val Asn Gly Thr Gln Tyr Trp Ile Asp Gln Arg Ser Phe Ser Pro Val
            1795                1800                1805

Val Thr Lys Val Val Asp Tyr Gln Ala Lys Ile Val Pro Arg Thr Thr
1810                1815                1820

Arg Asp Gly Val Phe Ser Gly Ala Pro Tyr Gly Glu Val Asn Ala Lys
1825                1830                1835                1840

Leu Val Asn Met Ala Thr Ala Tyr Gln Asn Gln Val Val His Ala Thr
            1845                1850                1855

Gly Glu Tyr Thr Asn Ala Ser Gly Ile Thr Trp Ser Gln Phe Ala Leu
        1860                1865                1870

Ser Gly Gln Glu Asp Lys Leu Trp Ile Asp Lys Arg Ala Leu Gln Ala
            1875                1880                1885

<210> SEQ ID NO 17
<211> LENGTH: 1425
<212> TYPE: PRT
```

<213> ORGANISM: Leuconostoc mesenteroides NRRL B-1355

<400> SEQUENCE: 17

```
Met Glu Gln Gln Glu Thr Val Thr Arg Lys Lys Leu Tyr Lys Ser Gly
1               5                   10                  15

Lys Val Trp Val Ala Ala Thr Ala Phe Ala Val Leu Gly Val Ser
            20                  25                  30

Thr Val Thr Thr Val His Ala Asp Thr Asn Ser Asn Val Ala Val Lys
            35                  40                  45

Gln Ile Asn Asn Thr Gly Thr Asn Asp Ser Gly Glu Lys Lys Val Pro
        50                  55                  60

Val Pro Ser Thr Asn Asn Asp Ser Leu Lys Gln Gly Thr Asp Gly Phe
65                  70                  75                  80

Trp Tyr Asp Ser Asp Gly Asn Arg Val Asp Gln Lys Thr Asn Gln Ile
                85                  90                  95

Leu Leu Thr Ala Glu Gln Leu Lys Lys Asn Asn Glu Lys Asn Leu Ser
            100                 105                 110

Val Ile Ser Asp Asp Thr Ser Lys Lys Asp Asp Glu Asn Ile Ser Lys
        115                 120                 125

Gln Thr Lys Ile Ala Asn Gln Gln Thr Val Asp Thr Ala Lys Gly Leu
    130                 135                 140

Thr Thr Ser Asn Leu Ser Asp Pro Ile Thr Gly Gly His Tyr Glu Asn
145                 150                 155                 160

His Asn Gly Tyr Phe Val Tyr Ile Asp Ala Ser Gly Lys Gln Val Thr
                165                 170                 175

Gly Leu Gln Asn Ile Asp Gly Asn Leu Gln Tyr Phe Asp Asn Gly
            180                 185                 190

Tyr Gln Val Lys Gly Ser Phe Arg Asp Val Asn Gly Lys His Ile Tyr
        195                 200                 205

Phe Asp Ser Val Thr Gly Lys Ala Ser Ser Asn Val Asp Ile Val Asn
    210                 215                 220

Gly Lys Ala Gln Gly Tyr Asp Ala Gln Gly Asn Gln Leu Lys Lys Ser
225                 230                 235                 240

Tyr Val Ala Asp Ser Ser Gly Gln Thr Tyr Tyr Phe Asp Gly Asn Gly
                245                 250                 255

Gln Pro Leu Ile Gly Leu Gln Thr Ile Asp Gly Asn Leu Gln Tyr Phe
            260                 265                 270

Asn Gln Gln Gly Val Gln Ile Lys Gly Gly Phe Gln Asp Val Asn Asn
        275                 280                 285

Lys Arg Ile Tyr Phe Ala Pro Asn Thr Gly Asn Ala Val Ala Asn Thr
    290                 295                 300

Glu Ile Ile Asn Gly Lys Leu Gln Gly Arg Asp Ala Asn Gly Asn Gln
305                 310                 315                 320

Val Lys Asn Ala Phe Ser Lys Asp Val Ala Gly Asn Thr Phe Tyr Phe
                325                 330                 335

Asp Ala Asn Gly Val Met Leu Thr Gly Leu Gln Thr Ile Ser Gly Lys
            340                 345                 350

Thr Tyr Tyr Leu Asp Glu Gln Gly His Leu Arg Lys Asn Tyr Ala Gly
        355                 360                 365

Thr Phe Asn Asn Gln Phe Met Tyr Phe Asp Ala Asp Thr Gly Ala Gly
    370                 375                 380

Lys Thr Ala Ile Glu Tyr Gln Phe Asp Gln Gly Leu Val Ser Gln Ser
385                 390                 395                 400
```

-continued

Asn Glu Asn Thr Pro His Asn Ala Ala Lys Ser Tyr Asp Lys Ser Ser
                405                 410                 415

Phe Glu Asn Val Asp Gly Tyr Leu Thr Ala Asp Thr Trp Tyr Arg Pro
            420                 425                 430

Thr Asp Ile Leu Lys Asn Gly Asp Thr Trp Thr Ala Ser Thr Glu Thr
        435                 440                 445

Asp Met Arg Pro Leu Leu Met Thr Trp Trp Pro Asp Lys Gln Thr Gln
    450                 455                 460

Ala Asn Tyr Leu Asn Phe Met Ser Ser Lys Gly Leu Gly Ile Thr Thr
465                 470                 475                 480

Thr Tyr Thr Ala Ala Thr Ser Gln Lys Thr Leu Asn Asp Ala Ala Phe
                485                 490                 495

Val Ile Gln Thr Ala Ile Glu Gln Ile Ser Leu Lys Lys Ser Thr
            500                 505                 510

Glu Trp Leu Arg Asp Ala Ile Asp Ser Phe Val Lys Thr Gln Ala Asn
        515                 520                 525

Trp Asn Lys Gln Thr Glu Asp Glu Ala Phe Asp Gly Leu Gln Trp Leu
    530                 535                 540

Gln Gly Gly Phe Leu Ala Tyr Gln Asp Asp Ser His Arg Thr Pro Asn
545                 550                 555                 560

Thr Asp Ser Gly Asn Asn Arg Lys Leu Gly Arg Gln Pro Ile Asn Ile
                565                 570                 575

Asp Gly Ser Lys Asp Thr Thr Asp Gly Lys Gly Ser Glu Phe Leu Leu
            580                 585                 590

Ala Asn Asp Ile Asp Asn Ser Asn Pro Ile Val Gln Ala Glu Gln Leu
        595                 600                 605

Asn Trp Leu His Tyr Leu Met Asn Phe Gly Ser Ile Thr Gly Asn Asn
    610                 615                 620

Asp Asn Ala Asn Phe Asp Gly Ile Arg Val Asp Ala Val Asp Asn Val
625                 630                 635                 640

Asp Ala Asp Leu Leu Lys Ile Ala Gly Asp Tyr Phe Lys Ala Leu Tyr
                645                 650                 655

Gly Thr Asp Lys Ser Asp Ala Asn Ala Asn Lys His Leu Ser Ile Leu
            660                 665                 670

Glu Asp Trp Asn Gly Lys Asp Pro Gln Tyr Val Asn Gln Gln Gly Asn
        675                 680                 685

Ala Gln Leu Thr Met Asp Tyr Thr Val Thr Ser Gln Phe Gly Asn Ser
    690                 695                 700

Leu Thr His Gly Ala Asn Asn Arg Ser Asn Met Trp Tyr Phe Leu Asp
705                 710                 715                 720

Thr Gly Tyr Tyr Leu Asn Gly Asp Leu Asn Lys Lys Ile Val Asp Lys
                725                 730                 735

Asn Arg Pro Asn Ser Gly Thr Leu Val Asn Arg Ile Ala Asn Ser Gly
            740                 745                 750

Asp Thr Lys Val Ile Pro Asn Tyr Ser Phe Val Arg Ala His Asp Tyr
        755                 760                 765

Asp Ala Gln Asp Pro Ile Arg Lys Ala Met Ile Asp His Gly Ile Ile
    770                 775                 780

Lys Asn Met Gln Asp Thr Phe Thr Phe Asp Gln Leu Ala Gln Gly Met
785                 790                 795                 800

Glu Phe Tyr Tyr Lys Asp Gln Glu Asn Pro Ser Gly Phe Lys Lys Tyr
                805                 810                 815

Asn Asp Tyr Asn Leu Pro Ser Ala Tyr Ala Met Leu Leu Thr Asn Lys

```
              820                 825                 830
Asp Thr Val Pro Arg Val Tyr Tyr Gly Asp Met Tyr Leu Glu Gly Gly
                835                 840                 845
Gln Tyr Met Glu Lys Gly Thr Ile Tyr Asn Pro Val Ile Ser Ala Leu
        850                 855                 860
Leu Lys Ala Arg Ile Lys Tyr Val Ser Gly Gln Thr Met Ala Thr
865                 870                 875                 880
Asp Ser Ser Gly Lys Asp Leu Lys Asp Gly Glu Thr Asp Leu Leu Thr
                885                 890                 895
Ser Val Arg Phe Gly Lys Gly Ile Met Thr Ser Asp Gln Thr Thr Thr
                900                 905                 910
Gln Asp Asn Ser Gln Asp Tyr Lys Asn Gln Gly Ile Gly Val Ile Val
                915                 920                 925
Gly Asn Asn Pro Asp Leu Lys Leu Asn Asn Asp Lys Thr Ile Thr Leu
                930                 935                 940
His Met Gly Lys Ala His Lys Asn Gln Leu Tyr Arg Ala Leu Val Leu
945                 950                 955                 960
Ser Asn Asp Ser Gly Ile Asp Val Tyr Asp Ser Asp Lys Ala Pro
                965                 970                 975
Thr Leu Arg Thr Asn Asp Asn Gly Asp Leu Ile Phe His Lys Thr Asn
                980                 985                 990
Thr Phe Val Lys Gln Asp Gly Thr Ile Ile Asn Tyr Glu Met Lys Gly
                995                1000                1005
Ser Leu Asn Ala Leu Ile Ser Gly Tyr Leu Gly Val Trp Val Pro Val
           1010                1015                1020
Gly Ala Ser Asp Ser Gln Asp Ala Arg Thr Val Ala Thr Glu Ser Ser
1025                1030                1035                1040
Ser Ser Asn Asp Gly Ser Val Phe His Ser Asn Ala Ala Leu Asp Ser
                1045                1050                1055
Asn Val Ile Tyr Glu Gly Phe Ser Asn Phe Gln Ala Met Pro Thr Ser
                1060                1065                1070
Pro Glu Gln Ser Thr Asn Val Val Ile Ala Thr Lys Ala Asn Leu Phe
                1075                1080                1085
Lys Glu Leu Gly Ile Thr Ser Phe Glu Leu Ala Pro Gln Tyr Arg Ser
                1090                1095                1100
Ser Gly Asp Thr Asn Tyr Gly Gly Met Ser Phe Leu Asp Ser Phe Leu
1105                1110                1115                1120
Asn Asn Gly Tyr Ala Phe Thr Asp Arg Tyr Asp Leu Gly Phe Asn Lys
                1125                1130                1135
Ala Asp Gly Asn Pro Asn Pro Thr Lys Tyr Gly Thr Asp Gln Asp Leu
                1140                1145                1150
Arg Asn Ala Ile Glu Ala Leu His Lys Asn Gly Met Gln Ala Ile Ala
                1155                1160                1165
Asp Trp Val Pro Asp Gln Ile Tyr Ala Leu Pro Gly Lys Glu Val Val
                1170                1175                1180
Thr Ala Thr Arg Val Asp Glu Arg Gly Asn Gln Leu Lys Asp Thr Asp
1185                1190                1195                1200
Phe Val Asn Leu Leu Tyr Val Ala Asn Thr Lys Ser Ser Gly Val Asp
                1205                1210                1215
Tyr Gln Ala Lys Tyr Gly Gly Glu Phe Leu Asp Lys Leu Arg Glu Glu
                1220                1225                1230
Tyr Pro Ser Leu Phe Lys Gln Asn Gln Val Ser Thr Gly Gln Pro Ile
                1235                1240                1245
```

```
Asp Ala Ser Thr Lys Ile Lys Gln Trp Ser Ala Lys Tyr Met Asn Gly
    1250                1255                1260

Thr Asn Ile Leu His Arg Gly Ala Tyr Tyr Val Leu Lys Asp Trp Ala
1265                1270                1275                1280

Thr Asn Gln Tyr Phe Asn Ile Ala Lys Thr Asn Glu Val Phe Leu Pro
                1285                1290                1295

Leu Gln Leu Gln Asn Lys Asp Ala Gln Thr Gly Phe Ile Ser Asp Ala
            1300                1305                1310

Ser Gly Val Lys Tyr Tyr Ser Ile Ser Gly Tyr Gln Ala Lys Asp Thr
        1315                1320                1325

Phe Ile Glu Asp Gly Asn Gly Asn Trp Tyr Tyr Phe Asp Lys Asp Gly
    1330                1335                1340

Tyr Met Val Arg Ser Gln Gln Gly Glu Asn Pro Ile Arg Thr Val Glu
1345                1350                1355                1360

Thr Ser Val Asn Thr Arg Asn Gly Asn Tyr Tyr Phe Met Pro Asn Gly
                1365                1370                1375

Val Glu Leu Arg Lys Gly Phe Gly Thr Asp Asn Ser Gly Asn Val Tyr
            1380                1385                1390

Tyr Phe Asp Asp Gln Gly Lys Met Val Arg Asp Lys Tyr Ile Asn Asp
        1395                1400                1405

Asp Ala Asn Asn Phe Tyr His Leu Asn Val Asp Gly Thr Met Ser Arg
    1410                1415                1420

Gly
1425

<210> SEQ ID NO 18
<211> LENGTH: 473
<212> TYPE: PRT
<213> ORGANISM: Bacillus subtilis NCIMB 11871

<400> SEQUENCE: 18

Met Asn Ile Lys Lys Phe Ala Lys Gln Ala Thr Val Leu Thr Phe Thr
1               5                   10                  15

Thr Ala Leu Leu Ala Gly Gly Ala Thr Gln Ala Phe Ala Lys Glu Thr
            20                  25                  30

Asn Gln Lys Pro Tyr Lys Glu Thr Tyr Gly Ile Ser His Ile Thr Arg
        35                  40                  45

His Asp Met Leu Gln Ile Pro Glu Gln Gln Lys Asn Glu Lys Tyr Gln
    50                  55                  60

Val Pro Glu Phe Asp Ser Ser Thr Ile Lys Asn Ile Ser Ser Ala Lys
65                  70                  75                  80

Gly Leu Asp Val Trp Asp Ser Trp Pro Leu Gln Asn Ala Asp Gly Thr
                85                  90                  95

Val Ala Asn Tyr His Gly Tyr His Ile Val Phe Ala Leu Ala Gly Asp
            100                 105                 110

Pro Lys Asn Ala Asp Asp Thr Ser Ile Tyr Met Phe Tyr Gln Lys Val
        115                 120                 125
```

-continued

```
Gly Glu Thr Ser Ile Asp Ser Trp Lys Asn Ala Gly Arg Val Phe Lys
130                 135                 140

Asp Ser Asp Lys Phe Asp Ala Asn Asp Ser Ile Leu Lys Asp Gln Thr
145                 150                 155                 160

Gln Glu Trp Ser Gly Ser Ala Thr Phe Thr Ser Asp Gly Lys Ile Arg
                165                 170                 175

Leu Phe Tyr Thr Asp Phe Ser Gly Lys His Tyr Gly Lys Gln Thr Leu
                180                 185                 190

Thr Thr Ala Gln Val Asn Val Ser Ala Ser Asp Ser Ser Leu Asn Ile
                195                 200                 205

Asn Gly Val Glu Asp Tyr Lys Ser Ile Phe Asp Gly Asp Gly Lys Thr
210                 215                 220

Tyr Gln Asn Val Gln Gln Phe Ile Asp Glu Gly Asn Tyr Ser Ser Gly
225                 230                 235                 240

Asp Asn His Thr Leu Arg Asp Pro His Tyr Val Glu Asp Lys Gly His
                245                 250                 255

Lys Tyr Leu Val Phe Glu Ala Asn Thr Gly Thr Glu Asp Gly Tyr Gln
                260                 265                 270

Gly Glu Glu Ser Leu Phe Asn Lys Ala Tyr Tyr Gly Lys Ser Thr Ser
                275                 280                 285

Phe Phe Arg Gln Glu Ser Gln Lys Leu Leu Gln Ser Asp Lys Lys Arg
                290                 295                 300

Thr Ala Glu Leu Ala Asn Gly Ala Leu Gly Met Ile Glu Leu Asn Asp
305                 310                 315                 320

Asp Tyr Thr Leu Lys Lys Val Met Lys Pro Leu Ile Ala Ser Asn Thr
                325                 330                 335

Val Thr Asp Glu Ile Glu Arg Ala Asn Val Phe Lys Met Asn Gly Lys
                340                 345                 350

Trp Tyr Leu Phe Thr Asp Ser Arg Gly Ser Lys Met Thr Ile Asp Gly
                355                 360                 365

Ile Thr Ser Asn Asp Ile Tyr Met Leu Gly Tyr Val Ser Asn Ser Leu
                370                 375                 380

Thr Gly Pro Tyr Lys Pro Leu Asn Lys Thr Gly Leu Val Leu Lys Met
385                 390                 395                 400

Asp Leu Asp Pro Asn Asp Val Thr Phe Thr Tyr Ser His Phe Ala Val
                405                 410                 415

Pro Gln Ala Lys Gly Asn Asn Val Val Ile Thr Ser Tyr Met Thr Asn
                420                 425                 430

Arg Gly Phe Tyr Ala Asp Lys Gln Ser Thr Phe Ala Pro Ser Phe Leu
                435                 440                 445

Leu Asn Ile Lys Gly Lys Lys Thr Ser Val Val Lys Asp Ser Ile Leu
                450                 455                 460

Glu Gln Gly Gln Leu Thr Val Asn Lys
465                 470
```

ENZYMATIC PRODUCTION OF GLYCOSYLATED SYNTHONS

FIELD OF THE INVENTION

The present invention relates to the field of the enzymatic glycosylation of hydroxylated synthons in order to obtain glycosylated monomers.

The present invention also relates to novel routes for the chemo-enzymatic synthesis of glyco(co)polymers based on chemical polymerization or on a chemical coupling reaction of glycosylated monomers obtained enzymatically.

PRIOR ART

Glyco(co)polymers have aroused increasing interest in recent years as a result of their great potential in many biotechnological and industrial sectors.

The introduction of carbohydrate units into synthetic macromolecules may give the polymers novel physico-chemical properties, for example it may increase their solubilities, modify their hydrophobic nature, and thus offer access to novel industrial applications. In the biomedical sectors, these glyco(co)polymers have aroused keen interest for the manufacture of biomaterials intended for repairing lesions, tissue engineering (Cho et al., Biomaterials. 2006 February; 27(4): 576-85. Epub. 2005 Aug. 8), the vectorization of active principles (Ahmes and Narain, Biomaterials. 2011 August; 32(22): 5279-90), or for modifying and rendering biocompatible a hydrophobic surface. Similarly, glyco(co)polymers are particularly advantageous in the field of biological diagnosis (Abraham et al., Biomaterials. 2005 August; 26(23): 4767-78), as support for the covalent coupling of biomolecules, or as multivalent architectures for promoting recognition processes with certain proteins (Spain et al., Polym. Chem., 2011, 2, 60-68; Vasquez-Dorbatt et al., Chembiochem. 2012 Nov. 26; 13(17): 2478-87).

In view of the wide array of uses of this class of macromolecules, the development of efficient synthetic routes for gaining access to glyco(co)polymers with controlled structures and functionalities and also to complex and original macromolecular architectures is a major challenge.

In recent years, considerable efforts have been devoted toward the development of increasingly sophisticated chemical synthetic routes for better controlling the glycosylation of synthetic polymers.

Specifically, increasing interest is shown in hybrid glycopolymers, which differ from natural polysaccharides, and which are formed from a synthetic part, of (meth)acrylate, (meth)acrylamide, styrene, norbornenyl, vinyl acetate, peptide, etc. type, and a carbohydrate part.

Various methods for synthesizing glyco(co)polymers comprising a synthetic backbone bearing carbohydrate groups have been explored in the past (Ladmiral et al., Eur. Polym. J., 2004, 40, 431-449; Spain et al., J. Polym. Sci. Part. A-Polym. Chem., 2007, 45, 2059-2072), these methods consisting in:

chemical glycosylation of synthetic polymers.

However, this method has the drawback of often leading to low degrees of functionalization linked to problems of steric hindrance.

To circumvent this problem, the reactive functions borne by the polymer must be distanced from the polymer backbone so as to increase the reactivity while at the same time reducing the steric hindrance generated by the grafting of the pendent saccharide blocks.

In this case also, this requires the production of reactive synthons and the polymerization of unconventional monomers (Slavin et al., Eur. Polym. J., 2011, 47, 435-446).

polymerization (anionic, radical or via ring opening) of glycosylated monomers, mainly obtained chemically, after several steps and in particular steps of selective protection/deprotection of the hydroxyl functions of the sugars.

The glycosylation of synthons is nowadays mainly performed chemically, thus requiring laborious multi-step processes that are difficult to control. This is the most widespread production route.

In general, the synthesis of glycomonomers often proves to be very tedious, requiring time-intensive protection and deprotection steps and also the use of toxic metal catalysts or solvents. Furthermore, the diversity of the saccharide structures accessible via these routes still remains limited. Finally, in certain cases, mixtures of undesirable structures are obtained, making it difficult to control the polymerization reaction and, thereafter, the structure and properties of the polymers.

For example, the synthesis of glucosylated 2-(hydroxy) ethyl methacrylate (HEMA), 2-methacryloyloxyethyl-$\alpha$-D-glucopyranoside (MEGlc), to which the present invention relates, has hitherto only been performed chemically.

In particular, Kitazawa (Kitazawa et al., Chem. Lett., 1990, 19, No. 9, 1733-1736) proposed a synthesis based on the use of a glucose donor such as methylglucoside, phosphomolybdic acid as catalyst and 2,4-dinitrochlorobenzene as inhibitor. However, the stereoselectivity of this method is low.

Similarly, in 1993, Nakaya (Nakaya et al., Makromol. Chem., Rapid. Commun., 1993, 14, 77-83) synthesized another glucopolymer by reacting HEMA with 2,3,4,6-tetra-O-acetyl-$\alpha$-D-glucopyranose bromide in the presence of silver oxide or mercury cyanide, according to the Helferich method (Helferich and Weis, Chem. Ber., 1956, 89, 314-321).

In order to improve the yields and to avoid the use of toxic mercury salts, another chemical route was proposed by Ambrosi in 2002 (Ambrosi et al., J. Chem. Soc., Perkin Trans. 1, 2002, 45-52). The glucosylation was then performed by coupling the glucose donor, 2,3,4,6-tetra-O-acetyl-$\alpha$-D-glucopyranose bromide, with the acceptor, HEMA, in anhydrous dichloromethane, using silver trifluoromethanesulfonate as catalyst. However, the reaction lasts six days and the yield is 80%. The polymer is then obtained by radical polymerization.

In the face of the various problems mentioned previously, enzymatic processes are very favorably positioned on account of the specificity and selectivity of action of enzymes to overcome the difficulties of chemical synthesis and to propose an "eco-compatible" alternative, reducing not only the use of harmful products (metal catalysts, organic solvents), but also the costs and time for producing the glycosylated monomers.

A large number of enzymes responsible for the synthesis, degradation and modification of carbohydrates are at the present time listed in nature. What is more, this diversity may be considerably extended with the aid of enzymatic engineering techniques allowing biocatalysts to be tailor-made or improved.

However, despite the great potential for innovation, enzymatic routes for producing glycosylated synthons have been little explored to date.

In the 1990s, Kobayashi described the use of a $\beta$-galactosidase with 4-nitrophenyl N-acetyl-$\beta$-D-glucosaminide and lactose as substrates to give p-nitrophenyl N-acetyl-β-lactosaminide (Kobayashi et al., J. Carbohydr. Chem., 1994, 13, 753-766). This enzymatic step is followed by reduction of the nitro function to an amine function, followed by attaching an acrylate function.

In the 2000s, lipases were used for the esterification of various sugars with (meth)acrylates, but with limited yields and selectivities (Albertin et al., Macromolecules, 2004, 37 (20), pages 7530-7537; Miura et al., J. Polym. Sci. Part A-Polym. Chem., 2004, 42, 4598-4606; Park et al., J. Biomed. Mater. Res. A, 2004 Dec. 1; 71(3): 497-507; Kulshrestha et al., ACS Symp. Ser., 2005, vol. 900, pages 327-342; Tsukamoto et al., J. Chem. Technol. Biotechnol., 2008, 83, 1486-1492).

Very recently, routes for the enzymatic production of unsaturated glycosides of vinyl type have been proposed with the aid of glycoside-hydrolases used in synthesis, either in a reverse hydrolysis reaction with thermodynamic control, or in a trans-glycosylation reaction with kinetic control (Kloosterman et al., Green Chem., 2014, 16, 203-210; Kloosterman et al., Green Chem., 2014, 16, 1837-1846; Kloosterman et al., Macromol. Biosci., 2014, 14 (9), 1268-1279; US2012/0028308; US2012/0028307; Mazzocchetti et al., Macromol. Biosci. 2014 February; 14(2): 186-94).

However, all these processes are insufficient in terms of yield, reaction rate and selectivity. The size and diversity of the sugars that may be obtained on conclusion of these processes are also limited.

There is consequently a need, in the state of the art, for an enzymatic process allowing the glycosylation of structurally very variable hydroxylated synthons.

There is a need for a process for the glycosylation of hydroxylated synthons which allows time and cost savings in the production of glycosylated synthons, or monomers.

There is also a need for a process for better controlling the degrees of glycosylation of the synthons and the structures, and also their distribution.

There is thus also a need for enzymes that are capable of glycosylating hydroxylated synthons of various nature, thus making it possible to produce a wide diversity of glycosylated synthons, or monomers, which are polymerizable or which may be coupled via a coupling reaction.

A need furthermore exists for a process for synthesizing glyco(co)polymers, making it possible advantageously to afford access to a wider diversity of macromolecular architectures for various fields of application (biomaterials, implant materials, tissue engineering, biological diagnosis, delivery of active principles, etc.).

There is a need for a process for synthesizing glyco(co)polymers which allows a saving in time and costs in the production of glyco(co)polymers.

There is also a need for processes that limit the use of products considered to be toxic.

The present invention makes it possible advantageously to satisfy all of these needs.

SUMMARY OF THE INVENTION

Thus, the present invention provides a process for manufacturing a glycosylated synthon, or monomer, comprising at least one step of placing at least one glycan-saccharase in contact with at least one hydroxylated synthon and at least one sucrose, in which:

(A) said hydroxylated synthon is chosen from the group consisting of:
(i) (meth)acrylate/(meth)acrylamide synthons of formula (I):

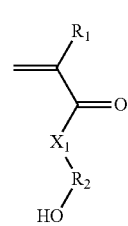

in which:
$R_1$ represents a hydrogen atom or a $C_1$-$C_3$ alkyl;
$R_2$ represents a $C_1$-$C_{20}$ alkylene group; or a group $(C_2H_4O)_n$, with n being an integer between 1 and 10; and
$X_1$ represents —(O)—, —(NH)—, —(S)— or —(NR'$_2$(OH))—, preferably —(O)—, —(NH)—, or —(NR'$_2$(OH))—, with R'$_2$ representing a $C_1$-$C_{20}$ alkylene group; or a group —$(C_2H_4O)_m$—, with m being an integer between 1 and 10;

(ii) styrene-based synthons of formula (II):

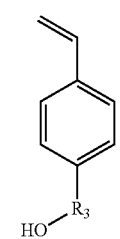

in which $R_3$ represents a covalent bond; a $C_1$-$C_{20}$ alkylene group; or a group $(C_2H_4O)_n$, with n being an integer between 1 and 10;

(iii) N-carboxyanhydride (NCA) synthons of formula (III):

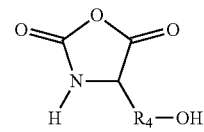

in which $R_4$ represents a covalent bond; a $C_1$-$C_{20}$ alkylene group; or a group $(C_2H_4O)_n$, with n being an integer between 1 and 10;

(iv) lactone/lactam/thiolactone synthons of formula (IV):

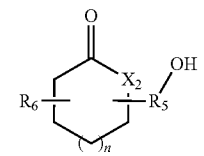

in which:
$R_5$ represents a covalent bond; a $C_1$-$C_{20}$ alkylene group; or a group $(C_2H_4O)_m$, with m being an integer between 1 and 10;
n represents an integer between 1 and 20;

$X_2$ represents —(O)—, —(NH)— or —(S)—; and
$R_6$ represents a hydrogen or a $C_1$-$C_{20}$ alkyl group;
(v) synthons of formula (V):

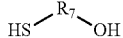

in which $R_7$ represents a $C_1$-$C_{20}$ alkylene group; and
(vi) synthons of formula (VI):

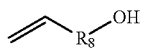

in which $R_8$ represents a $C_1$-$C_{20}$ alkylene group.

According to a particular embodiment, the hydroxylated synthon is chosen from the group consisting of:
(i) (meth)acrylate/(meth)acrylamide synthons of formula (I):

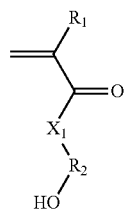

in which:
$R_1$ represents a hydrogen atom or a $C_1$-$C_3$ alkyl;
$R_2$ represents a $C_1$-$C_{20}$ alkylene group; or a group $(C_2H_4O)_n$, with n being an integer between 1 and 10; and
$X_1$ represents —(O)—, —(NH)—, —(S)— or —(NR'$_2$(OH))—, preferably —(O)—, —(NH)—, or —(NR'$_2$(OH))—, with R'$_2$ representing a $C_1$-$C_{20}$ alkylene group; or a group —(C$_2$H$_4$O)$_m$—, with m being an integer between 1 and 10;
(ii) styrene-based synthons of formula (II):

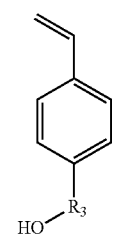

in which $R_3$ represents a covalent bond; a $C_1$-$C_{20}$ alkylene group; or a group $(C_2H_4O)_n$, with n being an integer between 1 and 10;
(iii) N-carboxyanhydride (NCA) synthons of formula (III):

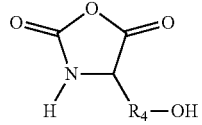

in which $R_4$ represents a covalent bond; a $C_1$-$C_{20}$ alkylene group; or a group $(C_2H_4O)_n$, with n being an integer between 1 and 10;
(iv) lactone/lactam/thiolactone synthons of formula (IV):

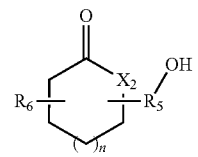

in which:
$R_5$ represents a covalent bond; a $C_1$-$C_{20}$ alkylene group; or a group $(C_2H_4O)_m$, with m being an integer between 1 and 10;
n represents an integer between 1 and 20;
$X_2$ represents —(O)—, —(NH)— or —(S)—; and
$R_6$ represents a hydrogen or a $C_1$-$C_{20}$ alkyl group; and
(vi) synthons of formula (VI):

(VI)

in which $R_8$ represents a $C_1$-$C_{20}$ alkylene group.

According to a preferred embodiment, the glycan-saccharase is chosen from the group comprising:
a sequence having at least 80% identity with SEQ ID NO: 1 (ASNp WT);
a sequence having at least 80% identity with SEQ ID NO: 1 mutated once at any one of the positions R226, I228, F229, A289, F290, I330, V331, D394 and R446;
a sequence having at least 80% identity with SEQ ID NO: 11 (DSR-S vardelΔ4N-S512C);
a sequence having at least 80% identity with SEQ ID NO: 12 (alpha-1,2 BrS);
a sequence having at least 80% identity with SEQ ID NO: 13 (ΔN$_{123}$-GBD-CD2);
a sequence having at least 80% identity with SEQ ID NO: 14 (ASDg);
a sequence having at least 80% identity with SEQ ID NO: 15 (DSR-S-OK);
a sequence having at least 80% identity with SEQ ID NO: 16 (alpha-1,3 BrS);
a sequence having at least 80% identity with SEQ ID NO: 17 (ASR-C-del-bis); and
a sequence having at least 80% identity with SEQ ID NO: 18 (fructosyltransferase of *Bacillus subtilis*).

More particularly, a sequence having at least 80% identity with SEQ ID NO: 1 mutated once at any one of the positions R226, I228, F229, A289, F290, I330, V331, D394 and R446 which may be chosen from:
a sequence having at least 80% identity with SEQ ID NO: 2 (ASNP R226X$_1$), said sequence having an amino acid X₁ representing an amino acid chosen from the group consisting of A, C, D, E, F, G, H, I, K, L, M, N, P, Q, S, T, V, W and Y;

a sequence having at least 80% identity with SEQ ID NO: 3 (ASNP I228X₂), said sequence having an amino acid X₂ representing an amino acid chosen from the group consisting of A, C, D, E, F, G, H, L, M, N, P, Q, R, S, T, V, W and Y;

a sequence having at least 80% identity with SEQ ID NO: 4 (ASNP F229X₃), said sequence having an amino acid X₃ representing an amino acid chosen from the group consisting of A, C, D, E, G, H, I, K, L, M, N, P, Q, R, S, T, V, W and Y;

a sequence having at least 80% identity with the sequence SEQ ID NO: 5 (ASNP A289X₄), said sequence having an amino acid X₄ representing an amino acid chosen from the group consisting of C, D, E, F, G, H, I, K, L, M, N, P, Q, R, S, T, V, W and Y;

a sequence having at least 80% identity with the sequence SEQ ID NO: 6 (ASNP F290X₅), said sequence having an amino acid X₅ representing an amino acid chosen from the group consisting of A, C, D, E, G, H, I, K, L, M, N, P, Q, R, S, T, V, W and Y;

a sequence having at least 80% identity with the sequence SEQ ID NO: 7 (ASNP I330X₆), said sequence having an amino acid X₆ representing an amino acid chosen from the group consisting of A, C, D, E, F, G, H, K, L, M, N, P, Q, R, S, T, V, W and Y;

a sequence having at least 80% identity with SEQ ID NO: 8 (ASNP V331X₇), said sequence having an amino acid X₇ representing an amino acid chosen from the group consisting of A, C, D, E, F, G, H, I, K, L, M, N, P, Q, R, S, T, W and Y;

a sequence having at least 80% identity with SEQ ID NO: 9 (ASNP D394X₈), said sequence having an amino acid X₈ representing an amino acid chosen from the group consisting of A, C, E, F, G, H, I, K, L, M, N, P, Q, R, S, T, V, W and Y; and a sequence having at least 80% identity with SEQ ID NO: 10 (ASNP R446X₉), said sequence having an amino acid X₉ representing an amino acid chosen from the group consisting of A, C, D, E, F, G, H, I, K, L, M, N, Q, S, T, V, W and Y.

In particular, a sequence having at least 80% identity with SEQ ID NO: 1 mutated once at any one of the positions R226, I228, F229, A289, F290, I330, V331, D394 and R446 may be chosen from:

a sequence having at least 80% identity with SEQ ID NO: 2 (ASNP R226X₁), said sequence having an amino acid X₁ representing an amino acid chosen from the group consisting of C, H, K, M, N, Q, S, T and V;

a sequence having at least 80% identity with SEQ ID NO: 3 (ASNP I228X₂), said sequence having an amino acid X₂ representing an amino acid chosen from the group consisting of H, L, T, V, W and Y;

a sequence having at least 80% identity with SEQ ID NO: 4 (ASNP F229$X_3$), said sequence having an amino acid $X_3$ representing an amino acid chosen from the group consisting of C, D, E, G, H, I, K, M, N, P, Q, V, W and Y, in particular of C, D, E, G, I, K, M, N, P, V, W and Y, and more preferentially of M and Y;

a sequence having at least 80% identity with the sequence SEQ ID NO: 5 (ASNP A289$X_4$), said sequence having an amino acid $X_4$ representing an amino acid chosen from the group consisting of C, D, E, F, M, N, P, Q, S, T, V and W and more particularly chosen from the group consisting of F, M, N, P, Q, S and T;

a sequence having at least 80% identity with the sequence SEQ ID NO: 6 (ASNP F290$X_5$), said sequence having an amino acid $X_5$ representing an amino acid chosen from the group consisting of A, C, D, E, G, H, I, K, L, M, P, Q, S, T, V and W, more preferentially of A, C, D, H, I, K, L, M, Q, S, T, V and W, in particular of A, C, I, L, V, S, T and W;

a sequence having at least 80% identity with the sequence SEQ ID NO: 7 (ASNP I330$X_6$), said sequence having an amino acid $X_6$ representing an amino acid chosen from the group consisting of A, C, D, E, F, G, H, K, L, M, N, Q, S, V and Y, in particular of A and C, more preferentially of A;

a sequence having at least 80% identity with SEQ ID NO: 8 (ASNP V331$X_7$), said sequence having an amino acid $X_7$ representing an amino acid chosen from the group consisting of A, C, D, E, F, G, H, I, K, L, N, Q, R, S, T, W and Y, more preferentially of C, D, E, F, G, N, R, S, T, W and Y, in particular of E, T and W;

a sequence having at least 80% identity with SEQ ID NO: 9 (ASNP D394$X_8$), said sequence having an amino acid $X_5$ representing an amino acid chosen from the group consisting of A, E, F, G, H, I, K and L, in particular of A and E;

a sequence having at least 80% identity with SEQ ID NO: 10 (ASNP R446$X_9$), said sequence having an amino acid $X_9$ representing an amino acid chosen from the group consisting of A, C, G, K, L, M, N, and S, in particular of A, N and M.

According to one embodiment of the invention, the hydroxylated synthon used is more particularly chosen from the group consisting of HEMA, NHAM, HEAA, VP, VBA, HMNCA, AHMCL, MVL, BME, allyl alcohol and NNHEA.

According to this embodiment, it is preferably chosen from HEMA, NHAM, HEAA, allyl alcohol, NNHEA and BME, in particular HEMA and NHAM.

According to one embodiment, a hydroxylated synthon according to the invention used in an enzymatic glycosylation process of the invention is glucosylated or fructosylated on conclusion of this process, preferably glucosylated.

A subject of the invention is also a process for manufacturing a glyco(co)polymer, comprising the polymerization of at least two monomers obtained, independently, on conclusion of the enzymatic glycosylation process according to the invention.

According to one embodiment, the process for manufacturing a glyco(co)polymer according to the invention comprises, in the following order, the following steps:

a) polymerization of two monomers obtained, independently of each other, on conclusion of the enzymatic glycosylation process according to the invention, making it possible to produce a chain of two monomers;

b) polymerization of the monomer chain obtained on conclusion of the preceding step with a monomer obtained on conclusion of the enzymatic glycosylation process according to the invention; and then c) one or more successive, and independent, steps consisting in polymerizing the monomer chain obtained on conclusion of the preceding step with a monomer obtained on conclusion of the enzymatic glycosylation process according to the invention.

The process for manufacturing a glyco(co)polymer according to this embodiment may also comprise, independently:

at least one step a') between steps a) and b);

at least one step b') between steps b) and c); and/or at least one step c') after any one of the steps c), in which the monomer chain obtained on conclusion of the preceding step is polymerized with at least one non-glycosylated synthon.

A subject of the invention is also a process for manufacturing a glyco(co)polymer, preferably a block polymer, comprising the coupling of at least two monomers obtained, independently, on conclusion of the enzymatic glycosylation process according to the invention, preferably of monomers obtained from synthons of formula (V) and/or (VI) according to the invention.

In the context of the present invention, and unless otherwise mentioned in the text, the following definitions apply:
alkyl: a saturated, linear or branched hydrocarbon-based aliphatic group, comprising from 1 to 20, especially from 1 to 10 and preferably from 1 to 6 carbon atoms; and
alkylene: a linear or branched, divalent alkylene group, comprising from 1 to 20, especially from 1 to 10 and preferably from 1 to 6 carbon atoms.

Glycoside units are known to those skilled in the art.

Insofar as sucrose is used in the glycosylation processes according to the invention, a glycoside unit according to the invention is chosen from one or more glucose(s), one or more fructose(s) or a mixture of glucose(s) and of fructose(s).

DETAILED DESCRIPTION OF THE INVENTION

The inventors have developed an enzymatic process for the glycosylation of hydroxylated synthons using specific glycan-saccharases identified by the Applicant, which are capable of performing such a glycosylation, in particular glucosylation or fructosylation.

To do this, these specific enzymes require only the presence of sucrose, which is a cheap and renewable agro-resource. In this respect, a process according to the invention is advantageously inexpensive.

These glycosylated synthons, or monomers, are advantageously used in a chemical process for preparing glyco(co) polymers of controlled structures and functionalities.

Thus, the inventors have developed a process for the chemo-enzymatic synthesis of glyco(co)polymers based on chemical polymerization or a coupling reaction of glycosylated monomers obtained enzymatically.

The processes according to the present invention advantageously make it possible to better control the degrees of glycosylation of the synthons and the structures and also their distribution.

They also make it possible to overcome the difficulties associated with sugar chemistry and to limit the use of toxic products.

They also prove to be advantageous in terms of reducing the costs and time for the production of glycosylated synthons.

Finally, these processes advantageously make it possible to gain access to a wider diversity of macromolecular architectures for various fields of application, such as biomaterials, implant materials, tissue engineering, biological diagnosis and active principle delivery.

Glycan-Saccharases of the Invention

The present invention relates firstly to a process for manufacturing a glycosylated synthon, or monomer, comprising at least one step of placing at least one glycan-saccharase of the invention in contact with at least one hydroxylated synthon according to the invention and at least one sucrose.

As indicated previously, the enzymes of the invention are advantageously capable of glycosylating synthons at their hydroxyl function.

In particular, the enzymes according to the invention are capable of glucosylating or fructosylating the synthons of the invention.

Thus, some of these enzymes consist more particularly of glycoside-hydrolases belonging to glycoside-hydrolase families 13 and 70 (GH13 and GH70).

In particular, according to a preferred embodiment, a glycan-saccharase according to the invention is chosen from the group consisting of glycoside-hydrolases belonging to glycoside-hydrolase families 13, 68 and 70 (GH13, GH68 and GH70).

The glycoside-hydrolases belonging to family 13 are amylosaccharases naturally produced by bacteria of the genera *Deinococcus, Neisseria* or *Alteromonas*.

The glycoside-hydrolases belonging to family 70 are, for their part, glucan-saccharases naturally produced by lactic acid bacteria of the genera *Leuconostoc, Lactobacillus, Streptococcus* or *Weissela* sp.

In addition, the fructosyltransferase of *Bacillus subtilis* is also used in a glycosylation process according to the invention and belongs to glycoside-hydrolase family 68.

The enzymes of the invention are all capable of transferring glucose or fructose originating from sucrose onto the hydroxylated synthons of the invention.

None of the wild-type or mutated enzymes described in the present patent application, which are known to those skilled in the art, had hitherto been used for the purpose of glucosylating hydroxylated synthons of the invention.

The nucleotide sequence of the wild-type form of the enzyme ASNp (AmyloSaccharase of *Neisseria polysaccharea*) (GH13 family) has the reference GenBank AJ011781.1 whereas its polypeptide sequence has the reference Uniprot Q9ZEU2 (SEQ ID NO: 1).

The nucleotide sequence of the wild-type form of the enzyme DSR-S (derived from the strain *Leuconostoc mesenteroides* B-512F) has the reference GenBank 109598.

The nucleotide sequence of the wild-type form of the enzyme DSR-E (derived from the strain *Leuconostoc mesenteroides* NRRL B-1299) has the reference GenBank AJ430204.1 and the reference Uniprot Q8G9Q2.

The enzyme GBD-CD2 (sequence SEQ ID NO: 13) is a truncated form of the abovementioned enzyme DSR-E, as described in Brison et al., J. Biol. Chem., 2012, 287, 7915-24.

Bibliographic references describing the wild-type and mutated enzymes according to the present invention are indicated in Table 1. In addition, the method for obtaining the mutated enzymes is described in European patent applications EP 2 100 966 and EP 2 100 965.

The peptide sequences of the various wild-type or mutated enzymes according to the invention are indicated in the present patent application.

Thus, an enzyme according to the invention may be synthesized via standard methods of synthetic chemistry, i.e. homogeneous chemical syntheses in solution or in solid phase. By way of illustration, a person skilled in the art may use the techniques of polypeptide synthesis in solution described by Houben Weil (1974, in Methoden der organischen Chemie, E, Wunsh ed., volume 15-1 and 15-II, Thieme, Stuttgart). An enzyme according to the invention may also be synthesized chemically in liquid or solid phase via successive couplings of the various amino acid residues (from the N-terminal end to the C-terminal end in liquid phase, or from the C-terminal end to the N-terminal end in solid phase). A person skilled in the art may especially use the solid-phase peptide synthesis technique described by Merrifield (Merrifield R. B., (1965a), Nature, vol. 207 (996): 522-523; Merrifield R. B., (1965b), Science, vol. 150 (693): 178-185).

According to another aspect, an enzyme according to the invention may be synthesized via genetic recombination, for example according to a production process comprising the following steps:

(a) preparing an expression vector into which has been inserted a nucleic acid coding for the peptide sequence of an enzyme of the invention, said vector also comprising the regulatory sequences required for expressing said nucleic acid in a chosen host cell;

(b) transfecting a host cell with the recombinant vector obtained in step (a);

(c) culturing the host cell transfected in step b) in a suitable culture medium;

(d) recovering the culture supernatant of the transfected cells or the cell lyzate of said cells, for example by sonication or by osmotic shock; and (e) separating or purifying, from said culture medium, or from the cell lyzate pellet, the enzyme of the invention thus obtained.

To purify an enzyme according to the invention which has been produced by host cells that have been transfected or infected with a recombinant vector coding for said enzyme, a person skilled in the art may advantageously use purification techniques described by Molinier-Frenkel (2002, J. Viral. 76, 127-135), by Karayan et al. (1994, Virology 782-795) or by Novelli et al. (1991, Virology 185, 365-376).

Thus, the glycan-saccharases that may be used in a process of the invention are chosen from a group comprising:
- a sequence having at least 80% identity with SEQ ID NO: 1 (ASNP WT);
- a sequence having at least 80% identity with SEQ ID NO: 1 mutated once at any one of the positions R226, I228, F229, A289, F290, I330, V331, D394 and R446;
- a sequence having at least 80% identity with SEQ ID NO: 11 (DSR-S vardelΔ4N-S512C);
- a sequence having at least 80% identity with SEQ ID NO: 12 (alpha-1,2 BrS);
- a sequence having at least 80% identity with SEQ ID NO: 13 ($\Delta N_{123}$-GBD-CD2);
- a sequence having at least 80% identity with SEQ ID NO: 14 (ASDg);
- a sequence having at least 80% identity with SEQ ID NO: 15 (DSR-S-OK);
- a sequence having at least 80% identity with SEQ ID NO: 16 (alpha-1,3 BrS);
- a sequence having at least 80% identity with SEQ ID NO: 17 (ASR-C-del-bis); and
- a sequence having at least 80% identity with SEQ ID NO: 18 (fructosyltransferase of *Bacillus subtilis*).

According to a particular embodiment, the mutation of a sequence having at least 80% identity with SEQ ID NO: 1 in position R226, I228, F229, A289, F290, I330, V331, D394 or R446 is a mutation by substitution.

According to one embodiment, when a sequence having at least 80% identity with SEQ ID NO: 1 is mutated once in position R226, it is chosen from a sequence having at least 80% identity with SEQ ID NO: 2 (ASNP R226$X_1$), said sequence having an amino acid $X_1$ representing an amino acid chosen from the group consisting of A, C, D, E, F, G, H, I, K, L, M, N, P, Q, S, T, V, W and Y.

According to this embodiment, $X_1$ preferably represents an amino acid chosen from the group consisting of C, H, K, M, N, Q, S, T and V.

According to one embodiment, when a sequence having at least 80% identity with SEQ ID NO: 1 is mutated once in position I228, it is chosen from a sequence having at least 80% identity with SEQ ID NO: 3 (ASNP I228$X_2$), said sequence having an amino acid $X_2$ representing an amino acid chosen from the group consisting of A, C, D, E, F, G, H, L, M, N, P, Q, R, S, T, V, W and Y.

According to this embodiment, $X_2$ preferably represents an amino acid chosen from the group consisting of H, L, T, V, W and Y.

According to one embodiment, when a sequence having at least 80% identity with SEQ ID NO: 1 is mutated once in position F229, it is chosen from a sequence having at least 80% identity with SEQ ID NO: 4 (ASNP F229$X_3$), said sequence having an amino acid $X_3$ representing an amino acid chosen from the group consisting of A, C, D, E, G, H, I, K, L, M, N, P, Q, R, S, T, V, W and Y.

According to this embodiment, $X_3$ preferably represents an amino acid chosen from the group consisting of C, D, E, G, H, I, K, M, N, P, Q, V, W and Y, in particular of C, D, E, G, I, K, M, N, P, V, W and Y, and more preferentially of M and Y.

According to one embodiment, when a sequence having at least 80% identity with SEQ ID NO: 1 is mutated once in position A289, it is chosen from a sequence having at least 80% identity with sequence SEQ ID NO: 5 (ASNP A289$X_4$), said sequence having an amino acid $X_4$ representing an amino acid chosen from the group consisting of C, D, E, F, G, H, I, K, L, M, N, P, Q, R, S, T, V, W and Y.

According to this embodiment, $X_4$ preferably represents an amino acid chosen from the group consisting of C, D, E, F, M, N P, Q, S, T, V and W, and more particularly chosen from the group consisting of F, M, N, P, Q, S and T.

According to one embodiment, when a sequence having at least 80% identity with SEQ ID NO: 1 is mutated once in position F290, it is chosen from a sequence having at least 80% identity with sequence SEQ ID NO: 6 (ASNP F290$X_5$), said sequence having an amino acid $X_5$ representing an amino acid chosen from the group consisting of A, C, D, E, G, H, I, K, L, M, N, P, Q, R, S, T, V, W and Y.

According to this embodiment, $X_5$ preferably represents an amino acid chosen from the group consisting of A, C, D, E, G, H, I, K, L, M, P, Q, S, T, V and W, more preferentially of A, C, D, H, I, K, L, M, Q, S, T, V and W, in particular of A, C, I, L, V, S, T and W.

According to one embodiment, when a sequence having at least 80% identity with SEQ ID NO: 1 is mutated once in position I330, it is chosen from a sequence having at least 80% identity with sequence SEQ ID NO: 7 (ASNP I330$X_6$), said sequence having an amino acid $X_6$ representing an amino acid chosen from the group consisting of A, C, D, E, F, G, H, K, L, M, N, P, Q, R, S, T, V, W and Y.

According to this embodiment, $X_6$ preferably represents an amino acid chosen from the group consisting of A, C, D, E, F, G, H, K, L, M, N, Q, S, V and Y, in particular of A and C, more preferentially of A.

According to one embodiment, when a sequence having at least 80% identity with SEQ ID NO: 1 is mutated once in position V331, it is chosen from a sequence having at least 80% identity with SEQ ID NO: 8 (ASNP V331$X_7$), said sequence having an amino acid $X_7$ representing an amino acid chosen from the group consisting of A, C, D, E, F, G, H, I, K, L, M, N, P, Q, R, S, T, W and Y.

According to this embodiment, $X_7$ preferably represents an amino acid chosen from the group consisting of A, C, D, E, F, G, H, I, K, L, N, Q, R, S, T, W and Y, more preferentially of C, D, E, F, G, N, R, S, T, W and Y, in particular of E, T and W;

According to one embodiment, when a sequence having at least 80% identity with SEQ ID NO: 1 is mutated once in position D394, it is chosen from a sequence having at least 80% identity with SEQ ID NO: 9 (ASNP D394$X_8$), said sequence having an amino acid $X_8$ representing an amino acid chosen from the group consisting of A, C, E, F, G, H, I, K, L, M, N, P, Q, R, S, T, V, W and Y.

According to this embodiment, $X_8$ preferably represents an amino acid chosen from the group consisting of A, E, F, G, H, I, K and L, in particular of A and E.

According to one embodiment, when a sequence having at least 80% identity with SEQ ID NO: 1 is mutated once in position R446, it is chosen from a sequence having at least 80% identity with SEQ ID NO: 10 (ASNP R446$X_9$), said sequence having an amino acid $X_9$ representing an amino acid chosen from the group consisting of A, C, D, E, F, G, H, I, K, L, M, N, Q, S, T, V, W and Y.

According to this embodiment, $X_9$ preferably represents an amino acid chosen from the group consisting of A, C, G, K, L, M, N, and S, in particular of A, N and M.

According to one embodiment, a sequence having at least 80% identity with SEQ ID NO: 1 mutated once at any one of the positions R226, I228, F229, A289, F290, I330, V331, D394 and R446 is chosen from any one of the sequences SEQ ID NO: 2 to 10 defined above.

According to a particular embodiment, a sequence having at least 80% identity with SEQ ID NO: 1 mutated once at any one of the positions R226, I228, F229, A289, F290, I330, V331, D394 and R446 is chosen from:
- a sequence having at least 80% identity with SEQ ID NO: 2 (ASNP R226$X_1$), said sequence having an amino acid $X_1$ representing an amino acid chosen from the group consisting of A, C, D, E, F, G, H, I, K, L, M, N, P, Q, S, T, V, W and Y.
- a sequence having at least 80% identity with SEQ ID NO: 3 (ASNP I228$X_2$), said sequence having an amino acid $X_2$ representing an amino acid chosen from the group consisting of A, C, D, E, F, G, H, L, M, N, P, Q, R, S, T, V, W and Y;
- a sequence having at least 80% identity with SEQ ID NO: 4 (ASNP F229$X_3$), said sequence having an amino acid $X_3$ representing an amino acid chosen from the group consisting of A, C, D, E, G, H, I, K, L, M, N, P, Q, R, S, T, V, W and Y;
- a sequence having at least 80% identity with the sequence SEQ ID NO: 5 (ASNP A289$X_4$), said sequence having an amino acid $X_4$ representing an amino acid chosen from the group consisting of C, D, E, F, G, H, I, K, L, M, N, P, Q, R, S, T, V, W and Y;
- a sequence having at least 80% identity with the sequence SEQ ID NO: 6 (ASNP F290$X_5$), said sequence having an amino acid $X_5$ representing an amino acid chosen from the group consisting of A, C, D, E, G, H, I, K, L, M, N, P, Q, R, S, T, V, W and Y;
- a sequence having at least 80% identity with the sequence SEQ ID NO: 7 (ASNP I330$X_6$), said sequence having an amino acid $X_6$ representing an amino acid chosen from the group consisting of A, C, D, E, F, G, H, K, L, M, N, P, Q, R, S, T, V, W and Y;
- a sequence having at least 80% identity with SEQ ID NO: 8 (ASNP V331$X_7$), said sequence having an amino acid $X_7$ representing an amino acid chosen from the group consisting of A, C, D, E, F, G, H, I, K, L, M, N, P, Q, R, S, T, W and Y;
- a sequence having at least 80% identity with SEQ ID NO: 9 (ASNP D394$X_8$), said sequence having an amino acid $X_8$ representing an amino acid chosen from the group consisting of A, C, E, F, G, H, I, K, L, M, N, P, Q, R, S, T, V, W and Y; and
- a sequence having at least 80% identity with SEQ ID NO: 10 (ASNP R446$X_9$), said sequence having an amino acid $X_9$ representing an amino acid chosen from the group consisting of A, C, D, E, F, G, H, I, K, L, M, N, Q, S, T, V, W and Y.

According to a particular embodiment, a sequence having at least 80% identity with SEQ ID NO: 1 mutated once at any one of the positions R226, I228, F229, A289, F290, I330, V331, D394 and R446 is chosen from:
- a sequence having at least 80% identity with SEQ ID NO: 2 (ASNP R226$X_1$), said sequence having an amino acid $X_1$ representing an amino acid chosen from the group consisting of C, H, K, M, N, Q, S, T and V;
- a sequence having at least 80% identity with SEQ ID NO: 3 (ASNP I228$X_2$), said sequence having an amino acid $X_2$ representing an amino acid chosen from the group consisting of H, L, T, V, W and Y;
- a sequence having at least 80% identity with SEQ ID NO: 4 (ASNP F229$X_3$), said sequence having an amino acid $X_3$ representing an amino acid chosen from the group consisting of C, D, E, G, H, I, K, M, N, P, Q, V, W and Y, in particular of C, D, E, G, I, K, M, N, P, V, W and Y, and more preferentially of M and Y;
- a sequence having at least 80% identity with the sequence SEQ ID NO: 5 (ASNP A289$X_4$), said sequence having an amino acid $X_4$ representing an amino acid chosen from the group consisting of C, D, E, F, M, N, P, Q, S, T, V and W, and more particularly chosen from the group consisting of F, M, N, P, Q, S and T;
- a sequence having at least 80% identity with the sequence SEQ ID NO: 6 (ASNP F290$X_5$), said sequence having an amino acid $X_5$ representing an amino acid chosen from the group consisting of A, C, D, E, G, H, I, K, L, M, P, Q, S, T, V and W, more preferentially of A, C, D, H, I, K, L, M, Q, S, T, V and W, in particular of A, C, I, L, V, S, T and W;
- a sequence having at least 80% identity with the sequence SEQ ID NO: 7 (ASNP I330$X_6$), said sequence having an amino acid $X_6$ representing an amino acid chosen from the group consisting of A, C, D, E, F, G, H, K, L, M, N, Q, S, V and Y, in particular of A and C, more preferentially of A;
- a sequence having at least 80% identity with SEQ ID NO: 8 (ASNP V331$X_7$), said sequence having an amino acid $X_7$ representing an amino acid chosen from the group consisting of A, C, D, E, F, G, H, I, K, L, N, Q, R, S, T, W and Y, more preferentially of C, D, E, G, F, N, R, S, T, W and Y, in particular of E, T and W;
- a sequence having at least 80% identity with SEQ ID NO: 9 (ASNP D394$X_8$), said sequence having an amino acid $X_8$ representing an amino acid chosen from the group consisting of A, E, F, G, H, I, K and L, in particular of A and E;
- a sequence having at least 80% identity with SEQ ID NO: 10 (ASNP R446$X_9$), said sequence having an amino acid $X_9$ representing an amino acid chosen from the group consisting of A, C, G, K, L, M, N, and S, in particular of A As shown in the examples, all the enzymes bearing one of these peptide sequences have a statistically higher, or even very much higher, capacity than that of the wild-type enzyme for glucosylating the hydroxylated synthons of the invention.

In addition, it may be advantageous to use some of the wild-type and/or mutant enzymes according to the invention according to the nature of the hydroxylated synthon used in a process of the invention.

Thus, in the case where the hydroxylated synthon used in a process of the invention is HEMA, certain enzymes may advantageously obtain only mono-glucosylated HEMAs, for instance an enzyme containing a sequence having at least 80% identity with SEQ ID NO: 13 ($\Delta N_{123}$-GBD-CD2).

Furthermore, in the case where the hydroxylated synthon used in a process of the invention is HEMA, certain enzymes advantageously make it possible to obtain only mono-glucosylated HEMAs and di-glucosylated HEMAs, for instance the enzymes chosen from the group:
  a sequence having at least 80% identity with SEQ ID NO: 4 (ASNP F229$X_3$), said sequence having an amino acid $X_3$ representing W;
  a sequence having at least 80% identity with the sequence SEQ ID NO: 7 (ASNP I330$X_6$), said sequence having an amino acid $X_6$ representing A;
  a sequence having at least 80% identity with SEQ ID NO: 8 (ASNP V331$X_7$), said sequence having an amino acid $X_7$ representing E;
  a sequence having at least 80% identity with SEQ ID NO: 9 (ASNP D394$X_8$), said sequence having an amino acid $X_8$ representing A;
  a sequence having at least 80% identity with SEQ ID NO: 14 (ASDg);
  a sequence having at least 80% identity with SEQ ID NO: 12 (alpha-1,2 BrS); and
  a sequence having at least 80% identity with SEQ ID NO: 16 (alpha-1,3 BrS).

Finally, in the case where the hydroxylated synthon used in a process of the invention is HEMA, certain enzymes advantageously make it possible to obtain a mixture of mono-glucosylated, di-glucosylated and tri-glucosylated HEMA, for instance the enzymes chosen from the group:
  a sequence having at least 80% identity with SEQ ID NO: 1 (ASNP WT),
  a sequence having at least 80% identity with the sequence SEQ ID NO: 6 (ASNP F290$X_5$), said sequence having an amino acid $X_5$ representing an amino acid chosen from the group consisting of A, C, I, K, L, M and V;
  a sequence having at least 80% identity with SEQ ID NO: 10 (ASNP R446$X_9$), said sequence having an amino acid $X_9$ representing G; and
  a sequence having at least 80% identity with SEQ ID NO: 17 (ASR-C-del-bis).

In particular, the enzymes chosen from the group:
  a sequence having at least 80% identity with the sequence SEQ ID NO: 6 (ASNP F290$X_5$), said sequence having an amino acid $X_5$ representing A; and
  a sequence having at least 80% identity with SEQ ID NO: 17 (ASR-C-del-bis);
advantageously make it possible to obtain a very similar proportion of mono-glucosylated HEMAs and of tri-glucosylated HEMAs.

Similarly, in the case where the hydroxylated synthon used in a process of the invention is NHAM, certain enzymes advantageously make it possible to obtain only mono-glucosylated NHAMs, for instance the enzymes chosen from the group:
  a sequence having at least 80% identity with SEQ ID NO: 14 (ASDg);
  a sequence having at least 80% identity with SEQ ID NO: 11 (DSR-S vardel$\Delta$4N-S512C); and
  a sequence having at least 80% identity with SEQ ID NO: 15 (DSR-S-OK).

Furthermore, in the case where the hydroxylated synthon used in a process of the invention is NHAM, certain enzymes advantageously make it possible to obtain only mono-glucosylated NHAMs and di-glucosylated NHAMs, for instance the enzymes chosen from the group:
  a sequence having at least 80% identity with SEQ ID NO: 1 (ASNP WT),
  a sequence having at least 80% identity with SEQ ID NO: 4 (ASNP F229$X_3$), said sequence having an amino acid $X_3$ representing N;
  a sequence having at least 80% identity with the sequence SEQ ID NO: 5 (ASNP A289$X_4$), said sequence having an amino acid $X_4$ representing an amino acid chosen from the group consisting of N, P and Q;
  a sequence having at least 80% identity with the sequence SEQ ID NO: 7 (ASNP I330$X_6$), said sequence having an amino acid $X_6$ representing N;
  a sequence having at least 80% identity with SEQ ID NO: 8 (ASNP V331$X_7$), said sequence having an amino acid $X_7$ representing T;
  a sequence having at least 80% identity with SEQ ID NO: 9 (ASNP D394$X_8$), said sequence having an amino acid $X_8$ representing E;
  a sequence having at least 80% identity with SEQ ID NO: 17 (ASR-C-del-bis);
  a sequence having at least 80% identity with SEQ ID NO: 13 ($\Delta N_{123}$-GBD-CD2); and
  a sequence having at least 80% identity with SEQ ID NO: 16 (alpha-1,3 BrS).

Finally, in the case where the hydroxylated synthon used in a process of the invention is NHAM, certain enzymes advantageously make it possible to obtain a mixture of mono-glucosylated, di-glucosylated and tri-glucosylated NHAMs, for instance the enzymes chosen from the group:
  a sequence having at least 80% identity with SEQ ID NO: 4 (ASNP F229$X_3$), said sequence having an amino acid $X_3$ representing M;
  a sequence having at least 80% identity with SEQ ID NO: 8 (ASNP V331$X_7$), said sequence having an amino acid $X_7$ representing an amino acid chosen from the group consisting of C, D and E; and
  a sequence having at least 80% identity with SEQ ID NO: 12 (alpha-1,2 BrS).

In addition, in the case where the hydroxylated synthon used in a process of the invention is NNHEA, certain enzymes advantageously make it possible to obtain only mono-glucosylated NNHEAs, for instance the enzymes chosen from the group:
  a sequence having at least 80% identity with SEQ ID NO: 17 (ASR-C-del-bis); and
  a sequence having at least 80% identity with SEQ ID NO: 16 (alpha-1,3 BrS).

When the hydroxylated synthon used in a process of the invention is NNHEA, other enzymes also make it possible advantageously to obtain only mono-glucosylated NNHEAs, namely:
  a sequence having at least 80% identity with SEQ ID NO: 1 (ASNP WT),
  a sequence having at least 80% identity with the sequence SEQ ID NO: 5 (ASNP A289$X_4$), said sequence having an amino acid $X_4$ representing Q;

a sequence having at least 80% identity with the sequence SEQ ID NO: 6 (ASNP F290X$_5$), said sequence having an amino acid X$_5$ representing an amino acid chosen from the group consisting of representing C, L and V; and a sequence having at least 80% identity with SEQ ID NO: 12 (alpha-1,2 BrS).

It should be understood from these formulations that the amino acids defined as being, respectively, X$_1$, X$_2$, X$_3$, X$_4$, X$_5$, X$_6$, X$_7$, X$_8$ and X$_9$ are present and as defined above in the glucan-saccharases of the invention having at least 80% identity with the sequence SEQ ID NO: 1.

The present invention also includes the sequences whose amino acid sequence has at least 80%, 81%, 82%, 83%, 84%, 85%, 86%, 87%, 88%, 89%, 90%, 91%, 92%, 93%, 94%, 95%, 96%, 97%, 98%, 99% or 100% amino acid identity with one of the sequences SEQ ID NO: 1 to 18 as defined previously and biological activity of the same nature.

The term "biological activity of the same nature" as regards the peptide sequences 1 to 18 means the same capacity for glycosylating the hydroxylated synthons of the invention.

The "percentage of identity" between two nucleic acid or amino acid sequences, for the purposes of the present invention, is determined by comparing the two optimally aligned sequences, through a comparison window.

The part of the nucleotide sequence in the comparison window may thus comprise additions or deletions (for example "gaps") relative to the reference sequence (which does not comprise these additions or these deletions) so as to obtain an optimal alignment between the two sequences.

The percentage of identity is calculated by determining the number of positions in which an identical nucleic base (or an identical amino acid) is observed for the two compared sequences, and then by dividing the number of positions in which there is identity between the two nucleic bases (or between the two amino acids) by the total number of positions in the comparison window, followed by multiplying the result by 100 so as to obtain the percentage of nucleotide (or amino acid) identity between the two sequences.

Optimal alignment of the sequences for the comparison may be achieved by computer-assisted means using known algorithms.

In an entirely preferred manner, the percentage of sequence identity is determined using the software CLUSTAL W (version 1.82), the parameters being set as follows: (1) CPU MODE=ClustalW mp; (2) ALIGNMENT=«full»; (3) OUTPUT FORMAT=«aln w/numbers»; (4) OUTPUT ORDER=«aligned»; (5) COLOR ALIGNMENT=«no»; (6) KTUP (word size)=«default»; (7) WINDOW LENGTH=«default»; (8) SCORE TYPE=«percent»; (9) TOPDIAG=«default»; (10) PAIRGAP=«default»; (11) PHYLOGENETIC TREE/TREE TYPE=«none»; (12) MATRIX=«default»; (13) GAP OPEN=«default»; (14) END GAPS=«default»; (15) GAP EXTENSION=«default»; (16) GAP DISTANCES=«default»; (17) TREE TYPE=«cladogram» and (18) TREE GRAP DISTANCES=«hide».

More particularly, the present invention also relates to sequences whose amino acid sequence has 100% amino acid identity with amino acids 225 to 450 of sequences SEQ ID NO: 2 to 10 and at least 80%, 81%, 82%, 83%, 84%, 85%, 86%, 87%, 88%, 89%, 90%, 91%, 92%, 93%, 94%, 95%, 96%, 97%, 98%, 99% or 100% amino acid identity with the rest of the sequences SEQ ID NO: 2 to 10 as defined previously, and biological activity of the same nature.

The enzymes according to the invention make it possible to produce glycosylated synthons, or monomers, which may be mono- or poly-glycosylated.

Thus, as illustrated in the examples of the present patent application, the specificities of the various enzymes of the invention advantageously make it possible to tailor-make monomers of given structure.

By way of example, and as illustrated in the examples, and in particular in Table 3, when HEMA is glucosylated using the enzyme GBD-CD2, all of the monomers obtained are mono-glucosylated. In contrast, the use of the enzyme ASR in the presence of HEMA makes it possible to obtain a homogeneous distribution of mono-, di- and tri-glucosylated HEMA.

Hydroxylated Synthons and Implementations a) Hydroxylated Synthons Used in an Enzymatic Glycosylation Process of the Invention The hydroxylated synthons specifically used in an enzymatic process for manufacturing monomers of the invention are chosen from the compounds of formulae (I) to (VI).

Thus, according to a first aspect, the hydroxylated synthons of the invention may be compounds of formula (I):

(i) (Meth)Acrylate/(Meth)Acrylamide Synthons of Formula (I):

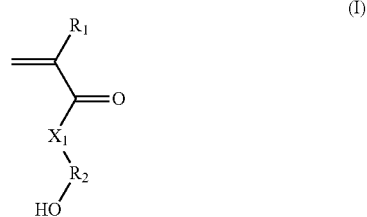

(I)

in which:
R$_1$ represents a hydrogen atom or a C$_1$-C$_3$ alkyl;
R$_2$ represents a C$_1$-C$_{20}$ alkylene group; or a group (C$_2$H$_4$O)$_n$, with n being an integer between 1 and 10; and
X$_1$ represents —(O)—, —(NH)—, —(S)— or —(NR'$_2$(OH))—, preferably —(O)—, —(NH)—, or —(NR'$_2$(OH))—, with R'$_2$ representing a C$_1$-C$_{20}$ alkylene group; or a group —(C$_2$H$_4$O)$_m$—, with m being an integer between 1 and 10.

According to one embodiment, R$_1$ represents a hydrogen atom.

According to another embodiment, R$_1$ represents a C$_1$-C$_3$ alkyl, preferably a methyl.

According to one embodiment, R$_2$ represents a C$_1$-C$_{20}$, in particular C$_1$-C$_{10}$ and especially C$_1$ to C$_5$ alkylene group. More particularly, R$_2$ may be chosen from the group consisting of a methylene, an ethylene, a propylene, a butylene and a pentylene, and preferably represents a methylene or an ethylene.

According to one embodiment, X$_1$ represents —(O)—, —(NH)— or —(NR'$_2$(OH))—, preferably —(O)— or —(NH)—.

According to one embodiment, R'$_2$ represents a C$_1$-C$_{20}$, in particular C$_1$-C$_{10}$ and especially C$_1$ to C$_5$ alkylene group. More particularly, R'$_2$ may be chosen from the group consisting of a methylene, an ethylene, a propylene, a butylene and a pentylene, and preferably represents a methylene or an ethylene.

According to a particular embodiment, a synthon of formula (I) of the invention is such that:

$R_1$ represents a hydrogen atom or a $C_1$-$C_3$ alkyl, preferably a hydrogen or a methyl;

$R_2$ represents a $C_1$-$C_{20}$ alkyl group, preferably a $C_1$-$C_{10}$ and in particular $C_1$-$C_5$ alkylene, more particularly a methylene or an ethylene; and $X_1$ represents —(O)—, —(NH)— or —(NR'$_2$(OH))—, preferably —(O)— or —(NH)—.

According to a preferred embodiment, a synthon of formula (I) of the invention is such that:

$X_1$ represents —(O)—;

$R_1$ represents a hydrogen atom or a $C_1$-$C_3$ alkyl, preferably a $C_1$-$C_3$ alkyl, in particular a methyl; and $R_2$ represents a $C_1$-$C_{20}$ alkyl group, preferably a $C_1$-$C_{10}$ and in particular $C_1$-$C_5$ alkylene, more particularly a methylene or an ethylene, preferentially an ethylene.

Such a synthon of formula (I) may in particular be a 2-(hydroxy)ethyl methacrylate (HEMA):

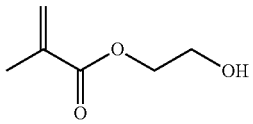

According to another preferred embodiment, a synthon of formula (I) of the invention is such that:

$X_1$ represents —(NH)—;

$R_1$ represents a hydrogen atom or a $C_1$-$C_3$ alkyl, preferably a hydrogen or a methyl; and $R_2$ represents a $C_1$-$C_{20}$ alkyl group, preferably a $C_1$-$C_{10}$ (and in particular $C_1$-$C_5$ alkylene, more particularly a methylene or an ethylene.

Such a synthon of formula (I) may in particular be an N-(hydroxy)methylacrylamide (NHAM) or an N-(hydroxy)ethylacrylamide (HEAA):

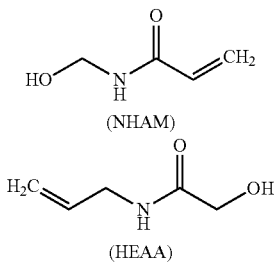

According to another preferred embodiment, a synthon of formula (I) of the invention is such that:

$X_1$ represents —(NR'$_2$(OH))—, in which R'$_2$ represents a $C_1$-$C_{20}$, in particular $C_1$-$C_{10}$ and especially $C_1$ to $C_5$ alkylene group, more particularly a methylene, an ethylene, a propylene, a butylene or a pentylene, preferably a methylene or an ethylene, plus preferentially an ethylene;

$R_1$ represents a hydrogen atom; and $R_2$ represents a $C_1$-$C_{20}$ alkyl group, preferably a $C_1$-$C_{10}$ and in particular $C_1$-$C_5$ alkylene, more particularly a methylene or an ethylene, especially an ethylene.

Such a synthon of formula (I) may in particular be an N,N-bis(2-hydroxyethyl)acrylamide (NNHEA):

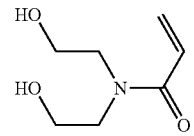

According to a particular embodiment, a synthon of the invention of formula (I) is chosen from 2-(hydroxy)ethyl methacrylate (HEMA), N-(hydroxy)methylacrylamide (NHAM), N-(hydroxy)ethylacrylamide (HEAA) and N,N-bis(2-hydroxyethyl)acrylamide (NNHEA), preferably from HEMA, NHAM and HEAA.

According to another aspect, the hydroxylated synthons of the invention may be compounds of formula (II):

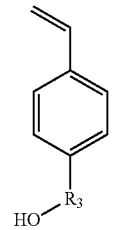

in which $R_3$ represents a covalent bond; a $C_1$-$C_{20}$ alkylene group; or a group $(C_2H_4O)_n$, with n being an integer between 1 and 10.

Preferably, $R_3$ represents a covalent bond or a $C_1$-$C_{20}$ alkylene group.

Such an alkylene group may in particular be of $C_1$-$C_{10}$, especially $C_1$-$C_5$. More particularly, $R_3$ may be chosen from the group consisting of a methylene, an ethylene, a propylene, a butylene and a pentylene, and is preferably a methylene or an ethylene.

Thus, according to a particular embodiment, $R_3$ represents a covalent bond, a methylene or an ethylene.

A synthon of formula (II) may in particular be a 4-vinylphenol (VP) or a 4-vinylbenzyl alcohol (VBA):

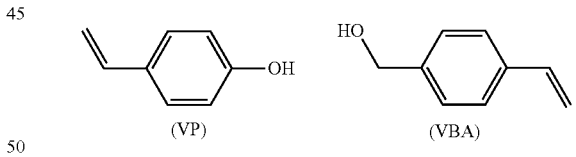

According to another aspect, the hydroxylated synthons of the invention may be compounds of formula (III):

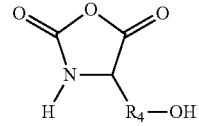

in which $R_4$ represents a covalent bond; a $C_1$-$C_{20}$ alkylene group; or a group $(C_2H_4O)_n$, with n being an integer between 1 and 10.

Preferably, $R_4$ represents a $C_1$-$C_{20}$, in particular $C_1$-$C_{10}$ and especially $C_1$-$C_5$ alkylene group. More particularly, $R_4$ may be chosen from the group consisting of a methylene, an ethylene, a propylene, a butylene and a pentylene, and is preferably a methylene or an ethylene, more particularly a methylene.

A synthon of formula (III) may in particular be a 4-(hydroxy)methyloxazolidine-2,5-dione (HMNCA):

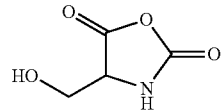

According to another aspect, the hydroxylated synthons of the invention may be compounds of formula (IV):

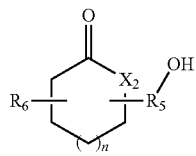

(IV)

in which:

$R_5$ represents a covalent bond; a $C_1$-$C_{20}$ alkylene group; or a group $(C_2H_4O)_m$, with m being an integer between 1 and 10;

n represents an integer between 1 and 20;

$X_2$ represents —(O)—, —(NH)— or —(S)—; and $R_6$ represents a hydrogen or a $C_1$-$C_{20}$ alkyl group.

According to a preferred embodiment, $X_2$ represents —(O)—.

According to one embodiment, n is between 1 and 10, especially between 1 and 5. n is in particular chosen from 1, 2, 3, 4 and 5, and preferably represents the value 1 or 2.

Preferably, $R_5$ represents a covalent bond or a $C_1$-$C_{10}$ and especially $C_1$-$C_5$ alkylene group. More particularly, the alkylene group may be chosen from the group consisting of a methylene, an ethylene, a propylene, a butylene and a pentylene, preferably a methylene or an ethylene, more particularly a methylene.

Thus, in a particularly preferred manner, $R_5$ represents a covalent bond or a methylene.

According to one embodiment, $R_6$ represents a hydrogen or a $C_1$-$C_{10}$ and especially $C_1$-$C_5$ alkyl group. More particularly, the alkyl group may be chosen from the group consisting of a methyl, an ethyl, a propyl, a butyl and a pentyl, preferably a methyl or an ethyl, more particularly a methyl.

Thus, in a particularly preferred manner, $R_6$ represents a hydrogen or a methyl.

According to a particular embodiment, a compound of formula (IV) is such that:

$R_5$ represents a $C_1$-$C_{10}$ and especially $C_1$-$C_5$ alkylene group, and is in particular a methylene;

n represents an integer between 1 and 5; and preferably represents the value 1 or 2, in particular the value 2;

$X_2$ represents —(O)—; and $R_6$ represents a hydrogen.

Such a synthon of formula (IV) may in particular be an α-(hydroxy)methylcaprolactone (AHMCL):

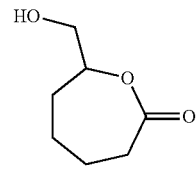

According to another particular embodiment, a compound of formula (IV) is such that:

$R_5$ represents a covalent bond;

n represents an integer between 1 and 5; and preferably represents the value 1 or 2, in particular the value 1;

$X_2$ represents —(O)—; and $R_6$ represents a $C_1$-$C_{10}$ and especially $C_1$-$C_5$ alkyl group and is in particular a methyl.

Such a synthon of formula (IV) may in particular be a (±)-mevalonolactone (MVL):

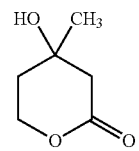

According to a particular embodiment, a synthon of the invention of formula (IV) is chosen from α-(hydroxy)methylcaprolactone (AHMCL) and (±)-mevalonolactone (MVL).

According to another aspect, the hydroxylated synthons of the invention may be compounds of formula (V):

(V)

in which $R_7$ represents a $C_1$-$C_{20}$ alkylene group.

Preferably, $R_7$ represents a $C_1$-$C_{10}$ and especially $C_1$-$C_5$ alkylene group. More particularly, $R_7$ may be chosen from the group consisting of a methylene, an ethylene, a propylene, a butylene and a pentylene, preferably a methylene or an ethylene, more particularly an ethylene.

Such a synthon of formula (V) may in particular be a 2-mercaptoethanol (BME):

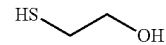

According to another aspect, the hydroxylated synthons of the invention may be compounds of formula (VI):

(VI)

in which $R_8$ represents a $C_1$-$C_{20}$ alkylene group.

Preferably, $R_8$ represents a $C_1$-$C_{10}$ and especially $C_1$-$C_5$ alkylene group. More particularly, $R_8$ may be chosen from the group consisting of a methylene, an ethylene, a propylene, a butylene and a pentylene, preferably a methylene or an ethylene, more particularly a methylene.

Such a synthon of formula (VI) may in particular be a 2-propen-1-ol (allyl alcohol):

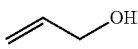

According to one embodiment, a synthon of the invention may be chosen from the group consisting of 2-(hydroxy) ethyl methacrylate (HEMA), N-(hydroxy)methylacrylamide (NHAM), N-(hydroxy)ethylacrylamide (HEAA), 4-vinylphenol (VP), 4-vinylbenzyl alcohol (VBA), 4-(hydroxy) methyloxazolidine-2,5-dione (HMNCA), α-(hydroxy)methylcaprolactone (AHMCL), (±)-mevalonolactone (MVL), 2-mercaptoethanol (BME), 2-propen-1-ol (allyl alcohol) and N,N-bis(2-hydroxyethyl)acrylamide (NNHEA).

A synthon according to the invention is in particular chosen from the group consisting of 2-(hydroxy)ethyl methacrylate (HEMA), N-(hydroxy)methylacrylamide (NHAM), N-(hydroxy)ethylacrylamide (HEAA), 4-vinylbenzyl alcohol (VBA), 2-propen-1-ol (allyl alcohol) and 2-mercaptoethanol (BME).

b) Glycosylated Synthons or Monomers

The enzymatic glycosylation of hydroxylated synthons, and in particular mono-hydroxylated synthons, of the invention is performed in the presence of sucrose.

In the present patent application, the terms "glycosylated synthons" and "monomers" are used interchangeably to denote the glycosylated synthons obtained on conclusion of the enzymatic process according to the invention for the glycosylation of hydroxylated synthons.

Thus, the synthons of the invention are more particularly glycosylated or fructosylated during the enzymatic glycosylation process according to the invention.

The process according to the invention for the manufacture of a glycosylated synthon, or monomer, of the invention may especially be performed under the conditions listed in example 1, point 1.3 below.

The monomers of the invention may be mono- or polyglycosylated, as illustrated in the examples of the present patent application.

On conclusion of this glycosylation of the synthons of the invention, the enzyme may advantageously be inactivated. By way of illustration, this inactivation may be performed by thermal inactivation, for example at a temperature above 60° C., especially above 80° C., preferably above 90° C.

According to a particular embodiment, the reaction medium containing the glycosylated synthons according to the invention is concentrated by lyophilization, especially in anticipation of a subsequent purification step.

According to another embodiment, the reaction medium containing the glycosylated synthons according to the invention is not concentrated by lyophilization.

According to one embodiment, the glycosylated synthons according to the invention are purified after their preparation. This purification step, when it is performed, may take place after a step of inactivating the enzyme used and/or after a lyophilization step. Preferably, such a purification step takes place after a step of inactivating the enzyme, in the absence of a lyophilization step.

This purification step may advantageously also comprise a step of liquid/liquid extraction so as to remove the residual synthon.

PREFERRED EMBODIMENTS

In the case where the hydroxylated synthon used in the process of the invention is HEMA, the glycan-saccharase used may advantageously be chosen from the group comprising:

a sequence having at least 80% identity with SEQ ID NO: 1 (ASNP WT), a sequence having at least 80% identity with SEQ ID NO: 2 (ASNP R226$X_1$), said sequence having an amino acid $X_1$ representing an amino acid chosen from the group consisting of A, C, N, P, S and T, preferably C;

a sequence having at least 80% identity with SEQ ID NO: 3 (ASNP I228$X_2$), said sequence having an amino acid $X_2$ representing an amino acid chosen from the group consisting of P, T and V, preferably T;

a sequence having at least 80% identity with SEQ ID NO: 4 (ASNP F229$X_3$), said sequence having an amino acid $X_3$ representing W;

a sequence having at least 80% identity with the sequence SEQ ID NO: 5 (ASNP A289$X_4$), said sequence having an amino acid $X_4$ representing H, I, K, L, M and W, preferably H and L;

a sequence having at least 80% identity with the sequence SEQ ID NO: 6 (ASNP F290$X_5$), said sequence having an amino acid $X_5$ representing an amino acid chosen from the group consisting of A, C, H, I, K, L, M, N, P, Q, V and W, preferably A, C, I, K, L, M, P and V, in particular A, C, I, K, L, M and V, and especially A, C, I, L and V;

a sequence having at least 80% identity with the sequence SEQ ID NO: 7 (ASNP I330$X_6$), said sequence having an amino acid $X_6$ representing A, C, E, F, G, H, K, L, M and N, preferably A;

a sequence having at least 80% identity with SEQ ID NO: 8 (ASNP V331$X_7$), said sequence having an amino acid $X_7$ representing an amino acid chosen from the group consisting of A, C, D, E, F, G, H, K, L, M, in particular C, D, E, G, H, and especially E;

a sequence having at least 80% identity with SEQ ID NO: 9 (ASNP D394$X_8$), said sequence having an amino acid $X_8$ representing A, C, E, G, H, I, L, M and N, in particular A;

a sequence having at least 80% identity with SEQ ID NO: 10 (ASNP R446$X_9$), said sequence having an amino acid $X_9$ representing an amino acid chosen from the group consisting of A, C, D, E, F, G, H, I, K, L, M and N, preferably C, G, K, L and N, especially N;

a sequence having at least 80% identity with SEQ ID NO: 12 (alpha-1,2 BrS);

a sequence having at least 80% identity with SEQ ID NO: 13 ($\Delta N_{123}$-GBD-CD2);

a sequence having at least 80% identity with SEQ ID NO: 14 (ASDg);

a sequence having at least 80% identity with SEQ ID NO: 16 (alpha-1,3 BrS);

a sequence having at least 80% identity with SEQ ID NO: 17 (ASR-C-del-bis); and a sequence having at least 80% identity with SEQ ID NO: 18 (fructosyltransferase of *Bacillus subtilis*).

In addition, in the case where the hydroxylated synthon used is NHAM, the glycan-saccharase used in a process of the invention may be chosen from the group comprising:

a sequence having at least 80% identity with SEQ ID NO: 1 (ASNP WT), a sequence having at least 80% identity with SEQ ID NO: 2 (ASNP R226$X_1$), said sequence having an amino acid $X_1$ representing an amino acid chosen from the group consisting of A, C, D, E, F, G, H, I, K, L, M, N, Q, S, T, V, W and Y;

a sequence having at least 80% identity with SEQ ID NO: 3 (ASNP I228$X_2$), said sequence having an amino acid X₂ representing an amino acid chosen from the group consisting of C, E, L, M, N, P, Q, R, T, V and Y;

a sequence having at least 80% identity with SEQ ID NO: 4 (ASNP F229X₃), said sequence having an amino acid X₃ representing an amino acid chosen from the group consisting of A, C, I, L, M, N, P, Q, V, W and Y, preferably M;

a sequence having at least 80% identity with the sequence SEQ ID NO: 5 (ASNP A289X₄), said sequence having an amino acid X₄ representing an amino acid chosen from the group consisting of C, D, E, F, G, H, I, L, M, N, P, Q, S, T and V, preferably N, P, Q, S, and V, especially N, P and Q;

a sequence having at least 80% identity with the sequence SEQ ID NO: 6 (ASNP F290X₅), said sequence having an amino acid X₅ representing an amino acid chosen from the group consisting of A, C, G, L, M, N, P, Q, V, W and Y;

a sequence having at least 80% identity with the sequence SEQ ID NO: 7 (ASNP I330X₆), said sequence having an amino acid X₆ representing an amino acid chosen from the group consisting of A, M, N and V, preferably N;

a sequence having at least 80% identity with SEQ ID NO: 8 (ASNP V331X₇), said sequence having an amino acid X₇ representing an amino acid chosen from the group consisting of A, C, D, E, F, G, H, I, L, M, N, P, Q, R, S, T and Y, preferably C, D, E, N, and T, especially E;

a sequence having at least 80% identity with SEQ ID NO: 9 (ASNP D394X₈), said sequence having an amino acid X₈ representing an amino acid chosen from the group consisting of C, E, G and N, preferably E;

a sequence having at least 80% identity with SEQ ID NO: 10 (ASNP R446X₉), said sequence having an amino acid X₉ representing an amino acid chosen from the group consisting of A, C, F, G, K, L, M, N, Q, S, T and Y;

a sequence having at least 80% identity with SEQ ID NO: 11 (DSR-S vardelΔ4N-S512C);

a sequence having at least 80% identity with SEQ ID NO: 12 (alpha-1,2 BrS);

a sequence having at least 80% identity with SEQ ID NO: 13 (ΔN₁₂₃-GBD-CD2);

a sequence having at least 80% identity with SEQ ID NO: 14 (ASDg);

a sequence having at least 80% identity with SEQ ID NO: 15 (DSR-S-OK);

a sequence having at least 80% identity with SEQ ID NO: 16 (alpha-1,3 BrS);

a sequence having at least 80% identity with SEQ ID NO: 17 (ASR-C-del-bis); and a sequence having at least 80% identity with SEQ ID NO: 18 (fructosyltransferase of *Bacillus subtilis*).

According to a particular embodiment, a process for manufacturing a glycosylated synthon, or monomer, comprises at least one step of placing at least one glycan-saccharase in contact with at least 2-mercaptoethanol (BME) as hydroxylated synthon and at least one sucrose, in which the glycan-saccharase is chosen from the group comprising:

a sequence having at least 80% identity with SEQ ID NO: 1 (ASNP WT);

a sequence having at least 80% identity with SEQ ID NO: 3 (ASNP I228X₂), said sequence having an amino acid X₂ representing an amino acid chosen from the group consisting of A, E, F, H, L, M, N, Q, R, V, W and Y, preferably L, V, W and Y;

a sequence having at least 80% identity with SEQ ID NO: 4 (ASNP F229X₃), said sequence having an amino acid X₃ representing an amino acid chosen from the group consisting of A, C, I, L, M, P, Q, R, V, W and Y, preferably C, M, P, Q, V, W and Y, in particular C, M, P, V and Y, especially Y;

a sequence having at least 80% identity with the sequence SEQ ID NO: 5 (ASNP A289X₄), said sequence having an amino acid X₄ representing an amino acid chosen from the group consisting of C, D, E, F, G, H, I, M, N, P, Q, R, S, T, V and W, preferably C, D, E, F, M, N, P, Q, S, T, V and W, and especially F, M, N, P, Q, S and T;

a sequence having at least 80% identity with the sequence SEQ ID NO: 6 (ASNP F290X₅), said sequence having an amino acid X₅ representing an amino acid chosen from the group consisting of A, C, D, E, G, H, I, K, L, M, P, Q, R, S, T, V, W and Y, preferably A, C, D, E, G, I, M, P, Q, S, T, V and W, in particular D, Q, S, T and W, and especially S, T and W;

a sequence having at least 80% identity with the sequence SEQ ID NO: 7 (ASNP I330X₆), said sequence having an amino acid X₆ representing an amino acid chosen from the group consisting of A, N, Q, S, T, V and W, preferably Q and V;

a sequence having at least 80% identity with SEQ ID NO: 8 (ASNP V331X₇), said sequence having an amino acid X₇ representing an amino acid chosen from the group consisting of A, C, D, E, F, G, H, I, K, L, N, Q, R, S, T, W and Y, preferably A, C, D, E, F, G, H, I, N, Q, R, S, T, W and Y, in particular C, D, E, F, N, R, S, T, W and Y, and especially E, T, and W;

a sequence having at least 80% identity with SEQ ID NO: 9 (ASNP D394X₈), said sequence having an amino acid X₈ representing an amino acid chosen from the group consisting of A, E and S, preferably E;

a sequence having at least 80% identity with SEQ ID NO: 10 (ASNP R446X₉), said sequence having an amino acid X₉ representing an amino acid chosen from the group consisting of A, C, Q, S and T, preferably S;

a sequence having at least 80% identity with SEQ ID NO: 12 (alpha-1,2 BrS);

a sequence having at least 80% identity with SEQ ID NO: 13 (ΔN₁₂₃-GBD-CD2);

a sequence having at least 80% identity with SEQ ID NO: 14 (ASDg); and a sequence having at least 80% identity with SEQ ID NO: 16 (alpha-1,3 BrS).

According to a particular embodiment, a process for manufacturing a glycosylated synthon, or monomer, comprises at least one step of placing at least one glycan-saccharase in contact with at least propen-1-ol (allyl alcohol) as hydroxylated synthon and at least one sucrose, in which the glycan-saccharase is chosen from the group comprising:

a sequence having at least 80% identity with SEQ ID NO: 1 (ASNP WT), a sequence having at least 80% identity with SEQ ID NO: 2 (ASNP R226X₁), said sequence having an amino acid X₁ representing an amino acid chosen from the group consisting of A, C, D, E, F, G, H, I, K, L, M, N, P, Q, S, T, V and Y;

a sequence having at least 80% identity with SEQ ID NO: 3 (ASNP I228X₂), said sequence having an amino acid X₂ representing an amino acid chosen from the group consisting of D, E, F, G, H, P, Q, R, S, T, V, W and Y, preferably H;

a sequence having at least 80% identity with SEQ ID NO: 4 (ASNP F229X$_3$), said sequence having an amino acid X$_3$ representing an amino acid chosen from the group consisting of C, D, E, G, H, I, K, L, M, P, Q, R, S, T, V, W and Y, preferably D, E, G, H, I, K and M, in particular D, E, G, I, K and M;

a sequence having at least 80% identity with the sequence SEQ ID NO: 5 (ASNP A289X$_4$), said sequence having an amino acid X$_4$ representing an amino acid chosen from the group consisting of C, D, E, F, G, H, I, K, L, M, P, Q, R, S, T, V, W and Y, preferably C, D, E, F, G, H, I, K, L, M W and Y;

a sequence having at least 80% identity with the sequence SEQ ID NO: 6 (ASNP F290X$_5$), said sequence having an amino acid X$_5$ representing an amino acid chosen from the group consisting of A, C, D, E, G, H, I, K, L, M, P, Q, R, S, T, V, W and Y, preferably C, D, E, G, H, I, K, L, M and W, in particular C and H;

a sequence having at least 80% identity with the sequence SEQ ID NO: 7 (ASNP I330X$_6$), said sequence having an amino acid X$_6$ representing an amino acid chosen from the group consisting of A, C, D, E, F, G, H, K, L, M, N, P, Q, R, S, T, V, W and Y, preferably C, D, E, F, G, H, K, L, M, S and Y, in particular C;

a sequence having at least 80% identity with SEQ ID NO: 8 (ASNP V331X$_7$), said sequence having an amino acid X$_7$ representing an amino acid chosen from the group consisting of A, C, D, E, F, G, H, I, K, L, M, N, P, Q, R, S, T, W and Y, preferably C, D, E, F, G, H, I, K, L, N and W;

a sequence having at least 80% identity with SEQ ID NO: 9 (ASNP D394X$_8$), said sequence having an amino acid X$_8$ representing an amino acid chosen from the group consisting of A, C, E, F, G, H, I, K, L, M, P, Q, R, S, T, V, W and Y, preferably E, F, G, H, I, K and L, in particular E;

a sequence having at least 80% identity with SEQ ID NO: 10 (ASNP R446X$_9$), said sequence having an amino acid X$_9$ representing an amino acid chosen from the group consisting of A, C, D, E, F, G, H, I, K, L, M, Q, S, T, V, W and Y, preferably M;

a sequence having at least 80% identity with SEQ ID NO: 12 (alpha-1,2 BrS);

a sequence having at least 80% identity with SEQ ID NO: 13 (ΔN$_{123}$-GBD-CD2);

a sequence having at least 80% identity with SEQ ID NO: 14 (ASDg);

a sequence having at least 80% identity with SEQ ID NO: 16 (alpha-1,3 BrS); and a sequence having at least 80% identity with SEQ ID NO: 18 (fructosyltransferase of *Bacillus subtilis*).

According to a particular embodiment, a process for manufacturing a glycosylated synthon, or monomer, comprises at least one step of placing at least one glycansaccharase in contact with at least VBA as hydroxylated synthon and at least one sucrose, in which the glycansaccharase is chosen from the group comprising:

a sequence having at least 80% identity with SEQ ID NO: 1 (ASNP WT), a sequence having at least 80% identity with SEQ ID NO: 2 (ASNP R226X$_1$), said sequence having an amino acid X$_1$ representing an amino acid chosen from the group consisting of H, K, M, N, Q, S, T, V and Y, in particular H, K, M, N, Q, S, T and V, preferably H, K, M, N, Q, T and V;

a sequence having at least 80% identity with SEQ ID NO: 3 (ASNP I228X$_2$), said sequence having an amino acid X$_2$ representing an amino acid chosen from the group consisting of V;

a sequence having at least 80% identity with the sequence SEQ ID NO: 5 (ASNP A289X$_4$), said sequence having an amino acid X$_4$ representing an amino acid chosen from the group consisting of M, N, P, Q, S, T and V, preferably M, N, P, Q, S and T, and especially P, Q and S;

a sequence having at least 80% identity with the sequence SEQ ID NO: 6 (ASNP F290X$_5$), said sequence having an amino acid X$_5$ representing an amino acid chosen from the group consisting of V and W;

a sequence having at least 80% identity with SEQ ID NO: 8 (ASNP V331X$_7$), said sequence having an amino acid X$_7$ representing an amino acid chosen from the group consisting of C, D, G, S, T and Y, preferably C, G, S, T and Y;

a sequence having at least 80% identity with SEQ ID NO: 10 (ASNP R446X$_9$), said sequence having an amino acid X$_9$ representing the amino acid A;

a sequence having at least 80% identity with SEQ ID NO: 12 (alpha-1,2 BrS); and a sequence having at least 80% identity with SEQ ID NO: 17 (ASR-C-del-bis).

According to a particular embodiment, a process for manufacturing a glycosylated synthon, or monomer, comprises at least one step of placing at least one glycansaccharase in contact with at least NNHEA as hydroxylated synthon and at least one sucrose, in which the glycansaccharase is chosen from the group comprising:

a sequence having at least 80% identity with SEQ ID NO: 1 (ASNP WT), a sequence having at least 80% identity with SEQ ID NO: 2 (ASNP R226X$_1$), said sequence having an amino acid X$_1$ representing an amino acid chosen from the group consisting of A, D, E, I, K, L, M, N, Q, S, T, V, W and Y;

a sequence having at least 80% identity with SEQ ID NO: 3 (ASNP I228X$_2$), said sequence having an amino acid X$_2$ representing an amino acid chosen from the group consisting of A, C, E, F, H, L, M, N, P, Q, S, T, V, W and Y, preferably V;

a sequence having at least 80% identity with SEQ ID NO: 4 (ASNP F229X$_3$), said sequence having an amino acid X$_3$ representing an amino acid chosen from the group consisting of C, I, L, M, N, Q, R, V, W and Y, preferably M;

a sequence having at least 80% identity with the sequence SEQ ID NO: 5 (ASNP A289X$_4$), said sequence having an amino acid X$_4$ representing an amino acid chosen from the group consisting of C, D, E, F, G, H, I, K, L, M, N, P, Q, R, S, T, V and W, preferably C, G, M, N, Q, S, T and V, in particular Q;

a sequence having at least 80% identity with the sequence SEQ ID NO: 6 (ASNP F290X$_5$), said sequence having an amino acid X$_5$ representing an amino acid chosen from the group consisting of A, C, D, E, G, H, I, K, L, M, P, Q, R, S, T, V, W and Y, preferably A, C, G, I, K, L, M, Q, S, T, V and W, in particular C, L, V and W;

a sequence having at least 80% identity with the sequence SEQ ID NO: 7 (ASNP I330X$_6$), said sequence having an amino acid X$_6$ representing an amino acid chosen from the group consisting of C, K, M, Q, T, V and Y, preferably V;

a sequence having at least 80% identity with SEQ ID NO: 8 (ASNP V331X$_7$), said sequence having an amino acid X$_7$ representing an amino acid chosen from the group consisting of C, D, E, F, G, H, I, K, L, M, N, R, S, T, W and Y, preferably D, E, G, N, S, T and Y;

a sequence having at least 80% identity with SEQ ID NO: 9 (ASNP D394X$_8$), said sequence having an amino acid X$_8$ representing an amino acid chosen from the group consisting of E, G, R and S;

a sequence having at least 80% identity with SEQ ID NO: 10 (ASNP R446X$_9$), said sequence having an amino acid X$_9$ representing an amino acid chosen from the group consisting of C, F, G, K, L, M, N, Q, S, T and Y;

a sequence having at least 80% identity with SEQ ID NO: 16 (alpha-1,3 BrS); and a sequence having at least 80% identity with SEQ ID NO: 17 (ASR-C-del-bis).

A sequence having at least 80% identity with SEQ ID NO: 12 (alpha-1,2 BrS) may also be used in a process for manufacturing a glycosylated synthon according to the invention when NNHEA is the hydroxylated synthon to be glycosylated, in particular to be glucosylated.

According to a particular embodiment, a process for manufacturing a glycosylated synthon, or monomer, comprises at least one step of placing at least one glycan-saccharase in contact with at least HEAA as hydroxylated synthon and at least one sucrose, in which the glycan-saccharase is chosen from the group comprising:

a sequence having at least 80% identity with SEQ ID NO: 9 (ASNP D394X$_8$), said sequence having an amino acid X$_8$ representing E;

a sequence having at least 80% identity with SEQ ID NO: 16 (alpha-1,3 BrS);

a sequence having at least 80% identity with SEQ ID NO: 17 (ASR-C-del-bis); and a sequence having at least 80% identity with SEQ ID NO: 18 (fructosyltransferase of *Bacillus subtilis*).

Thus, the present invention more preferentially relates to a process for manufacturing a glycosylated synthon, or monomer, comprising at least one step of placing at least one glycan-saccharase in contact with at least one hydroxylated synthon and at least one sucrose, in which:

(i) the glycosylated synthon is HEMA and the glycan-saccharase used is chosen from the group comprising:

a sequence having at least 80% identity with SEQ ID NO: 1 (ASNP WT), a sequence having at least 80% identity with SEQ ID NO: 2 (ASNP R226X$_1$), said sequence having an amino acid X$_1$ representing an amino acid chosen from the group consisting of A, C, N, P, S and T, preferably C;

a sequence having at least 80% identity with SEQ ID NO: 3 (ASNP I228X$_2$), said sequence having an amino acid X$_2$ representing an amino acid chosen from the group consisting of P, T and V, preferably T;

a sequence having at least 80% identity with SEQ ID NO: 4 (ASNP F229X$_3$), said sequence having an amino acid X$_3$ representing W;

a sequence having at least 80% identity with the sequence SEQ ID NO: 5 (ASNP A289X$_4$), said sequence having an amino acid X$_4$ representing H, I, K, L, M and W, preferably H and L;

a sequence having at least 80% identity with the sequence SEQ ID NO: 6 (ASNP F290X$_5$), said sequence having an amino acid X$_5$ representing an amino acid chosen from the group consisting of A, C, H, I, K, L, M, N, P, Q, V and W, preferably A, C, I, K, L, M, P and V, in particular A, C, I, K, L, M and V, and especially A, C, I, L and V;

a sequence having at least 80% identity with the sequence SEQ ID NO: 7 (ASNP I330X$_6$), said sequence having an amino acid X$_6$ representing A, C, E, F, G, H, K, L, M and N, preferably A;

a sequence having at least 80% identity with SEQ ID NO: 8 (ASNP V331X$_7$), said sequence having an amino acid X$_7$ representing an amino acid chosen from the group consisting of A, C, D, E, F, G, H, K, L, M, in particular C, D, E, G, H, and especially E;

a sequence having at least 80% identity with SEQ ID NO: 9 (ASNP D394X$_8$), said sequence having an amino acid X$_8$ representing A, C, E, G, H, I, L, M and N, in particular A;

a sequence having at least 80% identity with SEQ ID NO: 10 (ASNP R446X$_9$), said sequence having an amino acid X$_9$ representing an amino acid chosen from the group consisting of A, C, D, E, F, G, H, I, K, L, M and N, preferably C, G, K, L and N, especially N;

a sequence having at least 80% identity with SEQ ID NO: 12 (alpha-1,2 BrS);

a sequence having at least 80% identity with SEQ ID NO: 13 ($\Delta$N$_{123}$-GBD-CD2);

a sequence having at least 80% identity with SEQ ID NO: 14 (ASDg);

a sequence having at least 80% identity with SEQ ID NO: 16 (alpha-1,3 BrS);

a sequence having at least 80% identity with SEQ ID NO: 17 (ASR-C-del-bis); and a sequence having at least 80% identity with SEQ ID NO: 18 (fructosyltransferase of *Bacillus subtilis*);

(ii) the hydroxylated synthon is NHAM and the glycan-saccharase used in a process of the invention is chosen from the group comprising:

a sequence having at least 80% identity with SEQ ID NO: 1 (ASNP WT), a sequence having at least 80% identity with SEQ ID NO: 2 (ASNP R226X$_1$), said sequence having an amino acid X$_1$ representing an amino acid chosen from the group consisting of A, C, D, E, F, G, H, I, K, L, M, N, Q, S, T, V, W and Y;

a sequence having at least 80% identity with SEQ ID NO: 3 (ASNP I228X$_2$), said sequence having an amino acid X$_2$ representing an amino acid chosen from the group consisting of C, E, L, M, N, P, Q, R, T, V and Y;

a sequence having at least 80% identity with SEQ ID NO: 4 (ASNP F229X$_3$), said sequence having an amino acid X$_3$ representing an amino acid chosen from the group consisting of A, C, I, L, M, N, P, Q, V, W and Y, preferably M;

a sequence having at least 80% identity with the sequence SEQ ID NO: 5 (ASNP A289X$_4$), said sequence having an amino acid X$_4$ representing an amino acid chosen from the group consisting of C, D, E, F, G, H, I, L, M, N, P, Q, S, T and V, preferably N, P, Q, S, and V, especially N, P and Q;

a sequence having at least 80% identity with the sequence SEQ ID NO: 6 (ASNP F290X$_5$), said sequence having an amino acid X$_5$ representing an amino acid chosen from the group consisting of A, C, G, L, M, N, P, Q, V, W and Y;

a sequence having at least 80% identity with the sequence SEQ ID NO: 7 (ASNP I330X$_6$), said sequence having an amino acid $X_6$ representing an amino acid chosen from the group consisting of A, M, N and V, preferably N;
a sequence having at least 80% identity with SEQ ID NO: 8 (ASNP V331$X_7$), said sequence having an amino acid $X_7$ representing an amino acid chosen from the group consisting of A, C, D, E, F, G, H, I, L, M, N, P, Q, R, S, T and Y, preferably C, D, E, N, and T, especially E;
a sequence having at least 80% identity with SEQ ID NO: 9 (ASNP D394$X_8$), said sequence having an amino acid $X_8$ representing an amino acid chosen from the group consisting of C, E, G and N, preferably E;
a sequence having at least 80% identity with SEQ ID NO: 10 (ASNP R446$X_9$), said sequence having an amino acid $X_9$ representing an amino acid chosen from the group consisting of A, C, F, G, K, L, M, N, Q, S, T and Y;
a sequence having at least 80% identity with SEQ ID NO: 11 (DSR-S vardelΔ4N-S512C);
a sequence having at least 80% identity with SEQ ID NO: 12 (alpha-1,2 BrS);
a sequence having at least 80% identity with SEQ ID NO: 13 ($\Delta N_{123}$-GBD-CD2);
a sequence having at least 80% identity with SEQ ID NO: 14 (ASDg);
a sequence having at least 80% identity with SEQ ID NO: 15 (DSR-S-OK);
a sequence having at least 80% identity with SEQ ID NO: 16 (alpha-1,3 BrS);
a sequence having at least 80% identity with SEQ ID NO: 17 (ASR-C-del-bis); and
a sequence having at least 80% identity with SEQ ID NO: 18 (fructosyltransferase of *Bacillus subtilis*);
(iii) the glycosylated synthon is 2-mercaptoethanol (BME) and the glycan-saccharase is chosen from the group comprising:
a sequence having at least 80% identity with SEQ ID NO: 1 (ASNP WT);
a sequence having at least 80% identity with SEQ ID NO: 3 (ASNP I228$X_2$), said sequence having an amino acid $X_2$ representing an amino acid chosen from the group consisting of A, E, F, H, L, M, N, Q, R, V, W and Y, preferably L, V, W and Y;
a sequence having at least 80% identity with SEQ ID NO: 4 (ASNP F229$X_3$), said sequence having an amino acid $X_3$ representing an amino acid chosen from the group consisting of A, C, I, L, M, P, Q, R, V, W and Y, preferably C, M, P, Q, V, W and Y, in particular C, M, P, V and Y, especially Y;
a sequence having at least 80% identity with the sequence SEQ ID NO: 5 (ASNP A289$X_4$), said sequence having an amino acid $X_4$ representing an amino acid chosen from the group consisting of C, D, E, F, G, H, I, M, N, P, Q, R, S, T, V and W, preferably C, D, E, F, M, N, P, Q, S, T, V and W, and especially F, M, N, P, Q, S and T;
a sequence having at least 80% identity with the sequence SEQ ID NO: 6 (ASNP F290$X_5$), said sequence having an amino acid $X_5$ representing an amino acid chosen from the group consisting of A, C, D, E, G, H, I, K, L, M, P, Q, R, S, T, V, W and Y, preferably A, C, D, E, G, I, M, P, Q, S, T, V and W, in particular D, Q, S, T and W, and especially S, T and W;
a sequence having at least 80% identity with the sequence SEQ ID NO: 7 (ASNP I330$X_6$), said sequence having an amino acid $X_6$ representing an amino acid chosen from the group consisting of A, N, Q, S, T, V and W, preferably Q and V;
a sequence having at least 80% identity with SEQ ID NO: 8 (ASNP V331$X_7$), said sequence having an amino acid $X_7$ representing an amino acid chosen from the group consisting of A, C, D, E, F, G, H, I, K, L, N, Q, R, S, T, W and Y, preferably A, C, D, E, F, G, H, I, N, Q, R, S, T, W and Y, in particular C, D, E, F, N, R, S, T, W and Y, and especially E, T, and W;
a sequence having at least 80% identity with SEQ ID NO: 9 (ASNP D394$X_8$), said sequence having an amino acid $X_8$ representing an amino acid chosen from the group consisting of A, E and S, preferably E;
a sequence having at least 80% identity with SEQ ID NO: 10 (ASNP R446$X_9$), said sequence having an amino acid $X_9$ representing an amino acid chosen from the group consisting of A, C, Q, S and T, preferably S;
a sequence having at least 80% identity with SEQ ID NO: 12 (alpha-1,2 BrS);
a sequence having at least 80% identity with SEQ ID NO: 13 ($\Delta N_{123}$-GBD-CD2);
a sequence having at least 80% identity with SEQ ID NO: 14 (ASDg); and
a sequence having at least 80% identity with SEQ ID NO: 16 (alpha-1,3 BrS);
(iv) the hydroxylated synthon is propen-1-ol (allyl alcohol) and the glycan-saccharase is chosen from the group comprising:
a sequence having at least 80% identity with SEQ ID NO: 1 (ASNP WT),
a sequence having at least 80% identity with SEQ ID NO: 2 (ASNP R226$X_1$), said sequence having an amino acid $X_1$ representing an amino acid chosen from the group consisting of A, C, D, E, F, G, H, I, K, L, M, N, P, Q, S, T, V and Y;
a sequence having at least 80% identity with SEQ ID NO: 3 (ASNP I228$X_2$), said sequence having an amino acid $X_2$ representing an amino acid chosen from the group consisting of D, E, F, G, H, P, Q, R, S, T, V, W and Y, preferably H;
a sequence having at least 80% identity with SEQ ID NO: 4 (ASNP F229$X_3$), said sequence having an amino acid $X_3$ representing an amino acid chosen from the group consisting of C, D, E, G, H, I, K, L, M, P, Q, R, S, T, V, W and Y, preferably D, E, G, H, I, K and M, in particular D, E, G, I, K and M;
a sequence having at least 80% identity with the sequence SEQ ID NO: 5 (ASNP A289$X_4$), said sequence having an amino acid $X_4$ representing an amino acid chosen from the group consisting of C, D, E, F, G, H, I, K, L, M, P, Q, R, S, T, V, W and Y, preferably C, D, E, F, G, H, I, K, L, M, W and Y;
a sequence having at least 80% identity with the sequence SEQ ID NO: 6 (ASNP F290$X_5$), said sequence having an amino acid $X_5$ representing an amino acid chosen from the group consisting of A, C, D, E, G, H, I, K, L, M, P, Q, R, S, T, V, W and Y, preferably C, D, E, G, H, I, K, L, M and W, in particular C and H;
a sequence having at least 80% identity with the sequence SEQ ID NO: 7 (ASNP I330$X_6$), said sequence having an amino acid $X_6$ representing an amino acid chosen from the group consisting of A, C, D, E, F, G, H, K, L, M, N, P, Q, R, S, T, V, W and Y, preferably C, D, E, F, G, H, K, L, M, S and Y, in particular C;
a sequence having at least 80% identity with SEQ ID NO: 8 (ASNP V331$X_7$), said sequence having an amino acid X₇ representing an amino acid chosen from the group consisting of A, C, D, E, F, G, H, I, K, L, M, N, P, Q, R, S, T, W and Y, preferably C, D, E, F, G, H, I, K, L, N and W;

a sequence having at least 80% identity with SEQ ID NO: 9 (ASNP D394X₈), said sequence having an amino acid X₈ representing an amino acid chosen from the group consisting of A, C, E, F, G, H, I, K, L, M, P, Q, R, S, T, V, W and Y, preferably E, F, G, H, I, K and L, in particular E;

a sequence having at least 80% identity with SEQ ID NO: 10 (ASNP R446X₉), said sequence having an amino acid X₉ representing an amino acid chosen from the group consisting of A, C, D, E, F, G, H, I, K, L, M, Q, S, T, V, W and Y, preferably M;

a sequence having at least 80% identity with SEQ ID NO: 12 (alpha-1,2 BrS);

a sequence having at least 80% identity with SEQ ID NO: 13 (ΔN₁₂₃-GBD-CD2);

a sequence having at least 80% identity with SEQ ID NO: 14 (ASDg);

a sequence having at least 80% identity with SEQ ID NO: 16 (alpha-1,3 BrS); and a sequence having at least 80% identity with SEQ ID NO: 18 (fructosyltransferase of *Bacillus subtilis*);

(v) the glycosylated synthon is VBA and the glycan-saccharase is chosen from the group comprising:

a sequence having at least 80% identity with SEQ ID NO: 1 (ASNP WT), a sequence having at least 80% identity with SEQ ID NO: 2 (ASNP R226X₁), said sequence having an amino acid X₁ representing an amino acid chosen from the group consisting of H, K, M, N, Q, S, T, V and Y, in particular H, K, M, N, Q, S, T and V, preferably H, K, M, N, Q, T and V;

a sequence having at least 80% identity with SEQ ID NO: 3 (ASNP I228X₂), said sequence having an amino acid X₂ representing an amino acid chosen from the group consisting of V;

a sequence having at least 80% identity with the sequence SEQ ID NO: 5 (ASNP A289$X_4$), said sequence having an amino acid $X_4$ representing an amino acid chosen from the group consisting of M, N, P, Q, S, T and V, preferably M, N, P, Q, S and T, and especially P, Q and S;

a sequence having at least 80% identity with the sequence SEQ ID NO: 6 (ASNP F290$X_5$), said sequence having an amino acid $X_5$ representing an amino acid chosen from the group consisting of V and W;

a sequence having at least 80% identity with SEQ ID NO: 8 (ASNP V331$X_7$), said sequence having an amino acid $X_7$ representing an amino acid chosen from the group consisting of C, D, G, S, T and Y, preferably C, G, S, T and Y;

a sequence having at least 80% identity with SEQ ID NO: 10 (ASNP R446$X_9$), said sequence having an amino acid $X_9$ representing the amino acid A;

a sequence having at least 80% identity with SEQ ID NO: 12 (alpha-1,2 BrS); and a sequence having at least 80% identity with SEQ ID NO: 17 (ASR-C-del-bis); (vi) the glycosylated synthon is NNHEA and the glycan-saccharase is chosen from the group comprising:

a sequence having at least 80% identity with SEQ ID NO: 1 (ASNP WT), a sequence having at least 80% identity with SEQ ID NO: 2 (ASNP R226$X_1$), said sequence having an amino acid $X_1$ representing an amino acid chosen from the group consisting of A, D, E, I, K, L, M, N, Q, S, T, V, W and Y;

a sequence having at least 80% identity with SEQ ID NO: 3 (ASNP I228$X_2$), said sequence having an amino acid $X_2$ representing an amino acid chosen from the group consisting of A, C, E, F, H, L, M, N, P, Q, S, T, V, W and Y, preferably V;

a sequence having at least 80% identity with SEQ ID NO: 4 (ASNP F229$X_3$), said sequence having an amino acid $X_3$ representing an amino acid chosen from the group consisting of C, I, L, M, N, Q, R, V, W and Y, preferably M;

a sequence having at least 80% identity with the sequence SEQ ID NO: 5 (ASNP A289$X_4$), said sequence having an amino acid $X_4$ representing an amino acid chosen from the group consisting of C, D, E, F, G, H, I, K, L, M, N, P, Q, R, S, T, V and W, preferably C, G, M, N, Q, S, T and V, in particular Q;

a sequence having at least 80% identity with the sequence SEQ ID NO: 6 (ASNP F290$X_5$), said sequence having an amino acid $X_5$ representing an amino acid chosen from the group consisting of A, C, D, E, G, H, I, K, L, M, P, Q, R, S, T, V, W and Y, preferably A, C, G, I, K, L, M, Q, S, T, V and W, in particular C, L, V and W;

a sequence having at least 80% identity with the sequence SEQ ID NO: 7 (ASNP I330$X_6$), said sequence having an amino acid $X_6$ representing an amino acid chosen from the group consisting of C, K, M, Q, T, V and Y, preferably V;

a sequence having at least 80% identity with SEQ ID NO: 8 (ASNP V331$X_7$), said sequence having an amino acid $X_7$ representing an amino acid chosen from the group consisting of C, D, E, F, G, H, I, K, L, M, N, R, S, T, W and Y, preferably D, E, G, N, S, T and Y;

a sequence having at least 80% identity with SEQ ID NO: 9 (ASNP D394$X_8$), said sequence having an amino acid $X_8$ representing an amino acid chosen from the group consisting of E, G, R and S;

a sequence having at least 80% identity with SEQ ID NO: 10 (ASNP R446$X_9$), said sequence having an amino acid $X_9$ representing an amino acid chosen from the group consisting of C, F, G, K, L, M, N, Q, S, T and Y;

a sequence having at least 80% identity with SEQ ID NO: 12 (alpha-1,2 BrS);

a sequence having at least 80% identity with SEQ ID NO: 16 (alpha-1,3 BrS); and a sequence having at least 80% identity with SEQ ID NO: 17 (ASR-C-del-bis); or (vii) the glycosylated synthon is HEAA and the glycan-saccharase is chosen from the group comprising:

a sequence having at least 80% identity with SEQ ID NO: 9 (ASNP D394$X_8$), said sequence having an amino acid $X_8$ representing E;

a sequence having at least 80% identity with SEQ ID NO: 16 (alpha-1,3 BrS);

a sequence having at least 80% identity with SEQ ID NO: 17 (ASR-C-del-bis); and a sequence having at least 80% identity with SEQ ID NO: 18 (fructosyltransferase of *Bacillus subtilis*).

c) Implementation of the Monomers of the Invention

The monomers of the invention are polymerizable and/or may be coupled via a coupling reaction, and may be used in a process for manufacturing a glyco(co)polymer according to the invention, comprising the polymerization and/or coupling reaction of at least two of these monomers.

A chemo-enzymatic process according to the invention is advantageous in many respects, especially such as the very short reaction time, making it possible, in the space of a few hours, especially in the space of 24 hours, to go from the hydroxylated synthons to the glyco(co)polymers of interest.

In addition, the determination by the inventors (i) of synthons with variable structures that are capable of being glycosylated in a process according to the invention and (ii) of enzymes with different specificities, allows the "tailor-made" production of glyco(co)polymers with great variability.

The polymerization and the coupling reaction according to the invention also make it possible to gain access to novel molecular architectures, such as comb or block (co)polymers, which may be evaluated for the development of novel materials of modifiable hydrophilic/hydrophobic balance.

Such a process may especially be performed under the conditions stated in example 6 below.

According to one embodiment, a process for manufacturing a glyco(co)polymer by polymerization according to the invention comprises, in the following order, the following steps:

a) polymerization of two monomers of the invention, making it possible to obtain a chain of two monomers;

b) polymerization of the monomer chain obtained on conclusion of the preceding step with a monomer of the invention; and then c) one or more successive, and independent, steps consisting in polymerizing the monomer chain obtained on conclusion of the preceding step with a monomer of the invention.

According to one embodiment, such a polymerization process may also comprise, independently:

at least one step a') between steps a) and b);
at least one step b') between steps b) and c); and/or
at least one step c') after any one of the steps c), in which the monomer chain obtained on conclusion of the preceding step is polymerized with at least one non-glycosylated synthon.

EXAMPLES

Example 1: Production and Use of Glucan-Saccharases for the Glucosylation of 2-(Hydroxy)ethyl Methacrylate (HEMA) and N-(Hydroxy)Methylacrylamide (NHAM)

A library comprising 8 wild-type enzymes (belonging to the glycoside-hydrolase families GH70 and 13) and 171 single mutants (positions 226, 228, 229, 289, 290, 330, 331, 394 and 446) constructed from the amylosaccharase of *Neisseria polysaccharea* (ASNp) (GH13 family) were tested for their ability to glucosylate HEMA and NHAM.

The glucan-saccharases selected for the study, and the origin thereof, are indicated in Table 1.

Table 1 in fact illustrates a certain number of glucan-saccharases tested in the examples of the present text and specifies: column 1: the organism from which the enzyme is derived; column 2: the various wild-type enzymes tested and also the mutated positions of the active site of these wild-type enzymes in the mutated glucan-saccharases also tested; column 3: the bibliographic references in which these enzymes, in both wild-type and mutated forms, were described in the prior art.

These enzymes were used in recombinant form and are expressed in *Escherichia coli*.

1.1. Production of the Enzymes in Microplates

All of the strains of *Escherichia coli*, overexpressing the heterologous glucan-saccharases of the families GH13 and GH70, of wild type or mutants thereof (Table 1), are stored in 96-well microplate format in order to facilitate the future steps of screening for glucosylation of the hydroxylated synthons.

From the source microplates, preculturing of these *E. coli* strains is performed for 22 hours at 30° C., 700 rpm in 96-well microplates, in 200 µL of Luria-Bertani culture medium supplemented with 100 µg/mL of ampicillin.

These pre-cultures are in turn used to seed "deep-well" microplates, each well of which contains 1 mL per well of auto-inducible medium ZYM5052 especially containing 0.2% (w/v) of α-lactose, 0.05% (w/v) of D-glucose, 0.5% (w/v) of glycerol and 0.05% (w/v) of L-arabinose (Studier et al., Protein Expr. Purif. 2005 May; 41(1): 207-34).

After culturing for 22 hours at 30° C. and at 700 rpm, the cell suspension is centrifuged for 20 minutes at 3000 g at 4° C. The cell pellets are resuspended in the 96-well deep-well microplates, with 300 µL of phosphate-buffered saline (24 mM sodium/potassium phosphate and 274 mM NaCl) containing 0.5 g/L of lysozyme and 5 mg/L of bovine pancreatic RNAse.

This is followed by incubation for 30 minutes at 30° C. with stirring, and these microplates are then stored overnight at −80° C. After thawing, the microplates are shaken vigorously and then centrifuged for 20 minutes at 3000 g at 4° C.

The centrifuged supernatants containing the recombinant enzymes are transferred into clean 96-well deep-well microplates to perform the acceptor reactions.

1.2. Test of Enzymatic Activity on Sucrose

Before performing the enzymatic glucosylation screening reactions, 50 µL of the supernatants are used to perform an enzymatic activity test on sucrose.

The enzymatic activity is evaluated in microplate format at the end point after 30 minutes of incubation of 146 mM final of sucrose by assaying the reducing sugars with 3,5-dinitrosalicylic acid (DNS).

After twofold dilution in water, the absorbance is read at 540 nm.

1.3. Conditions for Performing the Enzymatic Activity Tests on the Acceptors

For the screening of the bank of *Neisseria polysaccharea* amylosaccharase mutants, the acceptor reactions are performed in deep-well microplates in a volume of 300 µL, in the presence of 73 mM of sucrose, 73 mM of acceptor (HEMA, NHAM or the like) at final concentrations and 150 µL of centrifuged cell lyzate.

The microplates are incubated at 30° C. and at 700 rpm.

After reaction for 24 hours, the enzymes are denatured at 95° C. for 10 minutes. These microplates are stored at −20° C. for the purpose of rapid analysis of the glucosylation by HPLC/MS.

For the screening of the wild-type enzymes, the acceptor reactions are performed in tubes in a volume of 1 mL, in the presence of 146 mM of sucrose, 438 mM of acceptor (HEMA or NHAM) at final concentrations of 1 U/mL of enzymatic activity.

The tubes are incubated at 30° C. and shaken at 500 rpm.

After reaction for 24 hours, the enzymes are denatured at 95° C. for 10 minutes and the reaction media are centrifuged, filtered, diluted and analyzed by LC/MS.

1.4. LC and LC/MS Analytical Methods for the Acceptor Reaction Products

Analysis of the acceptor reactions is performed in two stages.

A first short HPLC analysis on a Hypercarb column (6 minutes) is performed to identify the presence or absence of glucosylation products.

The second HPLC analysis on a Hypercarb or Amino column (30 minutes) allows separation and identification of all the constituents of the reaction mixture.

In the case of an LC-MS analysis, the Dionex HPLC system is coupled to a ThermoScientific MSQP1us single quadrupole mass spectrometer.

The conditions used are summarized in Table 2.

The amount of glycosylation products (in g/L) was estimated on the basis of the coefficient of response of the acceptor in UV detection.

Example 2: Determination of the Efficiencies of HEMA and NHAM Glucosylation by the Enzymes of Example 1

The reactions in the presence of acceptor were performed by applying the conditions described in example 1.

In a first stage, these acceptor reactions were performed with a panel of seven wild-type glycan-saccharases of different specificities, these enzymes being indicated in Table 1, namely: ASDg, ASR, GBD-CD2, DSR-S-Δ4N, DSR-OK, α-1,2-BrS and α-1,3-BrS.

After reaction for 24 hours, the reaction medium is analyzed by HPLC-MS on a Hypercarb column (30 minutes) to identify the glucosylation products.

Tables 3 and 4 show the degree of conversion of sucrose and the three main glucosylation products obtained in the presence, respectively, of HEMA and of NHAM in g/L, characterized by MS and corresponding, respectively, to the mono-glucosylated acceptor (Acceptor-Glc1), di-glucosylated acceptor (Acceptor-Glc2) and tri-glucosylated acceptor (Acceptor-Glc3). Products in smaller amounts are also detected, corresponding to tetra-, penta-, hexa- and hepta-glucosylated forms.

Given the presence of only one reactive hydroxyl group on the molecule, only one type of mono-glycosylation of the molecule is expected, and thus the same mono-glucosylated product irrespective of the enzyme.

On the other hand, the structure of the di- and tri-glucosylated products may differ as a function of the specificity of the enzyme, and the structure of the products will be able to be determined unambiguously only by NMR analysis.

Glucosylation Results

With the exception of DSR-S-Δ4N and DSR-OK, which do not recognize HEMA, all the wild-type glycan-saccharases tested glucosylate the acceptors HEMA and NHAM with variable efficiencies and variable glucosylation product sizes.

HEMA Glucosylation Results

The reactions performed in the presence of the enzymes ASR and ASDg led to particularly high degrees of sucrose conversion (95%) accompanied by the production of glucosylated acceptor products ranging from 2.7 to 21 g/L.

Among these enzymes, ASR synthesizes a significantly higher level of glucosylated HEMA (21 g/L). With ASR, the products formed are distributed in equivalent proportions between the mono-, di- and tri-glucosylated forms of HEMA.

It is also observed that the use of the enzyme GBD-CD2 leads only to mono-glucosylated HEMAs. Thus, the use of this enzyme advantageously makes it possible to obtain only mono-glucosylated HEMAs.

In this sense, it is observed that the use of the enzymes α-1,2-BrS and α-1,3-BrS, also show a very high degree of sucrose conversion (93% and 84%, respectively), leads mainly to the production of mono-glucosylated HEMAs.

NHAM Glucosylation Results

All the glycan-saccharases prove to be capable of recognizing NHAM and of glucosylating it, but in proportions 2.5 to 5 times lower than the levels observed for HEMA.

The enzymes GBD-CD2, α-1,2-BrS and α-1,3-BrS are the greatest producers of glucosylated NHAM with levels of the order of 2 g/L.

The mono-glucosylated form of NHAM remains the product observed in the largest amount.

Example 3: Determination of the Efficiencies of HEMA and NHAM Glucosylation with N. polysaccharea Amylosaccharase (ASNp) and with its Mutants HEMA and NHAM were then tested in an acceptor reaction using Neisseria polysaccharea amylosaccharase (ASNP) and its bank of mono-mutants identified in Table 1.

The glucosylation reactions performed in the presence of acceptor were analyzed in a first stage using a short HPLC method (6 minutes) for the purpose of rapidly identifying the enzymes that are efficient in the glucosylation of the acceptor.

The results obtained for HEMA are summarized in Table 5. The values given represent the productions in g/L calculated from the relative areas derived from the detection by ELSD of the HEMA glucosylation products relative to the wild-type enzyme (the relative area of which is 1).

The results obtained for NHAM are summarized in Table 6. The amount of the glycosylation products (in g/L) was estimated on the basis of the coefficient of response of the acceptor in UV detection.

HEMA Glucosylation Results

The wild-type enzyme ASNp and 69 mono-mutated enzymes proved to be capable of glucosylating HEMA, as represented in Table 5.

More particularly, 25 mutants were seen to glucosylate HEMA more efficiently than the parent wild-type enzyme, namely R226C, I228T, F229W, A289H, A289L, F290A, F290C, F290I, F290K, F290L, F290M, F290P, F290V, I330A, V331C, V331D, V331E, V331G, V331H, D394A, R446C, R446G, R446K, R446L and R446N, and especially the mutants F290A, F290C, F290I, F290K, F290L, F290M, F290V, I330A, V331E, D394A and R446N, in particular F290A, F290C, F290I, F290L, F290V and I330A.

Among these mutants, those targeting position 290 proved to be the most efficient in terms of HEMA glucosylation.

NHAM Glucosylation Results

The wild-type enzyme ASNp and 103 mono-mutated enzymes proved to be capable of glucosylating NHAM, as represented in Table 6.

More particularly, 13 mutants were seen to glucosylate NHAM at least as efficiently as the parent wild-type enzyme, namely F229M, A289N, A289P, A289Q, A289S, A289V, I330N, V331C, V331D, V331E, V331N, V331T and D394E.

In particular, 11 of them were seen to glucosylate NHAM more efficiently than the parent wild-type enzyme, namely F229M, A289N, A289P, A289Q, I330N, V331C, V331D, V331E, V331N, V331T and D394E, and especially the mutants F229M, V331E and D394E.

Example 4: Study of the HEMA and NHAM Glucosylation Products of Example 3

Following the screening, a certain number of mutants tested in Example 3 were analyzed more finely by LC-MS ($UV_{210}$ detection for HEMA, $UV_{215}$ detection for NHAM), according to the protocol indicated in example I so as to analyze the glucosylation products obtained.

Thus, HEMA was glucosylated with the enzymes described in Table 7, resulting from the screening presented in example 3. Mono-, di- and/or tri-glucosylated HEMA compounds were thus obtained.

In other similar tests, tetra-glucosylated HEMA compounds, or even HEMA compounds glucosylated up to 10 times, were also obtained.

As regards NHAM, it was glucosylated with the enzymes described in Table 8, resulting from the screening presented in example 3. Mono-, di- and/or tri-glucosylated NHAM compounds were thus obtained.

Example 5: Gram-Scale Production of HEMA and NHAM Glucosylation Products Using the Selected Enzymes 1. Gram-Scale Production Using the most efficient glycan-saccharases identified, ASR and α-1,3-BrS, and also the mono-mutants F290C and D394E of ASNp, batches of glucosylated HEMA and of glucosylated NHAM were produced at the gram scale in order to perform the polymerization tests.

The reactions are performed in a final volume of 500 mL, in the presence of 143 mM of sucrose, 438 mM of acceptors and 1 U/mL of enzyme. After total consumption of the sucrose, the enzyme is deactivated at 95° C. and the reaction medium is concentrated by lyophilization for a subsequent purification step.

The estimated production levels are given in Table 9.

2. Purification of the Glucosylation Products

The object of the purification is to remove the residual sugars.

The purification is performed by flash chromatography on a Reveleris C18 column of 80 g to 120 g (Alltech, Epernon, France) using a water/acetonitrile gradient.

Example 6: Implementation of the Polymerization Reactions Using the Glucosylated HEMAs Mixtures of glycosylated monomers were polymerized. Typically, the radical polymerization of a 61/18/21 HEMA-Glc/HEMA-(Glc)2/HEMA-(Glc)3 molar mixture was performed.

Controlled radical polymerization techniques such as ATRP (atom-transfer radical polymerization) and RAFT (reversible addition fragmentation transfer) were favored.

A typical ATRP polymerization proceeds as follows.

4-(Bromomethyl)benzoic acid (polymerization initiator, 10.7 mg, 50 µmol, 1 eq.) is poured into 10 mL of water (milliQ) and aqueous NaOH solution (0.5 mL, 0.1 M) is added. The mixture is stirred until dissolution is complete.

The solution is then degassed by sparging with argon, and bipyridine (ligand, 15.7 mg, 100 µmol, 2 eq.) and CuIBr (catalyst, 7.1 mg, 50 µmol, 1 eq.) are added in this order. 20 mL of a degassed solution of the mixture of glycosylated HEMA monomers are added (0.78 g, 2.0 mmol, 40 eq.).

The polymerization then proceeds for 8 hours at room temperature.

The reaction is stopped by air oxidation of the CuI to CuII (the solution changes from brown to blue). The solution is then passed through a column of silica to remove the CuII. The reaction medium is then lyophilized to recover the polymer in the form of a white powder.

The polymerization yield is generally greater than 90%.

Example 7: Implementation of the Glucosylation Method on 2-Propenol (Allyl Alcohol) and on 2-Mercaptoethanol (BME)

Glucosylation of Allyl Alcohol and BME

The process described in the preceding examples was used in order to glucosylate other hydroxylated synthons suitable for use in the invention in order to perform coupling reactions.

Thus, 2-propenol (allyl alcohol) and 2-mercaptoethanol (BME) were tested in the same protocol described above using the wild-type and mutated glycan-saccharases previously used with HEMA and NHAM.

Results

The results relating to allyl alcohol are presented in Tables 10 and 12. The results relating to BME are presented in Tables 11 and 13.

The results indicate that four of the wild-type enzymes tested are capable of glycosylating the acceptor molecules, namely ASDg, GBD-CD2, α-1,2-BrS and α-1,3-BrS.

In a similar manner to what was observed for HEMA and NHAM, we observe that α-1,2-BrS and α-1,3-BrS are the most efficient enzymes for performing the glucosylation of these two acceptors.

In addition, the wild-type ASNp and the very large majority of the mutants tested prove to be capable of glucosylating 2-propenol, as illustrated in Table 12.

More particularly, 60 mutants were seen to glucosylate allyl alcohol at least as efficiently as the parent wild-type enzyme, namely I228H, F229D, F229E, F229G, F229H, F229I, F229K, F229M, A289C, A289D, A289E, A289F, A289G, A289H, A289I, A289K, A289L, A289M, A289W, A289Y, F290C, F290D, F290E, F290G, F290H, F290I, F290K, F290L, F290M, F290W, I330C, I330D, I330E, I330F, I330G, I330H, I330K, I330L, I330M, I330S, I330Y, V331C, V331D, V331E, V331F, V331G, V331H, V331I, V331K, V331L, V331N, V331W, D394E, D394F, D394G, D394H, D394I, D394K, D394L and R446M.

In particular, with the exception of F229H, all these mono-mutants were seen to glucosylate allyl alcohol more efficiently than the parent wild-type enzyme, and especially F290C, F290H, I330C, D394E and R446M.

The wild-type ASNp and 89 mono-mutants also prove to be capable of glucosylating BME, as illustrated in Table 13.

More particularly, 59 mutants were seen to glucosylate BME at least as efficiently as the parent wild-type enzyme, namely:

I228L, I228V, I228W, I228Y, F229C, F229M, F229P, F229Q, F229V, F229Y, A289C, A289D, A289E, A289F, A289G, A289H, A289I, A289M, A289N, A289P, A289Q, A289R, A289S, A289T, A289V, A289W, F290A, F290C, F290D, F290E, F290G, F290I, F290K, F290M, F290P, F290Q, F290S, F290T, F290V, F290W, I330Q, I330V, V331A, V331C, V331D, V331E, V331F, V331G, V331H, V331I, V331N, V331Q, V331R, V331S, V331T, V331W, V331Y, D394E and R446S.

In particular, 57 of them were seen to glucosylate BME more efficiently than the parent wild-type enzyme, namely:

I228L, I228V, I228W, I228Y, F229C, F229M, F229P, F229V, F229Y, A289C, A289D, A289E, A289F, A289G, A289H, A289I, A289M, A289N, A289P, A289Q, A289R, A289S, A289T, A289V, A289W, F290A, F290C, F290D, F290E, F290G, F290I, F290M, F290P, F290Q, F290S, F290T, F290V, F290W, I330Q, I330V, V331A, V331C, V331D, V331E, V331F, V331G, V331H, V331I, V331N, V331Q, V331R, V331S, V331T, V331W, V331Y, D394E and R446S, and in particular F229Y, A289C, A289D, A289E, A289F, A289M, A289N, A289P, A289Q, A289S, A289T, A289V, A289W, F290D, F290Q, F290S, F290T, F290W, V331C, V331D, V331E, V331F, V331N, V331R, V331S, V331T, V331W and V331Y, and especially A289F, A289M, A289N, A289P, A289Q, A289S, A289T, F290S, F290T, F290W, V331E, V331T and V331W.

Example 8: Determination of the Efficiencies of Glucosylation of 4-Vinylbenzyl Alcohol (VBA) with N, Polysaccharea Amylosaccharase (ASNp), with its Mutants and with Certain Enzymes of Example 1

VBA was tested in an acceptor reaction using *Neisseria polysaccharea* amylosaccharase (ASNp), its bank of mono-mutants identified in Table 1, as described in example 3, and also using α-1,2-BrS and ASR.

The results obtained for VBA with the enzymes α-1,2-BrS and ASR are represented in Table 14, while the results obtained for VBA with ASNP and its mono-mutants are summarized in Table 15.

VBA Glucosylation Results

Firstly, it is observed that the enzymes α-1,2-BrS and ASR can glucosylate VBA.

In addition, VBA may be glucosylated with wild-type ASNp, and also with 26 of its tested mono-mutants, namely: R226H, R226K, R226M, R226N, R226Q, R226S, R226T, R226V, R226Y, I228V, A289M, A289N, A289P, A289Q, A289S, A289T, A289V, F290V, F290W, V331C, V331D, V331G, V331S, V331T, V331Y and R446A.

In particular, all these mono-mutants, with the exception of R226S, were seen to glucosylate VBA more efficiently than the parent wild-type enzyme, and especially A289M, A289N, A289P, A289Q, A289S, A289T, V331C, V331G, V331S, V331T, V331Y and R446A, in particular A289P, A289Q, A289S and R446A.

Example 9: Determination of the Efficiencies of Glucosylation of N,N-bis(2-Hydroxyethyl)Acrylamide (NNHEA) with *N. polysaccharea* Amylosaccharase (ASNp), with its Mutants and with Certain Enzymes of Example 1

NNHEA was tested in an acceptor reaction using *Neisseria polysaccharea* amylosaccharase (ASNp), its bank of mono-mutants identified in Table 1, as described in example 3, and also using α-1,2-BrS, α-1,3-BrS and ASR.

The results obtained for NNHEA with the enzymes α-1,2-BrS, α-1,3-BrS and ASR are represented in Table 16, while the results obtained for NNHEA with ASNp and its mono-mutants are summarized in Table 17.

NNHEA Glucosylation Results

Firstly, it is observed that the enzymes α-1,2-BrS, α-1,3-BrS and ASR can glucosylate NNHEA and lead solely to the production of mono-glucosylated NNHEAs. Traces of di-glucosylated NNHEA were also detected.

For the purposes of the invention, the term "traces of a compound" means that this compound is present in a sample in an amount sufficient to be detected by a measuring method such as that used in the present examples, but in an amount that is too low to be able to be measured.

Similarly, the value 0 indicated in the tables of the present document means that the compound concerned is either absent or present in an amount that is so low that it cannot be detected by a measuring method such as that used in the present examples.

In addition, NNHEA can be glucosylated with wild-type ASNp, and also with 113 of its tested mono-mutants, as illustrated in Table 17.

In particular, 30 of them were seen to glucosylate NNHEA more efficiently than the parent wild-type enzyme, namely:

I228V, F229M, A289C, A289G, A289M, A289N, A289Q, A289S, A289T, A289V, F290A, F290C, F290G, F290I, F290K, F290L, F290M, F290Q, F290S, F290T, F290V, F290W, I330V, V331D, V331E, V331G, V331N, V331S, V331T and V331Y.

Example 10: Glycosylation of Acceptors Catalyzed with a Fructosyltransferase

In order to vary the nature of the sugar transferred onto the acceptors, the potential of a commercial fructosyltransferase was evaluated on HEMA, NHAM and HEAA (N-(hydro) ethylacrylamide), under conditions similar to those used previously with the glucan-saccharases.

These acceptors were thus fructosylated with *Bacillus subtilis* fructosyltransferase (see Table 1).

Results

The chromatograms obtained on Hypercarb and Amino columns, as described previously, after a fructosylation reaction using *B. Subtilis* fructosyltransferase, made it possible to observe fructosylation of all the tested acceptors.

More particularly, the total fructosylation observed is 32.5 mg/L for HEMA, 84.8 mg/L for HEAA and 21.1 mg/L for NHAM.

More particularly, whereas only mono-fructosylated HEMAs and NHAMs were obtained. HEAA was fructosylated 1, 4, 5, 6 and even 7 times. Insofar as these acceptors bear only one reactive hydroxyl group, only one type of each level of fructosylation of these molecules is obtained.

In addition, the sucrose consumption of the fructosyltransferase used and the levels of production (in g/L) of the fructosylated acceptors tested were measured.

It is observed that, in all the cases, more than 98% of the sucrose was consumed by the enzyme. In addition, the fructosylated HEAA production observed is 3 to 4 times higher than that observed with NHAM and HEMA.

Example 11: Study of the NNHEA Glucosylation Products of Example 9

The glucosylation products obtained in example 9 with some of the enzymes tested were analyzed more finely by LC-MS ($UV_{204}$ detection for NNHEA), according to the protocol indicated in example 1.

The results thus obtained are represented in Table 18.

Thus, NNHEA was very predominantly and exclusively mono-glucosylated by the enzymes tested, in particular by wild-type ASNp and its mutants A289Q, F290C, F290L and F290V, Traces of di-glucosylated NNHEA were also detected with the mono-mutants F290C, F290L and F290V.

The mutant F290W, for its part, made it possible to obtain both mono-glucosylated NNHEAs and di-glucosylated NNHEAs.

Example 12: Determination of the Efficiencies of Glucosylation of HEAA by Certain Enzymes of Example 1

The reactions in the presence of HEAA were performed by applying the conditions described in example 1.

These acceptor reactions were performed with a panel of three wild-type glycan-saccharases, namely: ASR, α-1,3-BrS and fructosyltransferase of *Bacillus subtilis* indicated in Table I.

One of the mono-mutants of the wild-type ASNp, the mono-mutant D394E, was also tested.

After reaction for 24 hours, the reaction medium is analyzed by HPLC-MS on a Hypercarb column (30 minutes) to identify the glucosylation products.

Table 19 shows the degree of sucrose conversion and the total glucosylation for each of these enzymes.

In addition, the glucosylation products obtained with ASR, α-1,3-BrS and the mono-mutant D394E of ASNp were analyzed more finely by LC-MS (UV$_{215}$ detection for HEAA), according to the protocol indicated in the preceding examples. The results obtained are indicated in Table 20.

Thus, ASR makes it possible to obtain mono-glycosylated HEAAs, di-glucosylated HEAAs and tri-glucosylated HEAAs.

In other similar experiments performed by the inventors, HEAAs glucosylated 4, 5, 6, 7 or 8 times were also able to be observed.

Conversely, α-1,3-BrS and the mono-mutant D394E of the wild-type ASNp make it possible to obtain only mono-glucosylated HEAAs. Only traces of di-glucosylated HEAAs were observed with these two enzymes.

TABLE 1

| Organism | Glycan-saccharase | References |
|---|---|---|
| *Neisseria polysaccharea* (EC 2.4.1.4) | ASNp WT and 171 single mutants of the active site (Positions 226, 228, 229, 289, 290, 330, 331, 394, 446) Glucan-saccharases | Potocki de Montalk et al, J. of Bacteriology. 1999, 181, 375-381<br>Champion E., 2008. Doctoral thesis. INSA. Toulouse<br>Champion C. et al., J. Am. Chem. Soc., 2009, 131, 7379-7389<br>Cambon E. et al., Biotechnol. Bioeng. 2014 Sep.; 111(9): 1719-28 |
| *Deinococcus geothermalis* | ASDg WT Glucan-saccharase | Emond et al., FEMS Microbiol. Lett. 2008 Aug.; 285(1): 25-32 |
| *Leuconostoc mesesnteroides* NRRL B-1355 | Truncated altemane-saccharase (ASR-C-del-bis or ASR) Glucan-saccharase | Joucla. G., 2003. Doctoral thesis, INSA. Toulouse<br>Joucla et al., FEBS Lett. 2006 Feb. 6; 580(3): 763-8 |
| *Leuconostoc mesesnteroides* B-512F | Truncated dextran-saccharase DSR-S vardel Δ4N (DSR-S-Δ4N) Glucan-saccharase | Moulis C., 2006. Doctoral thesis, INSA. Toulouse<br>Moulis C. et al., FEMS Microbiol. Lett., 2006 261 203-210 |
| *Leuconostoc mesesnteroides* NRRL B-1299 | Truncated dextran-sucrase DSR-E (GBD-CD2) Glucan-saccharase | WO/2002/074943<br>Brison et al, J. Biol. Chem., 2012. 287, 7915-24 |
| *Oenococcus kitaharae* DSM17330 | Dextran-saccharase (DSR-S-OK) Glucan-saccharase | FR1301402 |
| *Leuconostoc citreum* NRRL B-742 | α-1,3 BrS Glucan-saccharase | FR1301402 |
| *Leuconostoc citreum* NRRL B-1299 | α-1,2 BrS Glucan-saccharase | FR1301402 WO/2002/074943 |
| *Bacillus subtilis* NC1MB11871 | Fructosyltransferase | Cheetham et al., Enzyme Microb. Technol. 1989, 11, 212-219;<br>Baciu et al, Journal of Biotechnology, Volume 116, Issue 4, 6 Apr. 2005, Pages 347-357 |

TABLE 2

| HPLC Dionex U3000 (Thermo Scientific) | Hypercarb (6 min.) | Hypercarb (30 min.) | Amino (30 min) | C18 |
|---|---|---|---|---|
| Column Eluent Flow rate/ Temperature | Hypercarb 5 μm (100 × 2.1 mm)- Thermo ACN 10%/H2O 90% 0.5 ml/min; 8° C. | Hypercarb 5 μm (100 × 2.1 mm)- Thermo Gradient H2O-ACN 0.5 ml/min; 8° C. | Sperisorb Amino, 5 μm (250 × 4.0 mm)-Bischoff ACN 80%/H2O 20% 1 ml/min; 30° C. | C18 SB ZORBAX, 5 μm (250 × 4.6 mm)-Agilent Gradient H2O-ACN 1 ml/min; 30° C. |
| LC detection | ELSD (Evaporative light scattering detector) | UV$_{210/215\ nm}$ + ELSD | | UV$_{204\ nm}$ + ELSD |
| LC-MS detection | — | Positive electrospray ionization (ESI+); source at 450° C. Capillary voltage: 3kV: Cone voltage: 50 V | | |

TABLE 3

Ratio: sucrose 143 mM/ HEMA 438 mM

| Enzymes | Sucrose conversion (%) | HEMA glucosylation (g/L) | | | |
|---|---|---|---|---|---|
| | | Total glucosylation | HEMA-Glc1 | HEMA-Glc2 | HEMA-Glc3 |
| ASDg | 95.0 | 2.709 | 1.306 | 1.403 | 0 |
| ASR | 95.0 | 21.030 | 6.745 | 7.046 | 7.240 |
| GBD-CD2 | 23.7 | 2.168 | 2.168 | 0 | 0 |
| DSR-S-Δ4N | 39.0 | 0 | 0 | 0 | 0 |
| DSR-OK | 29.0 | 0 | 0 | 0 | 0 |
| α-1,2-BrS | 93.2 | 10.635 | 10.421 | 0.215 | 0 |
| α-1,3-BrS | 84.4 | 13.486 | 12.628 | 0.858 | 0 |

TABLE 4

Ratio: sucrose 143 mM/ 438 NHAM nM

| Enzymes | Sucrose conversion (%) | NHAM glucosylation (g/L) | | | |
|---|---|---|---|---|---|
| | | Total glucosylation | NHAM-Glc1 | NHAM-Glc2 | NHAM-Glc3 |
| ASDg | 12 | 0.136 | 0.136 | 0 | 0 |
| ASR | >95 | 0.340 | 0.135 | 0.205 | 0 |
| GBD-CD2 | 42 | 2.201 | 1.517 | 0.684 | 0 |
| DSR-S-Δ4N | 60 | 0.062 | 0.062 | 0 | 0 |
| DSR-OK | >95 | 0.149 | 0.149 | 0 | 0 |
| α-1,2-BrS | >95 | 1.886 | 1.781 | 0.054 | 0.050 |
| α-1,3-BrS | >95 | 2.078 | 1.918 | 0.160 | 0 |

TABLE 5

ASNp WT = 0.079 g/L
Positive mutants

| HEMA | | estimated production in g/L | | | | | | | | | |
|---|---|---|---|---|---|---|---|---|---|---|---|
| | | A | C | D | E | F | G | H | I | K | L |
| Mutated positions | R226 | 0.076 | 0.101 | 0 | 0 | 0 | 0 | 0 | 0 | 0 | 0 |
| | I228 | 0 | 0 | 0 | 0 | 0 | 0 | 0 | | 0 | 0 |
| | F229 | 0 | 0 | 0 | 0 | | 0 | 0 | 0 | 0 | 0 |
| | A289 | | 0 | 0 | 0 | 0 | 0 | 0.127 | 0.039 | 0.045 | 0.139 |
| | F290 | 4.532 | 8.966 | 0 | 0 | 0 | 0 | 0.013 | 3.134 | 0.795 | 2.152 |
| | I330 | 0.287 | 0.022 | 0 | 0.014 | 0.042 | 0.040 | 0.011 | | 0.008 | 0.008 |
| | V331 | 0.010 | 0.103 | 0.234 | 0.444 | 0.026 | 0.098 | 0.108 | 0 | 0.046 | 0.023 |
| | D394 | 0.236 | 0.049 | | 0.012 | 0 | 0.065 | 0.019 | 0.024 | 0 | 0.030 |
| | R446 | 0.019 | 0.157 | 0.007 | 0.019 | 0.021 | 0.136 | 0.013 | 0.029 | 0.089 | 0.118 |

ASNp WT = 0.079 g/L
Positive mutants

| HEMA | | estimated production in g/L | | | | | | | | | |
|---|---|---|---|---|---|---|---|---|---|---|---|
| | | M | N | P | Q | R | S | T | V | W | Y |
| Mutated positions | R226 | 0 | 0.008 | 0.006 | 0 | | 0.009 | 0.006 | 0 | 0 | 0 |
| | I228 | 0 | 0 | 0.041 | 0 | 0 | 0 | 0.099 | 0.014 | 0 | 0 |
| | F229 | 0 | 0 | 0 | 0 | 0 | 0 | 0 | 0 | 0.121 | 0 |
| | A289 | 0.007 | 0 | 0 | 0 | 0 | 0 | 0 | 0 | 0.015 | 0 |
| | F290 | 0.793 | 0.014 | 0.139 | 0.075 | 0 | 0 | 0 | 5.938 | 0.004 | 0 |
| | I330 | 0.033 | 0.052 | 0 | 0 | 0 | 0 | 0 | 0 | 0 | 0 |
| | V331 | 0.023 | 0 | 0 | 0 | 0 | 0 | 0 | 0 | 0 | 0 |
| | D394 | 0.030 | 0.038 | 0 | 0 | 0 | 0 | 0 | 0 | 0 | 0 |
| | R446 | 0.039 | 0.257 | 0 | 0 | 0 | 0 | 0 | 0 | 0 | 0 |

TABLE 6

ASNp WT = 0.026 g/L
Positive mutants estimated production in g/L

| NHAM | | A | C | D | E | F | G | H | I | K | L |
|---|---|---|---|---|---|---|---|---|---|---|---|
| Mutated positions | R226 | 0.003 | 0.003 | 0.003 | 0.004 | 0.004 | 0.003 | 0.004 | 0.003 | 0.003 | 0.003 |
| | I228 | 0 | 0.008 | 0 | 0.003 | 0 | 0 | 0 | 0 | 0 | 0.019 |
| | F229 | 0.006 | 0.010 | 0 | 0 | 0 | 0 | 0 | 0.004 | 0 | 0.007 |
| | A289 | | 0.021 | 0.005 | 0.004 | 0.002 | 0.019 | 0.022 | 0.008 | 0 | 0.002 |
| | F290 | 0.002 | 0.003 | 0 | 0 | | 0.002 | 0 | 0 | 0 | 0.002 |
| | I330 | 0.001 | 0 | 0 | 0 | 0 | 0 | 0 | 0 | 0 | 0 |
| | V331 | 0.024 | 0.031 | 0.039 | 0.097 | 0.001 | 0.025 | 0.008 | 0.002 | 0 | 0.014 |
| | D394 | 0 | 0.001 | | 0.137 | 0 | 0.009 | 0 | 0 | 0 | 0 |
| | R446 | 0.004 | 0.013 | 0 | 0 | 0.001 | 0.012 | 0 | 0 | 0.007 | 0.001 |

ASNp WT = 0.026 g/L
Positive mutants estimated production in g/L

| NHAM | | M | N | P | Q | R | S | T | V | W | Y |
|---|---|---|---|---|---|---|---|---|---|---|---|
| Mutated positions | R226 | 0.001 | 0.004 | 0 | 0.003 | | 0.002 | 0.003 | 0.002 | 0.003 | 0.003 |
| | I228 | 0.020 | 0.014 | 0.003 | 0.009 | 0.001 | 0 | 0.001 | 0.016 | 0 | 0.002 |
| | F229 | 0.130 | 0.051 | 0.002 | 0.003 | 0 | 0 | 0 | 0.012 | 0.003 | 0.011 |
| | A289 | 0.019 | 0.126 | 0.032 | 0.037 | 0 | 0.026 | 0.020 | 0.026 | 0 | 0 |
| | F290 | 0.006 | 0.009 | 0.002 | 0.003 | 0 | 0 | 0 | 0.007 | 0.015 | 0.019 |
| | I330 | 0.006 | 0.033 | 0 | 0 | 0 | 0 | 0 | 0.016 | 0 | 0 |
| | V331 | 0.005 | 0.028 | 0.001 | 0.025 | 0.001 | 0.019 | 0.031 | | 0 | 0.018 |
| | D394 | 0 | 0.004 | 0 | 0 | 0 | 0 | 0 | 0 | 0 | 0 |
| | R446 | 0.002 | 0.013 | 0 | 0.006 | | 0.012 | 0.007 | 0 | 0 | 0.001 |

TABLE 7

Ratio: sucrose 73 mM/ HEMA 73 mM

| | Sucrose | HEMA glucosylation (g/L) | | | |
|---|---|---|---|---|---|
| Enzymes | conversion (%) | Total glucosylation | HEMA-Glc1 | HEMA-Glc2 | HEMA-Glc3 |
| Wild-type ASNp | 87 | 0.141 | 0.079 | 0.062 | Traces |
| F229W | 92.5 | 0.121 | 0.069 | 0.052 | 0 |
| F290A | 73.5 | 4.532 | 1.961 | 0.486 | 2.084 |
| F290C | 83 | 8.966 | 6.064 | 1.734 | 1.167 |
| F290I | 69 | 3.134 | 2.377 | 0.420 | 0.337 |
| F290K | 57 | 0.795 | 0.616 | 0.179 | Traces |
| F290L | 92 | 2.197 | 1.531 | 0.621 | 0.045 |
| F290M | 92 | 0.793 | 0.544 | 0.249 | Traces |
| F290V | 40 | 5.938 | 4.535 | 0.704 | 0.699 |
| I330A | 4 | 0.287 | 0.188 | 0.099 | 0 |
| V331E | 88 | 0.444 | 0.299 | 0.145 | 0 |
| D394A | 23 | 0.236 | 0.149 | 0.087 | 0 |
| R446G | 14.5 | 0.191 | 0.094 | 0.041 | 0.055 |

TABLE 8

Ratio: sucrose 73 mM/ NHAM 73 mM

| | Sucrose | NHAM glucosylation (g/L) | | | |
|---|---|---|---|---|---|
| Enzymes | conversion (%) | Total glucosylation | NHAM-Glc1 | NHAM-Glc2 | NHAM-Glc3 |
| Wild-type ASNp | 76.5 | 0.101 | 0.025 | 0.076 | 0 |
| F229M | 73.7 | 0.169 | 0.130 | 0.033 | 0.007 |
| F229N | 2.5 | 0.100 | 0.051 | 0.049 | 0 |
| A289N | 90.8 | 0.211 | 0.126 | 0.084 | 0 |
| A289P | 81.0 | 0.127 | 0.032 | 0.096 | 0 |

TABLE 8-continued

Ratio: sucrose 73 mM/ NHAM 73 mM

| | Sucrose | NHAM glucosylation (g/L) | | | |
|---|---|---|---|---|---|
| Enzymes | conversion (%) | Total glucosylation | NHAM-Glc1 | NHAM-Glc2 | NHAM-Glc3 |
| A289Q | 52.1 | 0.083 | 0.037 | 0.045 | 0 |
| I330N | 0.6 | 0.096 | 0.033 | 0.063 | 0 |
| V331C | 75.0 | 0.065 | 0.031 | 0.029 | 0.004 |
| V331D | 17.7 | 0.077 | 0.039 | 0.032 | 0.007 |
| V331E | 64.2 | 0.145 | 0.097 | 0.038 | 0.010 |
| V331T | 86.9 | 0.100 | 0.031 | 0.069 | 0 |
| D394E | 86.6 | 0.187 | 0.137 | 0.050 | 0 |

TABLE 9

| Acceptor | Enzyme | Volume | Lyophilized | g/L | Estimated production (g) |
|---|---|---|---|---|---|
| HEMA | F290C | 500 | yes | 38.8 | 19.4 |
| | ASR | 500 | yes | 29.7 | 14.8 |
| | α-1,3-BrS | 500 | yes | 15.1 | 7.5 |
| NHAM | D394E | 500 | yes | 1 | 0.5 |
| | ASR | 500 | no | 1 | 0.5 |
| | α-1,3-BrS | 500 | yes | 2.5 | 1.25 |

TABLE 10

| Ratio: sucrose 143 mM/2-propen-ol 438 mM Enzymes | Allyl alcohol glucosylation (g/L) | |
|---|---|---|
| | Sucrose conversion (%) | Total glucosylation |
| ASDg | 82.6 | 0.166 |
| ASR | 91.5 | 0 |
| GBD-CD2 | 46.3 | 1.225 |
| DSR-S-Δ4N | 76.1 | 0 |
| DSR-OK | 97.4 | 0 |
| α-1,2-BrS | 88.8 | 1.908 |
| α-1,3-BrS | 76.6 | 1.207 |

TABLE 11

| Ratio: sucrose 143 mM/BME 438 mM Enzymes | BME glucosylation (g/L) | |
|---|---|---|
| | Sucrose conversion (%) | Total glucosylation |
| ASDg | 80.4 | 1.849 |
| ASR | 91.3 | 0 |
| GBD-CD2 | 3.0 | 1.674 |
| DSR-S-Δ4N | 5.5 | 0 |
| DSR-OK | 97.2 | 0 |
| α-1,2-BrS | 89.1 | 2.848 |
| α-1,3-BrS | 81.9 | 2.736 |

TABLE 12

ASNp WT = 0.619 g/L
Positive mutants

| Allyl Alcohol | | A | C | D | E | F | G | H | I | K | L |
|---|---|---|---|---|---|---|---|---|---|---|---|
| Mutated positions | R226 | 0.313 | 0.252 | 0.127 | 0.207 | 0.184 | 0.065 | 0.061 | 0.356 | 0.154 | 0.13 |
| | I228 | 0 | 0 | 0.35 | 0.352 | 0.279 | 0.57 | 0.888 | | 0 | 0 |
| | F229 | 0 | 0.408 | 0.649 | 0.966 | | 0.684 | 0.619 | 0.851 | 0.799 | 0.6 |
| | A289 | | 0.852 | 0.697 | 0.816 | 0.783 | 0.785 | 0.881 | 0.77 | 0.763 | 0.681 |
| | F290 | 0.538 | 1.052 | 0.825 | 0.89 | | 0.852 | 1.105 | 0.763 | 0.82 | 0.787 |
| | I330 | 0.568 | 1.004 | 0.929 | 0.792 | 0.852 | 0.994 | 0.858 | | 0.707 | 0.73 |
| | V331 | 0.413 | 0.707 | 0.778 | 0.728 | 0.772 | 0.703 | 0.849 | 0.778 | 0.737 | 0.705 |
| | D394 | 0.302 | 0.455 | | 1.018 | 0.707 | 0.806 | 0.686 | 0.756 | 0.777 | 0.659 |
| | R446 | 0.37 | 0.36 | 0.394 | 0.477 | 0.47 | 0.548 | 0.451 | 0.508 | 0.371 | 0.394 |

ASNp WT = 0.619 g/L
Positive mutants

| Allyl Alcohol | | M | N | P | Q | R | S | T | V | W | Y |
|---|---|---|---|---|---|---|---|---|---|---|---|
| Mutated positions | R226 | 0.042 | 0.16 | 0.19 | 0.15 | | 0.092 | 0.197 | 0.117 | 0 | 0.177 |
| | I228 | 0 | 0 | 0.274 | 0.366 | 0.421 | 0.383 | 0.277 | 0.312 | 0.404 | 0.53 |
| | F229 | 0.626 | 0 | 0.338 | 0.413 | 0.45 | 0.412 | 0.511 | 0.571 | 0.524 | 0.545 |
| | A289 | 0.803 | 0 | 0.517 | 0.499 | 0.54 | 0.432 | 0.591 | 0.409 | 0.654 | 0.648 |
| | F290 | 0.999 | 0 | 0.37 | 0.442 | 0.525 | 0.437 | 0.5 | 0.573 | 0.649 | 0.572 |
| | I330 | 0.734 | 0.495 | 0.326 | 0.509 | 0.598 | 0.799 | 0.463 | 0.593 | 0.427 | 0.701 |
| | V331 | 0.578 | 0.647 | 0.265 | 0.385 | 0.467 | 0.598 | 0.519 | | 0.626 | 0.486 |
| | D394 | 0.497 | 0 | 0.155 | 0.327 | 0.402 | 0.51 | 0.417 | 0.277 | 0.478 | 0.411 |
| | R446 | 1.112 | 0 | 0 | 0.477 | | 0.205 | 0.325 | 0.292 | 0.315 | 0.318 |

TABLE 13

ASNp WT = 0.021 g/L
Positive mutants

| BME | | A | C | D | E | F | G | H | I | K | L |
|---|---|---|---|---|---|---|---|---|---|---|---|
| Mutated positions | R226 | 0 | 0 | 0 | 0 | 0 | 0 | 0 | 0 | 0 | 0 |
| | I228 | 0.004 | 0 | 0 | 0.011 | 0.009 | 0 | 0.06 | | 0 | 0.027 |
| | F229 | 0.009 | 0.051 | 0 | 0 | | 0 | 0 | 0.012 | 0 | 0.014 |
| | A289 | | 0.139 | 0.174 | 0.102 | 1.217 | 0.081 | 0.039 | 0.026 | 0 | 0 |
| | F290 | 0.085 | 0.081 | 0.158 | 0.045 | | 0.030 | 0.017 | 0.027 | 0.021 | 0.014 |
| | I330 | 0.012 | 0 | 0 | 0 | 0 | 0 | 0 | | 0 | 0 |
| | V331 | 0.099 | 0.299 | 0.191 | 0.367 | 0.265 | 0.072 | 0.069 | 0.026 | 0.010 | 0.014 |
| | D394 | 0.018 | 0 | | 0.025 | 0 | 0 | 0 | 0 | 0 | 0 |
| | R446 | 0.012 | 0.004 | 0 | 0 | 0 | 0 | 0 | 0 | 0 | 0 |

TABLE 13-continued

ASNp WT = 0.021 g/L
Positive mutants

| BME | | estimated production in g/L | | | | | | | | | |
|---|---|---|---|---|---|---|---|---|---|---|---|
| | | M | N | P | Q | R | S | T | V | W | Y |
| Mutated positions | R226 | 0 | 0 | 0 | 0 | | 0 | 0 | 0 | 0 | 0 |
| | I228 | 0.016 | 0.004 | 0 | 0.012 | 0.009 | 0 | 0 | 0.036 | 0.045 | 0.023 |
| | F229 | 0.050 | 0 | 0.024 | 0.021 | 0.010 | 0 | 0 | 0.068 | 0.005 | 0.104 |
| | A289 | 0.461 | 0.376 | 0.343 | 0.757 | 0.040 | 0.366 | 0.320 | 0.180 | 0.100 | 0 |
| | F290 | 0.037 | 0 | 0.030 | 0.284 | 0.010 | 0.420 | 0.472 | 0.062 | 0.491 | 0.009 |
| | I330 | 0 | 0.012 | 0 | 0.058 | 0 | 0.012 | 0.020 | 0.032 | 0.012 | 0 |
| | V331 | 0 | 0.142 | 0 | 0.042 | 0.237 | 0.248 | 0.458 | | 0.366 | 0.255 |
| | D394 | 0 | 0 | 0 | 0 | 0 | 0.005 | 0 | 0 | 0 | 0 |
| | R446 | 0 | 0 | 0 | 0.016 | | 0.030 | 0.005 | 0 | 0 | 0 |

TABLE 14

| Ratio: sucrose 73 mM/ VBA 73 mM | VBA glucosylation | |
|---|---|---|
| Enzymes | Sucrose conversion (%) | Total glucosylation (g/L) |
| α-1,2-BrS | 63.1 | 7.9 |
| ASR | 95.3 | 2.5 |

TABLE 15

ASNp WT = 0.5 g/L
Positive mutants

| VBA | | estimated production in g/L | | | | | | | | | | | | | | | | | | | |
|---|---|---|---|---|---|---|---|---|---|---|---|---|---|---|---|---|---|---|---|---|---|
| | | A | C | D | E | F | G | H | I | K | L | M | N | P | Q | R | S | T | V | W | Y |
| Mutated positions | R226 | 0 | 0 | 0 | 0 | 0 | 0 | 1.2 | 0 | 0.6 | 0 | 0.7 | 1.9 | 0 | 0.7 | | 0.5 | 0.9 | 0.6 | 0 | 0.3 |
| | I228 | 0 | 0 | 0 | 0 | 0 | 0 | 0 | | 0 | 0 | 0 | 0 | 0 | 0 | 0 | 0 | 0 | 2.1 | 0 | 0 |
| | F229 | 0 | 0 | 0 | 0 | | 0 | 0 | 0 | 0 | 0 | 0 | 0 | 0 | 0 | 0 | 0 | 0 | 0 | 0 | 0 |
| | A289 | | 0 | 0 | 0 | 0 | 0 | 0 | 0 | 0 | 0 | 3.0 | 5.7 | 10.9 | 9.9 | 0 | 14.2 | 6.2 | 1.5 | 0 | 0 |
| | F290 | 0 | 0 | 0 | 0 | | 0 | 0 | 0 | 0 | 0 | 0 | 0 | 0 | 0 | 0 | 0 | 0 | 2.2 | 1.1 | 0 |
| | I330 | 0 | 0 | 0 | 0 | 0 | 0 | 0 | | 0 | 0 | 0 | 0 | 0 | 0 | 0 | 0 | 0 | 0 | 0 | 0 |
| | V331 | | 6 | 1.5 | 0 | 0 | 4.1 | 0 | 0 | 0 | 0 | 0 | 0 | 0 | 0 | 0 | 4.3 | 5.3 | | 0 | 3.0 |
| | D394 | 0 | 0 | | 0 | 0 | 0 | 0 | 0 | 0 | 0 | 0 | 0 | 0 | 0 | 0 | 0 | 0 | 0 | 0 | 0 |
| | R446 | 14.6 | 0 | 0 | 0 | 0 | 0 | 0 | 0 | 0 | 0 | 0 | 0 | 0 | 0 | | 0 | 0 | 0 | 0 | 0 |

TABLE 16

Ratio: sucrose 73 mM/ NNHEA 73 mM

| | Sucrose conversion (%) | NNHEA glucosylation (g/L) | | | |
|---|---|---|---|---|---|
| Enzymes | | Total glucosylation | NNHEA-Glc1 | NNHEA-Glc2 | NNHEA-Glc3 |
| ASR | >98 | 0.86 | 0.86 | Traces | 0 |
| α-1,2-BrS | 90 | 1.76 | 1.76 | Traces | 0 |
| α-1,3-BrS | >98 | 1.47 | 1.47 | Traces | 0 |

TABLE 17

ASNp WT = 1.64 g/L
Positive mutants estimated production in g/L

| | NNHEA | A | C | D | E | F | G | H | I | K | L |
|---|---|---|---|---|---|---|---|---|---|---|---|
| Mutated positions | R226 | 0.6 | 0 | 0.07 | 0.89 | 0 | 0 | 0 | 0.81 | 0.59 | 0.62 |
| | I228 | 0.49 | 0.75 | 0 | 0.05 | 0.07 | 0 | 0.96 | 0 | 0 | 0.71 |
| | F229 | 0 | 0.3 | 0 | 0 | | 0 | 0 | 0.51 | 0 | 0.52 |
| | A289 | | 2.31 | 1.2 | 0.66 | 0.13 | 1.77 | 0.34 | 1.46 | 0.09 | 0.25 |
| | F290 | 2.03 | 7.17 | 0.41 | 1.46 | | 2.41 | 0.4 | 2.73 | 1.91 | 6.58 |
| | I330 | 0 | 0.08 | 0 | 0 | 0 | 0 | 0 | | 0.05 | 0 |
| | V331 | 0 | 0.4 | 2.05 | 2.33 | 0.46 | 1.88 | 1.44 | 0.74 | 0.06 | 0.88 |
| | D394 | 0 | 0 | | 0.31 | 0 | 0.3 | 0 | 0 | 0 | 0 |
| | R446 | 0 | 0.59 | 0 | 0 | 0.11 | 0.31 | 0 | | 0.4 | 0.13 |

ASNp WT = 1.64 g/L
Positive mutants estimated production in g/L

| | NNHEA | M | N | P | Q | R | S | T | V | W | Y |
|---|---|---|---|---|---|---|---|---|---|---|---|
| Mutated positions | R226 | 0.65 | 0.78 | 0 | 0.29 | | 0.73 | 0.77 | 0.66 | 0.49 | 0.56 |
| | I228 | 1.02 | 0.31 | 0.61 | 0.63 | 0 | 0.07 | 0.61 | 1.99 | 0.08 | 0.6 |
| | F229 | 1.66 | 0.2 | 0 | 0.02 | 0.04 | 0 | 0 | 0.51 | 0.67 | 1.5 |
| | A289 | 0.88 | 2.61 | 0.85 | 5.11 | 0.18 | 2.59 | 2.49 | 2.06 | 1.19 | 0 |
| | F290 | 2.85 | 0 | 0.84 | 1.81 | 1.54 | 2.34 | 2.55 | 8.99 | 5.28 | 0.62 |
| | I330 | 1.1 | 0 | 0 | 0.12 | 0 | 0 | 0.07 | 1.66 | 0 | 0.04 |
| | V331 | 0.66 | 1.93 | 0 | 0 | 0.14 | 2.15 | 2.37 | | 0.38 | 2.04 |
| | D394 | 0 | 0 | 0 | 0 | 0.02 | 0.16 | 0 | 0 | 0 | 0 |
| | R446 | 0.28 | 0.37 | 0 | 0.36 | | 0.25 | 0.49 | 0 | 0 | 0.24 |

TABLE 18

Ratio: sucrose 73 mM/NNHEA 73 mM

| Enzymes | Sucrose conversion (%) | NNHEA glucosylation (g/L) | | | |
|---|---|---|---|---|---|
| | | Total glucosylation | NNHEA-Glc1 | NNHEA-Glc2 | NNHEA-Glc3 |
| Wild-type ASNp | 98 | 1.7 | 1.7 | 0 | 0 |
| A289Q | 99 | 5.1 | 5.1 | 0 | 0 |
| F290C | 69 | 7.2 | 7.2 | Traces | 0 |
| F290L | 89 | 6.6 | 6.6 | Traces | 0 |
| F290V | 99 | 9.0 | 9.0 | Traces | 0 |
| F290W | 68 | 5.3 | 3.0 | 2.3 | 0 |

TABLE 19

Ratio: sucrose 146 mM/HEAA 438 mM

| Enzymes | Sucrose conversion (%) | HEAA glucosylation (g/L) Total glucosylation |
|---|---|---|
| ASR | 92 | 2.8 |
| α-1,3-BrS | 97 | 2.4 |
| D394E | 81 | 3.9 |
| *Bacillus subtilis* fructosyltransferase of Table I | 99.2 | 0.08 |

TABLE 20

Ratio: sucrose 146 mM/HEAA 348 mM

| Enzymes | Sucrose conversion (%) | HEAA glucosylation (g/L) | | | |
|---|---|---|---|---|---|
| | | Total glucosylation | HEAA-Glc1 | HEAA-Glc2 | HEAA-Glc3 |
| ASR | 92 | 2.823 | 0.851 | 1.54 | 0.431 |
| α-1,3-BrS | 97 | 2.441 | 2.441 | Traces | 0 |
| D394E | 81 | 3.883 | 3.883 | Traces | 0 |

SEQUENCES:

Series SEQ ID NO: 1: (Protein = sequence of the wild-type glucan saccharase ASNp (Amylosucrase of Neisseria polysaccharea))
SPNSQYLKTRILDIYTPEQRAGIEKSEDWRQFSRRMDTHFPKLMNELDSVYGNNEALLPMLEMLLAQAWQSYSQR
NSSLKDIDIARENNPDWILSNKQVGGVCYVDLFAGDLKGLKDKIPYFQELGLTYLHLMPLFKCPEGKSDGGYAVS
SYRDVNPALGTIGDLREVIAALHEAGISAVVDFIFNHTSNEHEWAQRCAAGDPLFDNFYYIFPDRRMPDQYDRTL
REIFPDQHPGGFSQLEDGRWVWTTFNSFQWDLNYSNPWVFRAMAGEMLFLANLGVDILRMDAVAFIWKQMGTSCE
NLPQAHALIRAFNAVMRIAAPAVFFKSEAIVHPDQVVQYIGQDECQIGYNPLQMALLWNTLATREVNLLHQALTY
RHNLPEHTAWVNYVRSHDDIGWTFADEDAAYLGSIGYDHRQFLNRFFVNRFDGSFARGVPFQYNPSTGDCRVSGT -continued

SEQUENCES:

AAALVGLAQDDPHAVDRIKLLYSIALSTGGLPLIYLGDEVGTLNDDDWSQDSNKSDDSRWAHRPRYNEALYAQRN
DPSTAAGQIYQDRLHMIAVRQSNPRFDGGLRVTFNTNNKHIIGYIRNNALLAFGNFSEYPQTVTAHTLQAMPFKA
HDLIGGKTVSLNQDLTLQPYQVMWLEIA

Series SEQ ID NO: 2: (Proteins = mutated sequences of glucan-saccharase ASNp (Amylosucrase of *Neisseria polysaccharea*) R226$X_1$)
SPNSQYLKTRILDIYTPEQRAGIEKSEDWRQFSRRMDTHFPKLMNELDSVYGNNEALLPMLEMLLAQAWQSYSQR
NSSLKDIDIARENNPDWILSNKQVGGVCYVDLFAGDLKGLKDKIPYFQELGLTYLHLMPLFKCPEGKSDGGYAVS
SYRDVNPALGTIGDLREVIAALHEAGISAVVDFIFNHTSNEHEWAQRCAAGDPLFDNFYYIFPDRRMPDQYDRTL
X$_1$EIFPDQHPGGFSQLEDGRWVWTTFNSFQWDLNYSNPWVFRAMAGEMLFLANLGVDILRMDAVAFIWKQMGTSC
ENLPQAHALIRAFNAVMRIAAPAVFFKSEAIVHPDQVVQYIGQDECQIGYNPLQMALLWNTLATREVNLLHQALT
YRHNLPEHTAWVNYVRSHDDIGWTFADEDAAYLGISGYDHRQFLNRFFVNRFDGSFARGVPFQYNPSTGDCRVSG
TAAALVGLAQDDPHAVDRIKLLYSIALSTGGLPLIYLGDEVGTLNDDDWSQDSNKSDDSRWAHRPRYNEALYAQR
NDPSTAAGQIYQDLRHMAIVRQSNPRFDGGRLVTFNTNNKHIIGYIRNNALLAFGNFSEYPQTVTAHTLQAMPFK
AHDLIGGKTVSLNQDLTLQPYQVMWLEIA Series SEQ ID NO: 3: (Proteins = mutated sequences of glucan-saccharase ASNp (Amylosucrase of *Neisseria polysaccharea*) I228$X_2$)
SPNSQYLKTRILDIYTPEQRAGIEKSEDWRQFSRRMDTHFPKLMNELDSVYGNNEALLPMLEMLLAQAWQSYSQR
NSSLKDIDIARENNPDWILSNKQVGGVCYVDLFAGDLKGLKDKIPYFQELGLTYLHLMPLFKCPEGKSDGGYAVS
SYRDVNPALGTIGDLREVIAALHEAGISAVVDFIFNHTSNEHEWAQRCAAGDPLFDNFYYIFPDRRMPDQYDRTL
REX$_2$FPDQHPGGFSQLEDGRWVWTTFNSFQWDLNYSNPWVFRAMAGEMLFLANLGVDILRMDAVAFIWKQMGTSC
ENLPQAHALIRAFNAVMRIAAPAVFFKSEAIVHPDQVVQYIGQDECQIGYNPLQMALLWNTLATREVNLLHQALT
YRHNLPEHTAWVNYVRSHDDIGWTFADEDAAYLGISGYDHRQFLNRFFVNRFDGSFARGVPFQYNPSTGDCRVSG
TAAALVGLAQDDPHAVDRIKLLYSIALSTGGLPLIYLGDEVGTLNDDDWSQDSNKSDDSRWAHRPRYNEALYAQR
NDPSTAAGQIYQDLRHMIAVRQSNPRFDGGRLVTFNTNNKHIIGYIRNNALLAFGNFSEYPQTVTAHTLQAMPFK
AHDLIGGKTVSLNQDLTLQPYQVMWLEIA Series SEQ ID NO: 4: (Proteins = mutated sequences of glucan-saccharase ASNp (Amylosucrase of *Neisseria polysaccharea*) F229$X_3$)
SPNSQYLKTRILDIYTPEQRAGIEKSEDWRQFSRRMDTHFPKLMNELDSVYGNNEALLPMLEMLLAQAWQSYSQR
NSSLKDIDIARENNPDWILSNKQVGGVCYVDLFAGDLKGLKDKIPYFQELGLTYLHLMPLFKCPEGKSDGGYAVS
SYRDVNPALGTIGDLREVIAALHEAGISAVVDFIFNHTSNEHEWAQRCAAGDPLFDNFYYIFPDRRMPDQYDRTL
REIX$_3$PDQHPGGFSQLEDGRWVWTTFNSFQWDLNYSNPWVFRAMAGEMLFLANLGVDILRMDAVAFIWKQMGTSC
ENLPQAHALIRAFNAVMRIAAPAVFFKSEIAVHPDQVVQYIGQDECQIGYNPLQMALLWNTLATREVNLLHQALT
YRHNLPEHTAWVNYVRSHDDIGWTFADEDAAYLGISGYDHRQFLNRFFVNRFDGSFARGVPFQYNPSTGDCRVSG
TAAALVGLAQDDPHAVDRIKLLYSIALSTGGLPLIYLGDEVGTLNDDDWSQDSNKSDDSRWAHRPRYNEALYAQR
NDPSTAAGQIYQDLRHMIAVRQSNPRFDGGRLVTFNTNNKHIIGYIRNNALLAFGNFSEYPQTVTAHTLQAMPFK
AHDLIGGKTVSLNQDLTLQPYQVMWLEIA SEQ ID NO: 5: (Protein = mutated sequences of glucan-saccharase ASNp (Amylosucrase of *Neisseria polysaccharea*) A289$X_4$)
SPNSQYLKTRILDIYTPEQRAGIEKSEDWRQFSRRMDTHFPKLMNELDSVTGNNEALLPMLEMLLAQAWQSYSQR
NSSLKDIDIARENNPDWILSNKQVGGVCYVDLFAGDLKGLKDKIPYFQELGLTYLHLMPLFKCPEGKSDGGYAVS
SYRDVNPALGTIGDLREVIAALHEAGISAVVDFIFNHTSNEHEWAQRCAAGDPLFDNFYYIFPDRRMPDQYDRTL
REIFPDQHPGGFSQLEDGRWVWTTFNSFQWDLNYSNPWVFRAMAGEMLFLANLGVDILRMDAVX$_4$FIWKQMGTSC
ENLPQAHALIRAFNAVMRIAAPAVFFKSEAIVHPDQVVQYIGQDECQIGYNPLQMALLWNTLATREVNLLHQALT
YRHNLPEHTAWVNYVRSHDDIGWTFADEDAAYLGISGYDHRQFLNRFFVNRFDGSFARGVPFQUNPSTGDCRVSG
TAAALVGLAQDDPHAVDRIKLLYSIALSTGGLPLIYLGDEVGTLNDDDWSQDSNKSDDSRWAHRPRYNEALYAQR
NDPSTAAGQIYQDLRHMIAVRQSNPRFDGGRLVTFNTNNKHIIGYIRNNALLAFGNFSEYPQTVTAHTLQAMPFK
AHDLIGKGTVSLNQDLTLQPYQVMWLEIA Series SEQ ID NO: 6: (Proteins = mutated sequences of glucan-saccharase ASNp (Amylosucrase of *Neisseria polysaccharea*) F290$X_5$)
SPNQSYLKTRILDIYTPEQRAGIEKSEDWRQFSRRMDTHFPKLMNELDSVYGNNEALLPMLEMLLAQAWQSYSQR
NSSLKDIDIARENNPDWILSNKQVGGVCYVDLFAGDLKGLKDKIPYFQELGLTYLHLMPLFKCPEGKSDGGYAVS
SYRDVNPALGTIGDLREVIAALHEAGISAVVDFIFNHTSNEHEWAQRCAAGDPLFDNFYYIFPDRRMPDQYDRTL
REIFPDQHPGGFSQLEDGRWVWTTFNSFQWDLNYSNPWVFRAMAGEMLFLANLGVDILRMDAVAX$_5$IWKQMGTSC
ENLPQAHALIRAFNAVMRIAAPAVFFKSEAIVHPDQVVQYIGQDECQIGYNPLQMALLWNTLATREVNLLHQALT
YRHNLPEHTAWVNYVRSHDDIGWTFADEDAAYLGISGYDHRQFLNRFFVNRFDGSFARGVPFQYNPSTGDCRVSG
TAAALVGLAQDDPHAVDRIKLLYSIALSTGGLPLIYLGDEVGTLNDDDWSQDSNKSDDSRWAHRPRYNEALYAQR
NDPSTAAGQIYQDLRHMIAVRQSNPRFDGGRLVTFNTNNKHIIGYIRNNALLAFGNFSEYPQTVTAHTLQAMPFK
AHDLIGGKTVSLNQDLTLQPYQVMWLEIA Series SEQ ID NO: 7: (Proteins = mutated sequences of glucan-saccharase ASNp (Amylosucrase of *Neisseria polysaccharea*) I330$X_6$)
SPNSQYLKTRILDIYTPEQRAGIEKSEDWRQFSRRMDTHFPKLMNELDSVYGNNEALLPMLEMLLAQAWQSYSQR
NSSLKDIDIARENNPDWILSNKQVGGVCYVDLFAGDLKGLKDKIPYFQELGLTYLHLMPLFKCPEGKSDGGYAVS
SYRDVNPALGTIGDLREVIAALHEAGISAVVDFIFNHTSNEHEWAQRCAAGDPLFDNFYYIFPDRRMPDQYDRTL
REIFPDQHPGGFSQLEDGRWVWTTFNSFQWDLNYSNPWVFRAMAGEMLFLANLGVDILRMDAVAFIWKQMGTSCE
NLPQAHALIRAFNAVMRIAAPAVFFKSEAX$_6$VHPDQVVQYIGQDECQIGYNPLQMALLWNTLATREVNLLHQALT
YRHNLPEHTAWVNYVRSHDDIGWTFADEDAAYLGISGYDHRQFLNRFFVNRFDGSFARGVPFQYNPSTGDCRVSG
TAAALVGLAQDDPHAVDRIKLLYSIALSTGGLPLIYLGDEVGTLNDDDWSQDSNKSDDSRWAHRPRYNEALYAQR
NDPSTAAGQIYQDLRHMIAVRQSNPRFDGGRLVTFNTNNKHIIGYIRNNALLAFGNFSEYPQTVTAHTLQAMPFK
AHDLIGGKTVSLNQDLTLQPYQVMWLEIA Series SEQ ID NO: 8: (Proteins = mutated sequences of glucan-saccharase
ASNp (Amylosucrase of *Neisseria polysaccharea*) V331X$_7$)
SPNSQYLKTRILDIYTPEQRAGIEKSEDWRQFSRRMDTHFPKLMNELDSVYGNNEALLPMLEMLLAQAWQSYSQR
NSSLKDIDIARENNPDWILSNKQVGGVCYVDLFAGDLKGLKDKIPYFQELGLTYLHLMPLFKCPEGKSDGGYAVS
SYRDVNPALGTIGDLREVIALLHEAGISAVVDFIFNHTSNEHEWAQRCAAGDPLFDNFYYIFPDRRMPDQYDRTL
REIFPDQHPGGFSQLEDGRWVWTTFNSFQWDLNYSNPWVFRAMAGEMLFLANLGVDILRMDAVAFIWKQMGTSCE
NLPQAHALIRAFNAVMRIAAPAVFFKSEAIX$_7$HPDQVVQYIGQDECQIGYNPLQMALLWNTLATREVNLLHQALT
YRHNLPEHTAWVNYVRSHDDIGWTFADEDAAYLGISGYDHRQFLNRFFVNRFDGSFARGVPFQYNPSTGDCRVSG
TAAALVGALQDDPHAVDRIKLLYSIALSTGGLPLIYLGDEVGTLNDDDWSQDSNKSDDSRWAHRPRYNEALYAQR
NDPSTAAGQIYQDLRHMIAVRQSNPRFDGGRLVTFNTNNKHIIGYIRNNALLAFGNFSEYPQTVTAHTLQAMPFK
AHDLIGGKTVSLNQDLTLQPYQVMWLEIA Series SEQ ID NO: 9: (Proteins = mutated sequences of glucan-saccharase
ASNp (Amylosucrase of *Neisseria polysaccharea*) D394X$_8$)
SPNSQYLKTRILDIYTPEQRAGIEKSEDWRQFSRRMDTHFPKLMNELDSVYGNNEALLPMLEMLLAQAWQSYSQR
NSSLKDIDIARENNPDWILSNKQVGGVCYVDLFAGDLKGLKDKIPYFQELGLTYLHLMPLFKCPEGKSDGGYAVS
SYRDVNPALGTIGDLREVIAALHEAGISAVVDFIFNHTSNEHEWAQRCAAGDPLFDNFYYIFPDRRMPDQYDRTL
REIFPDQHPGGFSQLEDGRWVWTTFNSFQWDLNYSNPWVFRAMAGEMLFLANLGVDILRMDAVAFIWKQMGTSCE
NLPQAHALIRAFNAVMRIAAPAVFFKSEAIVHPDQVVQYIGQDECQIGYNPLQMALLWNTLATREVNLLHQALTY
RHNLPEHTAWVNYVRSHDX$_8$IGWTFADEDAAYLGISGYDHRQFLNRFFVNRFDGSFARGVPFQYNPSTGDCRVSG
TAAALVGLAQDDPHAVDRIKLLYSIALSTGGLPLIYLGDEVGTLNDDDWSQDSNKSDDSRWAHRPRYNEALYAQR
NDPSTAAGQIYQDLRHMIAVRQSNPRFDGGRLVTFNTNNKHIIGYIRNNALLAFGNFSEYPQTVTAHTLQAMPFK
AHDLIGGKTVSLNQDLTLQPYQVMWLEIA SEQ ID NO: 10: (Protein = mutated sequences of glucan-saccharase
ASNp (Amylosucrase of *Neisseria polysaccharea*) R446X$_9$)
SPNSQYLKTRILDIYTPEQRAGIEKSEDWRQFSRRMDTHFPKLMNELDSVYGNNEALLPMLEMLLAQAWQSYSQR
NSSLKDIDIARENNPDWILSNKQVGGVCYVDLFAGDLKGLKDKIPYFQELGLTYLHLMPLFKCPEGKSDGGYAVS
SYRDVNPALGTIGDLREVIAALHEAGISAVVDFIFNHTSNEHEWAQRCAAGDPLFDNFYYIFPDRRMPDQYDRTL
REIFPDQHPGGFSQLEDGRWVWTTFNSFQWDLNYSNPWVFRAMAGEMLFLANLGVDILRMDAVAFIWKQMGTSCE
NLPQAHALIRAFNAVMRIAAPAVFFKSEAIVHPDQVVQYIGQDECQIGYNPLQMALLWNTLATREVNLLHQALTY
RHNLPEHTAWVNYVRSHDDIGWTFADEDAAYLGISGYDHRQFLNRFFVNRFDGSFARGVPFQYNPSTGDCX$_9$VSG
TAAALVGLAQDDPHAVDRIKLLYSIALSTGGLPLIYLGDEVGTLNDDDWSQDSNKSDDSRWAHRPRYNEALYAQR
NDPSTAAGQIYQDLRHMIAVRQSNPRFDGGRLVTFNTNNKHIIGYIRNNALLAFGNFSEYPQTVTAHTLQAMPFK
AHDLIGGKTVSLNQDLTLQPYQVMWLEIA Series SEQ ID NO: 11: (Protein = sequence of DSR-S-Δ4N (truncated
dextran-saccharase DSR-S vardel Δ4N of *Leuconostoc mesenteroides* B-512F))
TQQVSGKYVEKDGSWYYYFDDGKNAKGLSTIDNNIQYFYESGKQAKGQYVTIDNQTYYFDKGSGDELTGLQSIDG
NIVAFNDEGQQIFNQYYQSENGTTYYFDDKGHAATGIKNIEGKNYYFDNLGQLKKGFSGVIDGQIMTFDQETGQE
VSNTTSEIKEGLTTQNTDYSEHNAAHGTDAEDFENIDGYLTASSWYRPTGILRNGTDWEPSTDTDFRPILSVWWP
DKNTQVNYLNYMADLGFISNADSFETGDSQSLLNEASNYVQKSIEMKISAQQSTEWLKDAMAAFIVAQPQWNETS
EDMSNDHLQNGALTYVNSPLTPDANSNFRLLNRTPTNQTGEQAYNLDNSKGGFELLLANQEDNSNVVVEAEQLNW
LYYLMNFGTITANDADANFDGIRVDAVDNVDADLLQIAADYFKLAYGVDQANDATANQHLSILEDWSHNDPLYVTD
DQGSNQLTMDDYVHTQLIWSLTKSSDIRGTMQRFVDYYMVDRSNDSTENEAIPNYSFVRAHDSEVQTVIAQIVSD
LYPDVENSLAPPTEQLAAAFKVYNEDEKLADKKYTQYNMASAYAMLLTNKDTVPRVYYGDLYTDDGQYMATKSPY
YDAINTLLKARVQYVAGGQSMSVDSNDVLTSVRYGKDAMTASDTGTSETRTEGIGVIVSNNAELQLEDGHTVTLH
MGAAHKNQAYRALLSTTADGLAYYDTDENAPVAYTDANGDLIFTNESIYGVQNPQVSGYLAVWVPVGAQQDQDAR
TASDTTTNTSDKVFHSNAALDSQVIYEGFSNFQAFATDSSEYTNVVIAQNADQFKQWGVTSFQLAPQYRSSTDTS
FLDSIIQNGYAFTDRYDLGYGTPTKYGTADQLRDALKALHASGIQAIADWVPDQIYNLPEQELATVTRTNSFGDD
DTDSDIDNALYVVQSRGGGQYQEMYGGAFLEELQALYPSLFKVNQISTGVPIDGSVKITEWAAKYFNGSNIQGKG
AGYVLKDMGSNKYFKVVSNTEDGDYLPKQLTNDLSETGFTHDDKGIIYYTLSGYRAQNAFIQDDDNNYYYFDKTG
HLVTGLQKINNHTYFFLPNGIELVKSFLQNEDGTIVYFDKKGHQVFDQYITDQNGNAYYFDDAGVMLKSGLATID
GHQQYFDQNGVQVKDKFVIGTDGYKYYFEPGSGNLAILRYVQNSKNQWFYFDGNGHAVTGFQTINGKKQYFYNDG
HQSKFEFIDADGDTFYTSATDGRLVTGVQKINGITYAFDNTGNLITNQYYQLADGKYMLLDDSGRAKTGFVLQDG
VLRYFDQNGEQVKDAIIVDPDTNLS Series SEQ ID NO: 12: (Protein = sequence of glucan-saccharase α-1,2 BrS
(α-1,2 BrS of *Leuconostoc citreum* NRRL B-1299))
MRQKETITRKKLYKSGKSWVAAATAFAVMGVSAVTTVSADTQTPVGTTQSQQDLTGQRGQDKPTTKEVIDKKEPV
PQVSAQNAGDLSADAKTTKADDKQDTQPTNAQLPDQGNKQTNSNSDKGVKESTTAPVKTTDVPSKSVTPETNTSI
NGGQYVEKDGQFVYIDQSGKQVSGLQNIEGHTQYFDPKTGYQTKGELKNIDDNAYYFDKNSGNGRTFTKISNGSY
SEKDGMWQYVDSHDKQPVKGLYDVEGNLQYFDLSTGNQAKHQIRSVDGVTYYFDADSGNATAFKAVTNGRYAEQT
TKDKDGNETSYWAYLDNQGNAIKGLNDVNGEIQYFDEHTGEQLKGHTATLDGTTYYFEGNKGNLVSVVNTAPTGQ
YKINGDNVYYLDNNNEAIKGLYGINGNLNYFDLATGIQLKGQAKNIDGIGYYFDKDTGNGSYQYTLMAPSNKNDY
TQHNVVNNLSESNFKNLVDGFLTAETWYRPAQILSHGTDWVASTDKDFRPLITVWWPNKDIQVNYLRLMQNEGVL
NQSAVYDLNTDQLLLNEAAQQAQIGIEKKISQTGNTDWLNNVLFTTHDGQPSFIKQQYLWNSDSEYHTGPFQGGY
LKYQNSDLTPNVNSKYRNADNSLDFLLANDVDNSNPIVQAEDLNWLYYLLNFGSITTQGKENNSNFDSIRIDAVD
FVSNDLIQRTYDYLRAAYGVDKNDKEANAHLSLVEAGLDAGTTTIHQDALIESDIREAMKKSLTNGPGSNISLSN
LIQDKEGDKLIADRANNSTENVAIPNYSIIHAHDKDIQDKVGAAITDATGADWTNFTPEQLQKGLSLYYEDQRKI
EKKYNQYNIPSAYALLLTNKDTVPRVYYGDMYQDDGQYMQKGSLYFDTITALMEARKQFVAGGQTINVDDNGVLT
SVRFGKGAMTANDIGTNETRTQGIGVVIANDPSLKLSKDSKVTLHMGAAHRNQNYRALLLTTDNGIDSYSSSKNA
PVIKTDDNGDLVFSNQDINDQLNTKVHGFLNSEVSGYLSAWVPLDATEQQDARTLPSEKSVNDGKVLHSNAALDS
NLIYEAFSNFQPMPTNRNEYTNVVIADKADTFKSWGITSFEMAPQYRSSQDKTFLDSTIDNGYAFTDRYDLGFEK
PTKYGNELSDRQAIKQLHSSGMQVMADVVANQIYNLPGKEVASTNRVDWNGNNLSTPFGTQMYVVNTVGGGKYQN
KYGGEFLDKLKAAYPDIFRSKNYEYDVKNYGGNGTGSVYYTVDSKTRAELDTDTKIKEWSAKYMNGTNVLGLGMG

SEQUENCES:

YVLKDWQTGQYFNVSNQNMKFLLPSDLISNDITVQLGVPVTDKKIIFDPASAYNMYSNLPEDMQVMDYQDDKKST
PSIKPLSSYNNKQVQVTRQYTDSKGVSWNLITFAGGDLQGQKLWVDSRALTMTPFKTMNQISFISYANRNDGLFL
NAPYQVKGYQLAGMSNQYKGQQVTIAGVANVSGKDWSLISFNGTQYWIDSQALNTNFTHDMNQKVFVNTTSNLDG
LFLNAPYRQPGYKLAGLAKNYNNQTVTVSQQYFDDQGTVWSQVVLGGQTVWVDNHALAQMQVRDTNQQLYVNSNG
RNDGLFLNAPYRGQGSQLIGMTADYNGQHVQVTKQGQDAYGAQWRLITLNNQQVWVDSRALSTTIMQAMNDDMYV
NSSQRTDGLWLNAPYTMSGAKWAGDTRSANGRYVHISKAYSNEVGNTYYLTNLGQSTWIDKRAFTATFDQVVAL
NATIVARQRPDGMFKTAPYGEAGAQFVDYVTNYNQQTVPVTKQHSDAQGNQWYLATVNGTQYWIDQRSFSPVVTK
VVDYQAKIVPRTTRDGVFSGAPYGEVNAKLVNMATAYQNQVVHATGEYTNASGITWSQFALSGQEDKLWIDKRAL
QA

Series SEQ ID NO: 13: (Protein = sequence of glucan-saccharase GBD-CD2
(Truncated dextran sucrase DSR-E of *Leuconostoc mesenteroides* NRRL B-1299))
MAHHHHHHVTSLYKKAGSAAAPFTMAQAGHYITKNGNDWQYDTNGELAKGLRQDSNGKLRYFDLTTGIQAKGQFV
TIGQETYYFSKDHGDAQLLPMVTEGHYGTITLKQGQGTKTAWVYRDQNNTILKGLQNINGTLQFFDPYTGEQLKG
GVAKYDDKLFYFESGKGNLVSTVAGDYQDGHYISQDGQTRYADKQNQLVKGLVTVNGALQYFDNATGNQIKNQQV
IVDGKTYYFDDKGNGEYLFTNTLDMSTNAFSTKNVAFNHDSSSFDHTVDGFLTADTWYRPKSILANGTTWRDSTD
KDMRPLITVWWPNKNVQVNYLNFMKANGLLTTAAQYTLHSDQYDLNQAAQDVQVAIERRAISEHGTDWLQKLLFE
SQNNNPSFVKQQFIWNKDSEYHGGGDAWFQGGYLKYGNNPLTPTTNSDYRQPGNAFDFLLANDVDNSNPVVQAEN
LNWLHYLMNFGTITAGQDDANFDSIRIDAVDFIHNDTIQRTYDYLRDAYQVQQSEAKANQHISLVEAGLDAGTST
IHNDALIESNLREAATLSLTNEPGKNKPLTNMLQDVDGGTLITDHTQNSTENQATPNYSIIHAHDKGVQEKVGAA
ITDATGADWTNFTDEQLKAGLELFYKDQRATNKKYNSYNIPSIYALMLTNKDTVPRMYYGDMYQDDGQYMANKSI
YYDALVSLMTARKSYVSGGQTMSVDNHGLLKSVRFGKDAMTANDLGTSATRTEGLGVIIGNDPKLQLNDSDKVTL
DMGAAHKNQKYRAVILTTRDGLATFNSDQAPTAWTNDQGTLTFSNQEINGQDNTQIRGVANPQVSGYLAVMVPVG
ASDNQDARTAATTTENHDGKVLHSNAALDSNLIYEGFSNFQPKATTHDELTNVVIAKNADVFNNWGITSFEMAPQ
YRSSGDHTFLDSTIDNGYAFTDRYDLGFNTPTKYGTDGDLRATIQALHHANMQVMADVVDNQVYNLPGKEVVSAT
RAGVYGNDDATGFGTQLYVTNSVGGGQYQEKYAGQYLEALKAKYPDLFEGKAYDYWYKNYANDGSNPYYTLSHGD
RESIPADVAIKQWSAKYMNGTNVLGNGMGYVLKDWHNGQYFKLDGDKSTLPKGGRADPAFLYKVVSAWSHPQFEK Series SEQ ID NO: 14: (Protein = sequence of glucan-saccharase ASDg
(Amylosaccharase of *Deinococcus geothermalis*))
MLKDVLTSELAAQVRDAFDDDRDAETFLLRLERYGEDLWESLRAVYGDQVRALPGRLLEVMLHAYHARPAELRRL
DEARLLRPDWLQRPEMVGVVAYTDRFAGTLKGVEERLDYLEGLGVKYLHLMPLLRPREGENDGGYAVQDYRAVRP
DLGTMDDLSALARALRGRGISLVLDLVLNHVAREHAWAQKARAGDPKYRAYFHLFPDRRGPDAFEATLPEIFPDF
APGNFSWDEEIGEGEGGWVWTTFNSYQWDLNWANPDVFLEFVDIILYLANRGVEVFRLDAIAFIWKRLGTDCQNQ
PEVHHLTRALRAAARIVAPAVAFKAEAIVAPADLIHYLGTRAHHGKVSDMAYHNSLMVQLWSSLASRNTRLFEEA
LRAFPPKPTSTTWGLYVRCHDDIGWAISDEDAARAGLNGAAHRHFLSDFYSGQFPGSFARGLVFQYNPVNGDRRI
SGSAASLAGLEAALETGDPGRIEDAVRRLLLLHTVILGFGGVRPLLYMGDELALLNDYAFEDVPEHAPDNRWVHRP
QMDWALAERVRQEPSSPAGRVNTGLRHLLRVRRDTPQLHASIESQVLPSPDSRALLLRRDHPLGGMVQVYNFSEE
TVMLPSHVLRDVLGDHVQDRLSGSAFRLDRPTVRLEGYRALWLTAGEAPA Series SEQ ID NO: 15: (Protein = sequence of glucan-saccharase DSR-S-OK
(Dextran-saccharase of *Oenococcus kitaharae* DSM17330))
MMATGSNLITAQADDLNQEGTAAQSVSPSTAAANQSESSAQSTEQSATQAATDGEASTVSTAVTTITPHYVQQAG
KWLYMGSDGEFVKGPQTIDGNLQFFDEQGIQIKGSFETVDGSSYYFDSQSGNAVTGFKIINNDLHYFEEDGKETV
NNYATDKQGNIFYFDENGQMATGVKTIQGQSYYFDQDGHMRKGYSGVFDNQLVLYFDKTTGALANTNVSSIKEGLT
AQNDDFTAHNAVYSTKSESFTNIDGYLTAEAWYRPADILENGTDWRASRADEFRPILTTWWPDKQTEVNYLNYMK
TQGFITNDQDFKLSDDQLLLNHAAQSVQGEIEKKISQQGSTDWLKTLLQTFINQQPSWNGESEDPGSDHLQGGAL
TFVNSPLTPDSNSNFLLNRTPTNQTGTPQYDTDASLGGFELLLANDVDNSNPVVQAEQLNWLYYLLNFGSITADD
PNANFDGIRIDAVDNVDADLLQIAAAYFKDAFKSGSNDQTTNQHLSILEDWSHNDPEYMKAQGYPQLTMDDYMHT
QLIWSLTKPDNIRGTMQRFMDYYLVNRANDSTNNEAVANYSFVRAHDSEVQTVIAQIISDLYPNSGSGLIPTTDQ
LQAAFEVYNADMKSDVKKYTQYNIPSAYAMLLTNKDTVPRVYYGDMYTDDGDYMANKSPYFDAISTLLKARVKYA
AGGQSMAVDKNDILTSVRFGQNAMLASDSGDNQTRQEGIGVIVSNNSHLKLAENDQVVLHMGAAHKNQAFRALLL
TIESGLENFDTDLQPAVKYTDANGDLIFTAAELAGYLNPEVSGYLSAWVPVGAADNQDARTAADSATSTDGNVFH
SNAALDSNVIFEGFSNFQSIPTAEQHDDFTNVKIAENAGLFKDWGITSFQLAPQYRSSTDSTFLDSIIQNGYAFT
DRYDLGFDTPTKYGDVDDLRAAIKALHANNIQVMADWVPDQIYNLQNPEIITVNRTDSYGQPIAGSDLQNDLYLA
YTNGGGQYQTKFGGAFLEKLQQLYPDLFTKTQISTGQTIDPSQKITEWSAKYFNGSNIQGRGAYYVLRDSGTDQY
FKVISNDENEAFLPKQLTNQPGETGFSQDDQGIIFFSTSGYQAADNNQDGNYYYFDNTGHMVTGPQTINGRH
YLFFPNGVEAQNVFVQNDRGETYYYDQRGRQVANQYVTDTNGNSFRFDENGIMLANQLAQVDGHWQPFFKSSGVQA
KDAFILGSDGKLRYFESGNGNMAVNEFKGSENGRYYYFGADGQAVSGLQTINGRQLYFDDHGQQMKDAFYTNQSG
QRFYFNALTGDLVKFNFIYTSASSSFTPDNDSSDSYQGDSHLWYYADSQGQIVTGFQTINGHLQYFDDISGQMIT
NRFMRRADGNWIYLDENGEAVRGMRVINGLTNYFRDDFTQVKDGFAQDPNSGERHYFNGTNGAMVTNDYFSPDQI
HWYYADDSGQPVTGFQTIKGQVQYFDQDGIQLKGGSQTDPVTKQTYYFDDKFGNGQIL Series SEQ ID NO: 16: (Protein = sequence of glucan-saccharase α-1,3 BrS
(α-1,3 BrS of *Leuconostoc citreum* NRRL B-742))
MEMKETITRKKLYKSGKSWVAAATAFAVMGVSAVTTVSADTQTPVGTTQSQQDLTGQTGQDKPTTKEVIDKKEPV
PQVSAQNVGDLSADAKTPKADDKQDTQPTNAQLPDQGNKQTNSNSDKGVKESTTAPVKTTDVPSKSVAPETNTSI
NGGQYVEKDGQFVYIDQSGKQVSGLQNIEGHTQYFDPKTGYQTKGELKNIDDNAYYFDKNSGNGRTFTKISNGSY
SEKDGMWQYVDSHDKQPVKGLYDVEGNLQYFDLSTGNQAKHQIRSVDGVTYYFDADSGNATAFKAVTNGRYAEQT
TKDKDGNETSYWAYLDNQGNAIKGLNDVNGEIQYFDEHTGEQLKGHTATVDGTTYYFEGNKGNLVSVVNTAPTGQ
YKINGDNVYYLDNNNEAIKGLYGINGNLNYFDLATGIQLKGQAKNIDGIGYYFDQNNGNGEYRTSLTGPVVKDVY
SQHNAVNNLSANNFKNLVDGFLTAETWYRPAQILSHGTDWVASTDKDFRPLITVWWPNKDIQVNYLKLMQQIGIL
DNSVVFDTNNDQLVLNKGAESAQIGIEKKVSETGNTDWLNELLFAPNGNQPSFIKQQYLWNVDSEYPGGWFQGGY
LAYQNSDLTPYANTNPDYRTHNGLEFLLANDVDNSNPVVQAEQLNWLYYLMNFGQITANDSNANFDSMRIDAISF
VDPQIAKKAYDLLDKMYGLTDNEAVANQHISIVEAPKGETPITVEKQSALVESNWRDRMKQSLSKNATLDKLDPD
PAINSLEKLVADDLVNRSQSSDKDSSTIPNYSIVAHDKDIQDTVHIIMKIVNNNPNISMSDFTMQQLQNGLKAF
YEDQHQSVKKYNQYNIPSAYALLLLTNKDTVPRVFYGDMYQDYGDDLDGGQYMATKSIYYNAIEQMMKARLKYVAG

SEQUENCES:

```
GQIMAVTKIKNDGINKDGTNKSGEVLTSVRFGKDIMDAQGQGTAESRNQGIGVIVSNSSGLELKNSDSITLHMGI
AHKNQAYRALMLTNDKGIVNYDQDNNAPIAWTNDHGDLIFTNQMINGQSDTAVKGYLNPEVAGYLAVWVPGAND
NQDARTVTTNQKNTDGKVLHTNAALDSKLMYEGFSNFQKMPTRGNQYANVVITKNIDLFKSWGITDFELAPQYRS
SDGKKDITDRFLDSIVQNGYGLSDRYDLGFKTPTKYGTDQDLRKAIERLHQAGMSVMADFVANQIYGLHADKEVVS
AQHVNINGDTKLVVDPRYGTQMTVVNSVGGGDYQAKYGGEYLDTISKLYPGLLLDSNGQKIDLSTKIKEWSAKYL
NGNSIPQVGMGYVLKDWNNGQYFHILDKEGYSLPTQLVSNDPETQIGESVNYKYFIGNSDATYNMYHNLPNTVS
LINSQEGQIKTQQSGVTSDYEGQQVQVTRQYTDSKGVSWNLITFAGGDLQGQKLWVDSRALTMTPFKTMNQISFI
SYANRNDGLFLNAPYQVKGYQLAGMSNQYKGQQVTIAGVANVSGKDWSLISFNGTQYWIDSQALNTNFTHDMNQK
VFVNTTSNLDGLFLNAPYRQPGYKLAGLAKNYNNQTVTVSQQYFDDQGTVWSEVVLGGQTVWVDNHALAQMQVSD
TSQQLYVNSNGRNDGLFLNAPYRGQGSQLIGMTADYNGQHVQVTKQGQDAYGAQWRLITLNNQQVWVDSRALSTT
IVQAMNDDMYVNSNQRTDGLWLNAPYTMSGAKWAGDTRSANGRYVHISKAYSNEVGNTYYLTNLNGQSTWIDKRA
FTATFDQVVALNATIVARQRPDGMFKTAPYGEAGAQFVDYVTNYNQQTVPVTKQHSDAQGNQWYLATVNGTQYWI
DQRSFSPVVTKVVDYQAKIVPRTTRDGVFSGAPYGEVNAKLVNMATAYQNQVVHATGEYTNASGITWSQFALSGQ
EDKLWIDKRALQA
```

Series SEQ ID NO: 17: (Protein = sequence of glucan-saccharase ASR-C-del-bis (truncated alternane-saccharase of *Leuconostoc mesenteroides* NRRL B-1355))

```
MEQQETVTRKKLYKSGKVWVAAATAFAVLGVSTVTTVHADTNSNVAVKQINNTGTNDSGEKKVPVPSTNNDSLKQ
GTDGFWYDSDGNRVDQKTNQILLTAEQLKKNNEKNLSVISDDTSKKDDENISKQTKIANQQTVDTAKGLTTSNLS
DPITGGHYENHNGYFVYIDASGKQVTGLQNIDGNLQYFDDNGYQVKGSFRDVNGKHIYFDSVTGKASSNVDIVNG
KAQGYDAQGNQLKKSYVADSSGQTYYFDGNGQPLIGLQTIDGNLQYFNQGVQIKGGFQDVNNKRIYFAPNTGNA
VANTEIINGKLQGRDANGNQVKNAFSKDVAGNTFYFDANGVMLTGLQTISGKTYYLDEQGHLRKNYAGTFNNQFM
YFDADTGAGKTAIEYQFDQGLVSQSNENTPHNAAKSYDKSSFENVDGYLTADTWYRPTDILKNGDTWTASTETDM
RPLLMTWWPDKQTQANYLNFMSSKGLGITTTYTAATSQKTLNDAAFVIQTAIEQQISLKKSTEWLRDAIDSFVKT
QANWNKQTEDEAFDGLQWLQGGFLAYQDDSHRTPTDSGNNRKLGRQPINIDGSKDTTDGKGSEFLLANDIDNSNP
IVQAEQLNWLHYLMNFGSITGNNDNANFDGIRVDAVDNVDADLLKIAGDYFKALYGTDKSDANANKHLSILEDWN
GKDPQYVNQQGNAQLTMDYTVTSQFGNSLTHGANNRSNMWYFLDTGYYLNGDLNKKIVDKNRPSGTLVNRIANSG
DTKVIPNYSFVRAHDYDAQDPIRKAMIDHGIIKNMQDTFTFDQLAQGMEFYYKDQENPSGFKKYNDYNLPSAYAM
LLTNKDTVPRVYYGDMYLEGGQYMEKGTIYNPVISALLKARIKYVSGGQTMATDSSGKDLKDGETDLLTSVRFGK
GIMTSDQTTTQDNSQDYKNQGIGVIVGNNPDLKLNNDKTITLHMGKAHKNQLYRALVLSNDSGIDVYDSDDKAPT
LRTTNDNGDLIFHKTNTFVKQDGTIINYEMKGSLNALISQVYVGASDSQDARTVATESSSSNDGSVFHSN
AALDSNVIYEGFSNFQAMPTSPEQSTNVVIATKANLFKELGITSFELAPQYRSSGDTNYGGMSFLDSFLNNGYAF
TDRYDLGFNKADGNPNPTKYGTDQDLRNAIEALHKNGMQAIADWVPDQIYALPGKEVVTATRVDERGNQLKDTDF
VNLLYVANTKSSGVDYQAKYGGEFLDKLREEYPSLFKQNQVSTGQPIDASTKIKQWSAKYMNGTNILHRGAYYVL
KDWATNQYFNIAKTNEVFLPLQLQNKDAQTGFISDASGVKYYSISGYQAKDTFIEDGNGNWYYFDKDGYMVRSQQ
FENPIRTVESTSVNTRNGNYYFMPNGVELRKGFGTDNSGNVYYFDDQGKMVRDKYINDDANNFYHLNVDGTMSRG
```

Series SEQ ID NO: 18: (Protein = sequence of fructosyltransferase of *Bacillus subtilis* NCIMB 11871)

```
MNIKKFAKQATVLTFTTALLAGGATQAFAKETNQKPYKETYGISHITRHDMLQIPEQQKNEKYQVPEFDSSTIKN
ISSAKGLDVWDSWPLQNADGTVANYHGYHIVFALAGDPKNADDTSIYMFYQKVGETSIDSWKNAGRVFKDSDKFD
ANDSILKDQTQEWSGSATFTSDGKIRLFYTDFSGKHYGKQTLTTAQVNVSASDSSLNINGVEDYKSIFDGDGKTY
QNVQQFIDEGNYSSGDNHTLRDPHYVEDKGHKYLVFEANTGTEDGYQGEESLFNAKYYGKSTSFFRQESQKLLQS
DKKRTAELANGALGMIELNDDYTLKKVMLPLIANSTVTDEIERANVFKMNGKYLFTDSRGSKMTIDGITSNDIYM
LVYVSNSLTGPYKPLNKTGLVLKMDLDPNDVTFTYSHFAVPQAKGNNVVITSYMTNRGFYADKQSTFAPSFLLNI
KGKKTSVVKDSILEQGQLTVNK
```

---

The invention claimed is:

1. A process for manufacturing a glycosylated synthon, or monomer, comprising at least one step of placing at least one glycan-saccharase in contact with at least one hydroxylated synthon and at least one sucrose, in which:

(A) said hydroxylated synthon is chosen from the group constituted of:

(i) (meth)acrylate/(meth)acrylamide synthons of formula (I):

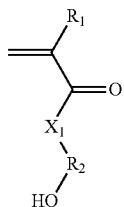

(I)

in which:

$R_1$ represents a hydrogen atom or a $C_1$-$C_3$ alkyl;

$R_2$ represents a $C_1$-$C_{20}$ alkylene group; or a group $(C_2H_4O)_n$, with n being an integer between 1 and 10; and $X_1$ represents —(O)—, —(NH)—, —(S)— or —(NR'$_2$(OH))—, with R'$_2$ representing a $C_1$-$C_{20}$ alkylene group; or a group —$(C_2H_4O)_m$—, with m being an integer between 1 and 10;

(ii) styrene-based synthons of formula (II):

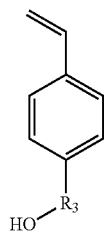

(II)

in which $R_3$ represents a covalent bond; a $C_1$-$C_{20}$ alkylene group; or a group $(C_2H_4O)_n$, with n being an integer between 1 and 10;

(iii) N-carboxyanhydride (NCA) synthons of formula (III):

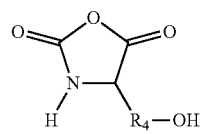

(III)

in which $R_4$ represents a covalent bond; a $C_1$-$C_{20}$ alkylene group; or a group $(C_2H_4O)_n$, with n being an integer between 1 and 10;

(iv) lactone/lactam/thiolactone synthons of formula (IV):

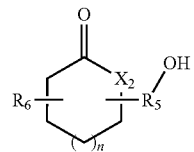

(IV)

in which:

$R_5$ represents a covalent bond; a $C_1$-$C_{20}$ alkylene group; or a group $(C_2H_4O)_m$, with m being an integer between 1 and 10;

n represents an integer between 1 and 20;

$X_2$ represents —(O)—, —(NH)— or —(S)—; and $R_6$ represents a hydrogen or a $C_1$-$C_{20}$ alkyl group;

(v) synthons of formula (V):

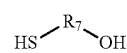

(V)

in which $R_7$ represents a $C_1$-$C_{20}$ alkylene group; and (vi) synthons of formula (VI):

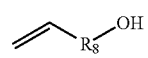

(VI)

in which $R_8$ represents a $C_1$-$C_{20}$ alkylene group; and (B) said glycan-saccharase is selected from the group consisting of a sequence having at least 80% identity with SEQ ID NO: 1, a sequence having at least 80% identity with SEQ ID NO: 1 mutated once at any one of the positions R226, I228, F229, A289, F290, I330, V331, D394 and R446;

a sequence having at least 80% identity with SEQ ID NO: 11;

a sequence having at least 80% identity with SEQ ID NO: 12;

a sequence having at least 80% identity with SEQ ID NO: 13;

a sequence having at least 80% identity with SEQ ID NO: 14;

a sequence having at least 80% identity with SEQ ID NO: 15;

a sequence having at least 80% identity with SEQ ID NO: 16;

a sequence having at least 80% identity with SEQ ID NO: 17; and a sequence having at least 80% identity with SEQ ID NO: 18.

2. The process as claimed in claim 1, in which the sequence having at least 80% identity with SEQ ID NO: 1 mutated once at any one of the positions R226, I228, F229, A289, F290, I330, V331, D394 and R446 is chosen from:

a sequence having at least 80% identity with SEQ ID NO: 2, said sequence having an amino acid $X_1$ representing an amino acid chosen from the group constituted of A, C, D, E, F, G, H, I, K, L, M, N, P, Q, S, T, V, W and Y;

a sequence having at least 80% identity with SEQ ID NO: 3, said sequence having an amino acid $X_2$ representing an amino acid chosen from the group constituted of A, C, D, E, F, G, H, L, M, N, P, Q, R, S, T, V, W and Y;

a sequence having at least 80% identity with SEQ ID NO: 4, said sequence having an amino acid $X_3$ representing an amino acid chosen from the group constituted of A, C, D, E, G, H, I, K, L, M, N, P, Q, R, S, T, V, W and Y;

a sequence having at least 80% identity with the sequence SEQ ID NO: 5, said sequence having an amino acid $X_4$ representing an amino acid chosen from the group constituted of C, D, E, F, G, H, I, K, L, M, N, P, Q, R, S, T, V, W and Y;

a sequence having at least 80% identity with the sequence SEQ ID NO: 6, said sequence having an amino acid $X_5$ representing an amino acid chosen from the group constituted of A, C, D, E, G, H, I, K, L, M, N, P, Q, R, S, T, V, W and Y;

a sequence having at least 80% identity with the sequence SEQ ID NO: 7, said sequence having an amino acid $X_6$ representing an amino acid chosen from the group constituted of A, C, D, E, F, G, H, K, L, M, N, P, Q, R, S, T, V, W and Y;

a sequence having at least 80% identity with SEQ ID NO: 8, said sequence having an amino acid $X_7$ representing an amino acid chosen from the group constituted of A, C, D, E, F, G, H, I, K, L, M, N, P, Q, R, 5, T, W and Y;

a sequence having at least 80% identity with SEQ ID NO: 9, said sequence having an amino acid $X_8$ representing an amino acid chosen from the group constituted of A, C, E, F, G, H, I, K, L, M, N, P, Q, R, S, T, V, W and Y; and a sequence having at least 80% identity with SEQ ID NO: 10, said sequence having an amino acid $X_9$ representing an amino acid chosen from the group constituted of A, C, D, E, F, G, H, I, K, L, M, N, Q, S, T, V, W and Y.

3. The process as claimed in claim 1, in which the sequence having at least 80% identity with SEQ ID NO: 1 mutated once at any one of the positions R226, I228, F229, A289, F290, I330, V331, D394 and R446 is chosen from:

a sequence having at least 80% identity with SEQ ID NO: 2, said sequence having an amino acid $X_1$ representing an amino acid chosen from the group constituted of C, H, K, M, N, Q, S, T and V;

a sequence having at least 80% identity with SEQ ID NO: 3, said sequence having an amino acid $X_2$ representing an amino acid chosen from the group constituted of H, L, T, V, W and Y;

a sequence having at least 80% identity with SEQ ID NO: 4, said sequence having an amino acid $X_3$ representing an amino acid chosen from the group constituted of C, D, E, G, H, I, K, M, N, P, Q, V, W and Y;

a sequence having at least 80% identity with the sequence SEQ ID NO: 5, said sequence having an amino acid $X_4$ representing an amino acid chosen from the group constituted of C, D, E, F, M, N, P, Q, S, T, V and W;

a sequence having at least 80% identity with the sequence SEQ ID NO: 6, said sequence having an amino acid $X_5$ representing an amino acid chosen from the group constituted of A, C, D, E, G, H, I, K, L, M, P, Q, S, T, V and W;

a sequence having at least 80% identity with the sequence SEQ ID NO: 7, said sequence having an amino acid $X_6$ representing an amino acid chosen from the group constituted of A, C, D, E, F, G, H, K, L, M, N, Q, S, V and Y;

a sequence having at least 80% identity with SEQ ID NO: 8, said sequence having an amino acid $X_7$ representing an amino acid chosen from the group constituted of A, C, D, E, F, G, H, I, K, L, N, Q, R, S, T, W and Y;

a sequence having at least 80% identity with SEQ ID NO: 9, said sequence having an amino acid $X_8$ representing an amino acid chosen from the group constituted of A, E, F, G, H, I, K and L;

a sequence having at least 80% identity with SEQ ID NO: 10, said sequence having an amino acid $X_9$ representing an amino acid chosen from the group constituted of A, C, G, K, L, M, N, and S.

4. The process as claimed in claim 1, in which the hydroxylated synthon is chosen from the group consisting of 2-(hydroxy)ethyl methacrylate (HEMA), N-(hydroxy)methylacrylamide (NHAM), N-(hydroxy)ethylacrylamide (HEAA), 4-vinylphenol (VP), 4-vinylbenzyl alcohol (VBA), 4-(hydroxy)methyloxazolidine-2,5-dione (HMNCA), a-(hydroxy)methylcaprolactone (AHMCL), (±)-mevalonolactone (MVL), 2-mercaptoethanol (BME), 2-propen-1-ol (allyl alcohol) and N,N-bis(2-hydroxyethyl)acrylamide (NNHEA).

5. The process as claimed in claim 1, in which the hydroxylated synthon is chosen from the group consisting of 2-(hydroxy)ethyl methacrylate (HEMA), N-(hydroxy)methylacrylamide (NHAM), N-(hydroxy)ethylacrylamide (HEAA), 4-vinylbenzyl alcohol (VBA), 2 propen-1-ol (allyl alcohol), 2-mercaptoethanol (BME) and N,N-bis(2-hydroxyethyl)acrylamide (NNHEA).

6. The process as claimed in claim 1, in which the hydroxylated synthon is glycosylated or fructosylated at the end of the process.

7. A process for manufacturing a glyco(co)polymer, comprising the polymerization of at least two monomers obtained, independently, on conclusion of the process as claimed in claim 1.

8. The process as claimed in claim 7, comprising, in the following order, the following steps:
a) polymerization of two monomers obtained, independently of each other, at the end of the process as claimed in claim 1, making it possible to obtain a chain of two monomers;
b) polymerization of the monomer chain obtained at the end of the preceding step with a monomer obtained at the end of the process as claimed in claim 1; and then
c) one or more successive, and independent, steps consisting in polymerizing the monomer chain obtained at the end of the preceding step with a monomer obtained at the end of the process as claimed in claim 1.

9. The process as claimed in claim 8, comprising, independently:
at least one step a') between steps a) and b);
at least one step b') between steps b) and c); and/or
at least one step c') after any one of the steps c), in which the monomer chain obtained on conclusion of the preceding step is polymerized with at least one non-glycosylated synthon.

10. A process for manufacturing a glyco(co)polymer, comprising the coupling of at least two monomers obtained, independently, at the end of the process as claimed in claim 1.

11. A process for manufacturing a glycol(co)polymer, comprising the coupling of a least two monomers obtained, independently, from synthons of Formula (V) and/or (VI) as defined in claim 1.

* * * * *